United States Patent
Pitlick et al.

(10) Patent No.: US 12,016,841 B2
(45) Date of Patent: *Jun. 25, 2024

(54) METHODS AND COMPOSITIONS FOR TREATMENT OF PRESBYOPIA, MYDRIASIS, AND OTHER OCULAR DISORDERS

(71) Applicant: Ocuphire Pharma, Inc., Farmington Hills, MI (US)

(72) Inventors: William H. Pitlick, Seattle, WA (US); Alan R. Meyer, North Riverside, IL (US); Mina Sooch, Bloomfield, MI (US); Konstantinos Charizanis, Ypsilanti, MI (US); Bernhard Hoffmann, Lake Forest, IL (US)

(73) Assignee: Ocuphire Pharma, Inc., Farmington Hills, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/708,466

(22) Filed: Mar. 30, 2022

(65) Prior Publication Data

US 2022/0226287 A1 Jul. 21, 2022

Related U.S. Application Data

(63) Continuation of application No. 17/230,270, filed on Apr. 14, 2021, which is a continuation of application No. 16/841,026, filed on Apr. 6, 2020, now Pat. No. 10,993,932, which is a continuation of application No. PCT/US2019/058182, filed on Oct. 25, 2019.

(60) Provisional application No. 62/751,391, filed on Oct. 26, 2018.

(51) Int. Cl.

| | | |
|---|---|---|
| *A61K 31/417* | (2006.01) | |
| *A61K 31/4178* | (2006.01) | |
| *A61P 27/08* | (2006.01) | |
| *A61P 27/10* | (2006.01) | |
| *A61K 9/00* | (2006.01) | |
| *A61K 9/08* | (2006.01) | |
| *A61K 47/12* | (2006.01) | |
| *A61K 47/26* | (2006.01) | |

(52) U.S. Cl.
CPC ........ *A61K 31/417* (2013.01); *A61K 31/4178* (2013.01); *A61P 27/08* (2018.01); *A61P 27/10* (2018.01); *A61K 9/0048* (2013.01); *A61K 9/08* (2013.01); *A61K 47/12* (2013.01); *A61K 47/26* (2013.01)

(58) Field of Classification Search
CPC ..... A61K 31/417; A61K 9/0048; A61P 27/02; A61P 27/08; A61P 27/10
See application file for complete search history.

(56) References Cited

U.S. PATENT DOCUMENTS

| | | |
|---|---|---|
| 4,252,721 A | 2/1981 | Silvestrini et al. |
| 4,443,441 A | 4/1984 | Galin |
| 4,508,715 A | 4/1985 | Booth et al. |
| 4,515,295 A | 5/1985 | Dougherty |
| 4,590,202 A | 5/1986 | Remy |
| 4,629,456 A | 12/1986 | Edwards |
| 4,659,714 A | 4/1987 | Watt-Smith |
| 4,834,727 A | 5/1989 | Cope |
| 4,888,344 A | 12/1989 | Sunagawa et al. |
| 4,906,613 A | 3/1990 | Watkins |
| 4,938,970 A | 7/1990 | Hustead et al. |
| 5,032,392 A | 7/1991 | Varma |
| 5,059,188 A | 10/1991 | Goddard |
| 5,134,124 A | 7/1992 | Nisato et al. |
| 5,149,320 A | 9/1992 | Dhaliwal et al. |
| 5,192,527 A | 3/1993 | Abrahmsohn |
| 5,261,903 A | 11/1993 | Dhaliwal et al. |
| 5,281,591 A | 1/1994 | Burke |
| 5,288,759 A | 2/1994 | DeSantis, Jr. |
| 5,488,050 A | 1/1996 | Neufeld |
| 5,514,118 A | 5/1996 | Kummer et al. |
| 5,584,823 A | 12/1996 | Valberg |
| 5,591,426 A | 1/1997 | Dabrowski et al. |
| 5,627,611 A | 5/1997 | Scheiner |
| 5,792,767 A | 8/1998 | Meyer et al. |
| 5,885,550 A | 3/1999 | Vallier |
| 5,891,882 A | 4/1999 | Meyer et al. |
| 5,891,913 A | 4/1999 | Sallmann et al. |
| 5,895,654 A | 4/1999 | Hartford et al. |
| 6,001,845 A | 12/1999 | Estok |
| 6,025,396 A | 2/2000 | Kim et al. |
| 6,043,224 A | 3/2000 | Lee et al. |
| 6,046,207 A | 4/2000 | Meyer et al. |

(Continued)

FOREIGN PATENT DOCUMENTS

| | | |
|---|---|---|
| CN | 101463009 A | 6/2009 |
| CN | 101969940 A | 2/2011 |

(Continued)

OTHER PUBLICATIONS

Abad et al., "Comparison of Astigmatism Correction Using Shorter Arc Length 90°/ 120° Asymmetric Intacs Severe Keratoconus Versus 150° Single-Segment Intacs Severe Keratoconus in Asymmetric Keratoconus," *Cornea*, (2011), vol. 30, No. 11, pp. 1201-1206.
ACETADOTE® Prescribing Information.
ACULAR® Prescribing Information.
Asa, "K-max Plus", retrieved from http://califasainc.com/pdf/Kmax_Analysis.pdf on May 29, 2016.
BETAGAN® Prescribing Information.
Benson et al., "Is Phentolamine Stable in Solution with Papaverine," *The Journal of Urology*, (1988), vol. 140, pp. 970-971.
CLARINEX® Prescribing Information.

(Continued)

*Primary Examiner* — Shobha Kantamneni
(74) *Attorney, Agent, or Firm* — Dechert LLP

(57) ABSTRACT

The invention provides methods, compositions, and kits containing an alpha-adrenergic antagonist, such as phentolamine, for use in monotherapy or as part of a combination therapy to treat patients suffering from presbyopia, mydriasis, and/or other ocular disorders.

14 Claims, 3 Drawing Sheets

(56) References Cited

U.S. PATENT DOCUMENTS

| | | |
|---|---|---|
| 6,051,594 A | 4/2000 | Lowery |
| 6,106,866 A | 8/2000 | Ranney |
| 6,291,498 B1 | 9/2001 | Horn |
| 6,420,407 B1 | 7/2002 | Horn |
| 6,432,401 B2 | 8/2002 | Weber et al. |
| 6,469,065 B1 | 10/2002 | Garvey et al. |
| 6,515,006 B2 | 2/2003 | Horn |
| 6,638,537 B2 | 10/2003 | Dennis et al. |
| 6,730,065 B1 | 5/2004 | Horn |
| 6,730,691 B1 | 5/2004 | Galin |
| 6,764,678 B2 | 7/2004 | Weber et al. |
| 6,872,390 B2 | 3/2005 | Weber et al. |
| 7,229,630 B2 | 6/2007 | Chen et al. |
| 7,569,230 B2 | 8/2009 | Chen et al. |
| 7,575,757 B2 | 8/2009 | Chen et al. |
| 7,868,035 B2 | 1/2011 | Woodward et al. |
| 8,299,079 B2 | 10/2012 | Kaufman |
| 8,445,526 B2 | 5/2013 | Horn |
| 8,580,787 B2 | 11/2013 | Horn |
| 8,597,629 B1 | 12/2013 | Horn |
| 8,889,112 B2 | 11/2014 | Horn |
| 8,979,809 B2 | 3/2015 | Horn |
| 9,089,560 B2 | 7/2015 | Meyer |
| 9,789,088 B2 | 10/2017 | Meyer |
| 9,795,560 B2 | 10/2017 | Meyer |
| 9,968,594 B2 | 5/2018 | Horn et al. |
| 10,064,818 B2 | 9/2018 | Horn et al. |
| 10,278,918 B2 | 5/2019 | Meyer |
| 10,507,245 B2 | 12/2019 | Vejarano Restrepo |
| 10,610,518 B2 | 4/2020 | Robinson et al. |
| 10,639,297 B2 | 5/2020 | Feinbaum et al. |
| 10,772,829 B2 | 9/2020 | Meyer |
| 10,993,932 B2 | 5/2021 | Pitlick et al. |
| 2002/0082288 A1 | 6/2002 | Horn |
| 2002/0183356 A1 | 12/2002 | Weber et al. |
| 2002/0183396 A1 | 12/2002 | Weber et al. |
| 2002/0187986 A1 | 12/2002 | Horn |
| 2003/0236306 A1 | 12/2003 | Chen et al. |
| 2004/0053894 A1 | 3/2004 | Mazess et al. |
| 2004/0176408 A1 | 9/2004 | Horn |
| 2005/0080056 A1 | 4/2005 | Horn |
| 2005/0203099 A1 | 9/2005 | Chen et al. |
| 2006/0211753 A1 | 9/2006 | Horn |
| 2006/0257388 A1 | 11/2006 | Knowles |
| 2007/0098748 A1 | 5/2007 | Chen et al. |
| 2008/0020076 A1 | 1/2008 | Jhamandas et al. |
| 2008/0039507 A1 | 2/2008 | Woodward et al. |
| 2009/0131303 A1 | 5/2009 | Hong et al. |
| 2009/0220618 A1 | 9/2009 | Xia et al. |
| 2009/0232763 A1 | 9/2009 | Kabra et al. |
| 2010/0029663 A1 | 2/2010 | Horn |
| 2010/0324031 A1 | 12/2010 | Kabra |
| 2011/0152274 A1 | 6/2011 | Kaufman |
| 2011/0178147 A1 | 7/2011 | Likitlersuang et al. |
| 2012/0136072 A1 | 5/2012 | Mosher et al. |
| 2012/0149748 A1 | 6/2012 | Shanler et al. |
| 2012/0208858 A1 | 8/2012 | Shanler et al. |
| 2012/0238615 A1 | 9/2012 | Chow et al. |
| 2012/0277239 A1 | 11/2012 | Horn et al. |
| 2013/0029919 A1 | 1/2013 | Gore et al. |
| 2013/0143938 A1 | 6/2013 | Horn |
| 2013/0172357 A1 | 7/2013 | Horn |
| 2014/0221445 A1 | 8/2014 | Meyer |
| 2014/0221446 A1 | 8/2014 | Meyer |
| 2015/0150848 A1 | 6/2015 | Horn |
| 2016/0008278 A1 | 1/2016 | Horn et al. |
| 2016/0008337 A1 | 1/2016 | Horn et al. |
| 2016/0051515 A1 | 2/2016 | Meyer |
| 2017/0065664 A1 | 3/2017 | Russ |
| 2018/0221274 A1 | 8/2018 | Meyer |
| 2018/0221340 A1 | 8/2018 | Meyer |
| 2019/0254963 A1 | 8/2019 | Meyer |
| 2019/0321337 A1 | 10/2019 | Robinson et al. |
| 2019/0358152 A1 | 11/2019 | Meyer |
| 2020/0246310 A1 | 8/2020 | Pitlick et al. |
| 2020/0253931 A1 | 8/2020 | Pitlick et al. |

FOREIGN PATENT DOCUMENTS

| | | |
|---|---|---|
| WO | WO-1995/005188 A1 | 2/1995 |
| WO | WO-1999/007353 A1 | 2/1999 |
| WO | WO-2001/019364 A1 | 3/2001 |
| WO | WO-2001/085171 A1 | 11/2001 |
| WO | WO-2005/123093 A2 | 12/2005 |
| WO | WO-2007/008666 A2 | 1/2007 |
| WO | 2009077736 A2 | 6/2009 |
| WO | WO-2010/0135731 A1 | 11/2010 |
| WO | WO-2011/050018 A1 | 4/2011 |
| WO | WO-2011/050030 A1 | 4/2011 |
| WO | WO-2012/075319 A2 | 6/2012 |
| WO | WO-2012/112566 A1 | 8/2012 |
| WO | WO-2012/119059 A1 | 9/2012 |
| WO | WO-2012/119070 A2 | 9/2012 |
| WO | WO-2013/115844 A1 | 8/2013 |
| WO | WO-2013/130577 A2 | 9/2013 |
| WO | WO-2014/121027 A1 | 8/2014 |
| WO | WO-2014/121028 A1 | 8/2014 |
| WO | 2018033792 A2 | 2/2018 |

OTHER PUBLICATIONS

Hadzija et al., "Physicochemical Stability of Papaverine Hydrochloride-Phentolamine Mesylate Mixtures Used for Intracavernous Injection: A Preliminary Evaluation," *The Journal of Urology*, (1988), vol. 140, pp. 64-65.

International Search Report and Written Opinion of the International Searching Authority, the U.S. Patent & Trademark Office, for International Application No. PCT/US2014/014067, dated May 21, 2014, 8 pages.

International Search Report and Written Opinion of the International Searching Authority, the U.S. Patent & Trademark Office, for International Application No. PCT/US2014/014070, dated Apr. 15, 2014, 10 pages.

Martell, A.E. "Chelates of Ascorbic Acid Formation and Catalytic Properties," Advances in Chemistry, vol. 200, pp. 153-187 (1982).

MUCOMYST® Prescribing Information.

OraVerse (phentolamine mesylate) Injection, Prescribing Information, 2 pages.

Safety Data Sheet for D-mannitol, by CCI (year 2012).

Safety Data Sheet for glycerol, by CCI (year 2012).

Soli et al., "Vasoactive Cocktails for Erectile Dysfunction: Chemical Stability of PGE1, Papaverine and Phentolamine," *The Journal of Urology*, (1998), vol. 160, pp. 551-555.

Troy et al., "Remington: The Science and Practice of Pharmacy", 21st ed., University of the Sciences, Philadelphia, Pennsylvania, 2006, p. 1032.

Tu et al., "Stability of papaverine hydrochloride and phentolamine mesylate in injectable mixtures," *American Journal of Hospital Pharmacy*, (1987), vol. 44, pp. 2524-2527.

Wang et al., "Degradation Kinetics of Phentolamine Hydrochloride in Solution," *Journal of Pharmaceutical Sciences*, (1988), Vo. 77, No. 11, pp. 972-976.

Vivacy, "Stylage", retrieved from http://www.stylage.eu/technology.html on May 27, 2016.

Abelson, et al., A. "The Truth about Tachyphylaxis", Review of Ophthalmology, (2006), vol. 13, No. 3, pp. 112-115.

Johnston, C. "Relief for Patients Troubled by Night-Vision Complaints: Presented at AAO", PeerVoice Publication, dated Oct. 21, 2010.

Murphy et al., "How red is white eye? Clinical grading of normal conjunctival hyperemia", May 2007, Eye, vol. 21, No. 4, pp. 633-638.

National Institutes of Health, "Visual acuity test", Feb. 23, 2015, online://medlineplus.gov/ency/article/003396.htm, 3 pages.

European Search Report dated Jun. 21, 2016 from European Patent Application 14746208.9 (6 pages).

(56) References Cited

OTHER PUBLICATIONS

Examination Report dated Jan. 31, 2018 from European Patent Application 14746208.9 (6 pages).
Notice of Intention to Grant a Patent dated Apr. 10, 2019 from European Patent Application 14746208.9 (162 pages).
Doughty, M.J. and Lyle, W. M. "A review of the clinical pharmacokinetics of pilocarpine, moxisylyte (thymoxamine), and dapiprazole in the reversal of diagnostic pupillary dilation," *Optom. Vis. Sci.*, (1992), vol. 69, No. 5, pp. 358-368. (Abstract Only).
Hara, H. et al., "Bunazosin, a Selective $\alpha_1$-Adrenoceptor Antagonist, as an Anti-glaucoma Drug: Effects on Ocular Circulation and Retinal Neuronal Damage," *Cardiovascular Drug Reviews*, (2005), vol. 23, No. 1, pp. 43-56.
Hogan, T. S. et al. "Dose-response study of dapiprazole HCI in the reversal of mydriasis induced by 2.5% phenylephrine," *J. Ocul. Pharmacol. Ther.*, (1997), vol. 13, No. 4, pp. 297-302. (Abstract Only).
Rev-Eyes™, in Physicians' Desk Reference for Ophthalmic Medicines (2003) Thomson PDR, p. 258.
"Safety and Efficacy of Ophthalmic Phentolamine Mesylate to Reverse Pharmacologically Induced Mydriasis", a clinical study description, available from clinicaltrials.gov online on Jul. 18, 2019.
"Safety and Efficacy of Ophthalmic Phentolamine Mesylate to Reverse Pharmacologically Induced Mydriasis", a clinical study description, available from clinicaltrials.gov online on Oct. 14, 2019.
"Safety and Efficacy of Ophthalmic Phentolamine Mesylate in Glaucoma", a clinical study description, available from clinicaltrials.gov online on Oct. 14, 2019.
"Single Dose Study of Phentolamine Mesylate Eye Drops in Patients With Severe Night Vision Disturbances", a clinical study description, available from clinicaltrials.gov online on May 23, 2019.
"Single Dose Study of Phentolamine Mesylate Eye Drops in Patients With Severe Night Vision Disturbances", a clinical study description, available from clinicaltrials.gov online on Oct. 14, 2019.
"Single Dose Study of Phentolamine Mesylate Eye Drops in Patients With Severe Night Vision Disturbances" a clinical study description, available from clinicaltrials.gov online on Aug. 1, 2019.
Anastasi, L. M. et al., "Effect of Pilocarpine in Counteracting Mydriasis," *Arch. Ophthal.*, vol. 79, pp. 710-715 (1968).
Barbee, R. F. and Smith, W. O. "A Comparative Study of Mydriatic and Cycloplegic Agents: in Human Subjects Without Eye Disease," *Am. J. Ophthalmol.*, vol. 44, No. 5 Pt. 1, pp. 617-622 (1957).
Batawi, H. and Micieli, J. A. "Adie's tonic pupil presenting with unilateral photophobia successfully treated with dilute pilocarpine," *BMJ Case Rep* (2020) 13:e233136. doi:10.1136/bcr-2019-233136.
Cohen, D. N. and Zakov, A. N. "The Diagnosis of Adie's Pupil Using 0.0625% Pilocarpine Solution," *Am. J. Ophthalmol.*, vol. 79, No. 5, p. 883 (1975).
Doughty, M. J. and Lyle, W. M. "A Review of the Clinical Pharmacokinetics of Pilocarpine, Moxisylyte (Thymoxamine), and Dapiprazole in the Reversal of Diagnostic Pupillary Dilation," *Optometry & Vision Science*, vol. 69, No. 5, pp. 358-368 (1992).
Drummond, P. D. "The Effect of Light Intensity and Dose of Dilute Pilocarpine Eyedrops on Pupillary Constriction in Healthy Subjects," *Am. J. Ophthalmol.*, vol. 112, No. 2, pp. 195-199, (1991).
Edgar, D. F et al., "Effects of dipivefrin and pilocarpine on pupil diameter, automated perimetry and LogMAR acuity," *Graefe's Arch. Clin. Exp. Ophthalmol.*, vol. 237, pp. 117-124 (1999).
Gambill, H. D. et al., "Mydriatic Effect of Four Drugs Determined With Pupillograph," *Arch. Ophthal.*, vol. 77, pp. 740-746 (1967).
Geyer, O. et al., "The additive miotic effects of dapiprazole and pilocarpine," *Graefe's Arch. Clin. Exp. Ophthalmol.*, vol. 233, pp. 448-451 (1995).
Gilmartin, B. et al., "Reversal of tropicamide mydriasis with single instillations of pilocarpine can induce substantial pseudo-myopia in young adults," *Ophthal. Physiol. Opt.*, vol. 15, No. 5, pp. 475-479 (1995).

Jacobson, D. M. and Olson, K. A. "Influence of Pupil Size, Anisocoria, and Ambient Light on Pilocarpine Miosis: Implications for Supersensitivity Testing," *Ophthalmology*, vol. 100, No. 2, pp. 275-280 (1993).
Leavitt, J. A. et al., "Pupillary Response to Four Concentrations of Pilocarpine in Normal Subjects: Application to Testing for Adie Tonic Pupil," *American Journal of Ophthalmology*, vol. 133, pp. 333-336 (2002).
Muftuoglu, O. et al., "Drug-induced intraocular lens movement and near visual acuity after AcrySof intraocular lens implantation," *J. Cataract. Refract. Surg.*, vol. 31, pp. 1298-1305 (2005).
Ozulken, K. et al., "Effect of topical pilocarpine on refractive surgery outcomes," *Int. Ophthalmol.*, vol. 40, pp. 733-740 (2020).
Ramsay, D. A. "Dilute Solutions of Phenylephrine and Pilocarpine in the Diagnosis of Disordered Autonomic Innervation of the Iris: Observations in Normal Subjects, and in the Syndromes of Horner and Holmes-Adie," *Journal of the Neurological Sciences*, vol. 73, pp. 125-134 (1986).
Smith, S. A. et al., "An increased effect of pilocarpine on the pupil by application of the drug in oil," *British Journal of Ophthalmology*, vol. 62, pp. 314-317 (1978).
Thompson, H. S. "Adie's Syndrome: Some New Observations," *Tr. Am. Ophth. Soc.*, vol. 75, pp. 587-626 (1977).
Zimmerman, T. J. "Pilocarpine," *Ophthalmology*, vol. 88, No. 1, pp. 85-88 (1981).
Abdelkader, A. and Kaufman, H. E., "Clinical outcomes of combined versus separate carbachol and brimonidine drops in correcting presbyopia," *Eye and Vision*, 3(1), 31 (2016).
Ackerman, S.L. et al., "Low-dose brimonidine for relief of ocular redness: Integrated analysis of four clinical trials," *Clinical and Experimental Optometry*, 102(2), 131-139 (2019).
Akutsu, H. et al., "Contrast Sensitivity and Reading Through Multifocal Intraocular Lenses," *Arch Ophthalmol*,110:1076-1080 (1992).
Al-Khersan, H. et al., "Retinal Detachments Associated With Topical Pilocarpine Use for Presbyopia," *Am J Ophthalmol*. (2022)doi:10.1016/j.ajo.2022.05.011.
Alio, J.L., and Azar, D.T., "Management of Complications in Refractive Surgery," *Springer* (2018).
Amarikwa, L. et al., "Vitreofoveal Traction Associated With Pilocarpine for Presbyopia," *Ophthalmic Surg Lasers Imaging Retina.*, 53(7):410-411. doi: 10.3928/23258160-20220629-01 (Jul. 2022).
American Optometric Association. Adult Vision: 41 to 60 Years of Age (2022).
American Society of Health System Pharmacists; AHFS Drug Information 2010. Bethesda, MD, p. 1386 (2010).
Antonelli-Incalzi, R. and Pedone, C., "Respiratory effects of beta-adrenergic receptor blockers," *Curr Med Chem.*, 14(10), 1121-1128 (2007). doi:10.2174/092986707780362853.
Applegate, R.A. et al., "Metrics of retinal image quality predict visual performance in eyes with 20/17 or better visual acuity," *Optom Vis Sci.*, 83(9) 635-640 (2006).
Bellucci, R. et al., "Visual acuity and contrast sensitivity comparison between Tecnis and Acrysof AS60 At intraocular lenses," *J. Cataract Refract Surg.*, 31:712-717 (2005).
Besada, E. et al., "Pupillometry Study of Brimonidine Tartrate 0.2% and Apraclonidine 0.5%," *The Journal of Clinical Pharmacology*, 51(12), 1690-1695 (2011).
Betoptic Pilo PI (2006).
Bidgoli, S.and Alio, J.L., "Night Vision Disturbances Following Refractive Surgery: Causes, Prevention, and Treatment," (2018).
Boger, W.P. et al., "Clinical Trial Comparing Timolol Ophthalmic Solution to Pilocarpine in Open-Angle Glaucoma," *American Journal of Ophthalmology*, 86(1), 8-18 (1978).
Boland, M.V. et al., "Electronic monitoring to assess adherence with once-daily glaucoma medications and risk factors for nonadherence: the automated dosing reminder study," *JAMA Ophthalmol*, 132(7), 838-844 (2014), doi:10.1001/jamaophthalmol.2014.856.
Boyer, D. et al., "Phentolamine Ophthalmic Solution Rapidly Reverses Pharmacologically Induced Mydriasis in Two Pivotal Phase 3 MIRA Trials," ASRS Annual Meeting, Abstract ID 665511 (2022).

(56) References Cited

OTHER PUBLICATIONS

Bradley, A.E. et al., "International Harmonization of Nomenclature and Diagnostic Criteria (INHAND): Nonproliferative and Proliferative Lesions of the Rabbit," *J Toxicol Pathol.* 34(3 Suppl):183S-292S (2021).

British Journal of Ophthalmology, European Glaucoma Society Terminology and Guidelines for Glaucoma, 4th Edition—Chapter 3: "Treatment Principles and Options." *Br J Ophthalmol.* 101(6):130-195, BJO (2017). [No authors listed].

Brooks et al., "Patient subjective visual function after corneal collagen crosslinking for keratoconus and corneal ectasia," *J Cataract Refract Surg.*, 38(4),615-619 (2012), doi:10.1016/j.jors.2011.11.029.

Bruner, R.H. et al., "Spontaneous hibernomas in Sprague-Dawley rats," *Toxicol Pathol.*, 37(4):547-52 (2009), doi:10.1177/0192623309335061.

Brunton, L. et al., "Goodman & Gilman's Pharmacological Basis of Therapeutics, 12e," *McGraw-Hill Education/Medical* (2011).

Büscher, R. et al., "Comparison of guinea-pig, bovine and rat alpha 1-adrenoceptor subtypes," *Br J Pharmacol.*, 117(4):703-711 (1996).

Cankurtaran, V. and Tekin, K., "Effects of a Single Dose of Topical Brimonidine 0.15% on Anterior Segment Morphology, Pupil Characteristics, and Choroidal Thickness in Healthy Subjects," *Eye & Contact Lens: Science & Clinical Practice*, 47(6), 323-329 (2001), https://doi.org/10.1097/ICL.0000000000000708.

Canovetti, A. et al., "Aceclidine, brimonidine tartrate, and dapiprazole: Comparison of miotic effect and tolerability under different lighting conditions," *Journal of Cataract and Refractive Surgery*, 35(1), 42-46 (2009), https://doi.org/10.1016/j.jcrs.2008.09.009.

CDRH FDA Tecnis Multifocal IOL: P080010: CDRH/FDA, "Summary of Safety and Effectiveness," (2009) https://www.accessdata.fda.gov/cdrh_docs/pdf8/P080010B.pdf.

CDRH/FDA, "Summary of Safety and Effectiveness of VISX STAR Excimer Laser System," (2007).

Chu, Y.R. et al., "The Safety of Phentolamine Ophthalmic Solution for Reversal of Pharmacologically Induced Mydriasis from Multiple Late-Stage Clinical Trials," ASCRS Annual Meeting, Paper ID 80618 (2022).

Chylak, L.T. et al., "Loss of contrast sensitivity in diabetic patients with LOCSII classified cataracts," *Brit J Ophthalmol.*, 77:78-11 (1993).

Csaky, K.G. et al., "Report from the NEI/FDA ophthalmic clinical trial design and endpoints symposium," *Invest Ophth Vis Sci.* 49(2) 479-489 (2008).

Dart, R.C., *Medical Toxicology*, 3 ed., Lippincott Williams & Wilkins. Philadelphia, PA, 719 (2004).

De La Torre, J.C. et al., "Impaired Cerebromicrovascular Perfusion," *Annals of the New York Academy of Sciences*, Jan. 25, 2006.

Deeb, S.E. et al., "Evaluation of monolithic C18 HPLC columns for the fast analysis of pilocarpine hydrochloride in the presence of its degradation products," *Die Pharmazie*, 9, 751-756 (2006).

DeGraff, A.C. et al., "Phentolamine," *American Heart J*, 92:397-402 (1976) doi:10.1016/s0002-8703(76)80121-4.

Devries, D. et al., "Phentolamine Ophthalmic Solution Reverses Pharmacologically Induced Mydriasis in Healthy Subjects: Subgroup Analyses in the Pivotal Phase 3 MIRA-2 Randomized Placebo Controlled Trial," ARVO Annual Meeting, Abstract ID 3709630 (2022).

Dexl, A.K. et al., "Reading performance after implantation of a small-aperture corneal inlay for the surgical correction of presbyopia: Two-year follow-up," *J Cataract Refract Surg*, 37(3), 525-531 (2011) doi:10.1016/j.jcrs.2010.10.044.

Dick, H.B. et al., "Contrast sensitivity after implantation of toric iris-claw lenses in phakic eyes," *J Cataract Refract Surg.*, 30:2284-2289 (2004).

Diestelhorst, M. et al., "Combined Therapy of Pilocarpine or Latanoprost with Timolol Versus Latanoprost Monotherapy," *Survey of Ophthalmology*, 47, S155-S161 (2002) https://doi.org/10.1016/S0039-6257(02)00329-6.

Dinsmore, W.W. and Alderdice, D.K., "Vasoactive intestinal polypeptide and phentolamine mesylate administered by autoinjector in the treatment of patients with erectile dysfunction resistant to other intracavernosal agents," *Brit J Urology*, 81:437-440 (1988).

Dragoi, V., "Ocular Motor System. In: Neuroscience Online: An Electronic Textbook for the Neurosciences," The University of Texas Health Science Center at Houston (2020).

Draize, J.H. et al., "Methods for the study of irritation and toxicity of substances applied topically to the skin and mucous membranes," *J Pharmacol Exp Ther*, 82:377-390 (1944).

Draize, J.H., "Appraisal of the Safety of Chemicals in Foods, Drugs and Cosmetics," *The Association of Food and Drug Officials of the United States*, 49-51 (1955).

Drews-Bankiewiez, M. et al., "Contrast Sensitivity in Patients with Nuclear Cataracts," *Arch. Ophthalmol*, 110: 953-959 (1992).

Drugbank Online, "Phentolamine" https://go.drugbank.com/drugs/DB00692 Accessed Aug. 25, 2022.

Drum, B. et al., "Assessment of visual performance in the evaluation of new medical products," In: *Drug Discoveries Today: Technologies*, Lam K, Timmerman H, eds. Elsevier., 4(2) 55-61 (2007).

Du, H. et al., "Cell membrane chromatography competitive binding analysis for characterization of α1A adrenoreceptor binding interactions," *Anal Bioanal Chem.*, 400(10):3625-3633 (2011) https://pubmed.ncbi.nlm.nih.gov/21544500/.

Durand-Cavagna, G. et al., "Spontaneous pre-Descemet's membrane corneal opacities in rabbits," *Lab Anim Sci*, 48(3):310-3 (1998).

Elliott, D.B. et al., "Improvements in clinical and functional vision and perceived visual disability after first and second eye cataract surgery," *Brit J Ophthalmol.*, 81:889-895 (1997).

Elliott, D.B. et al., "The reliability of the Pelli-Robson chart," *Ophthalmology and Physiological Optics.*, 10:21-24 (1990).

Enroth-Cugell et al., "The contrast sensitivity of retinal ganglion cells of the cat.," *J Physiol.*, 187:517-552 (1966).

Eton, E.A. et al., "Rhegmatogenous Retinal Detachment Following Initiation of Pilocarpine Hydrochloride Ophthalmic Solution 1.25% for Treatment of Presbyopia," *Ophthalmic Surg Lasers Imaging Retina.*, 53(7):410-411 (2022) doi: 10.3928/23258160-20220629-01.

European Glaucoma Society Terminology and Guidelines for Glaucoma, 4th Edition—Chapter 3, "Treatment principles and options," *Br J Ophthalmol*, 101(6):130-95 (2017).

Eydelman, M. et al., "Symptoms and Satisfaction of Patients in the Patient-Reported Outcomes With Laser In Situ Keratomileusis (PROWL) Studies," *JAMA Ophthalmol.*, 135(1):13-22 (2017).

Fan, T.Y. et al., "Improved high-performance liquid chromatographic determination of pilocarpine and its degradation products in ophthalmic solutions importance of octadecylsilane col. choice," *Journal of Chromatography A*, 740(2):289-295 (1996). doi:10.1016/0021-9673(96)00120-3.

Fan-Paul, N. et al., "Night vision disturbances after corneal refractive surgery," *Surv Ophthalmol*, 47(6), 533-546 (2002). doi:10.1016/s0039-6257(02)00350-8.

Fejer, T.P. et al., "Night myopia: implications for the young driver," *Can J Ophthalmol*, 27(4), 172-176, (1992) Retrieved from https://www.ncbi.nlm.nih.gov/pubmed/1633588.

Foster, S. et al., "MIRA-4, Clinical Trial Evaluating the Safety and Efficacy of Phentolamine Ophthalmic Solution for Reversal of Pharmacologically Induced Mydriasis in Pediatric Subjects Aged 3-11 Years," AAOpt Annual Meeting, Abstract ID 10569 (2022).

Fricke, T. R. et al., "Global Prevalence of Presbyopia and Vision Impairment from Uncorrected Presbyopia: Systematic Review, Meta-analysis, and Modelling," *Ophthalmology*, 125(10), 1492-1499 (2018), doi:10.1016/j.ophtha.2018.04.013.

Ginsburg, A.P., "Contrast sensitivity and functional vision in Functional Vision," In Packer, M, editor. *Functional Vision*. Philadelphia (PA) Lippincott Williams & Wilkins, 5-15. (Int. Ophthalmol Clin, vol. 43) (2003).

Ginsburg, A.P., "Contrast sensitivity: determining the visual quality and function of cataract, intraocular lenses and refractive surgery," *Curr Opin Ophthalmol.*, 17:19-26 (2006).

(56) References Cited

OTHER PUBLICATIONS

Ginsburg, A.P., "Vision Channels, Contrast Sensitivity and Functional Vision in Human Vision and Electronic Imaging IX," Rogowitz, BE, ed. SPIE-IS&T, 529:215-25 (2004).
Giovannitti, J.A., Jr. et al., "Alpha-2 adrenergic receptor agonists: a review of current clinical applications," *Anesth Prog*, 62(1), 31-39 (2015).
Godbillon J., "Determination of the major metabolite of phentolamine in human plasma and urine by high performance liquid chromatography," *J Chromatography.*, 222:461-466 (1981).
Goel, M. et al., "Aqueous humor dynamics: a review," *Open Ophthalmol J*, 4, 52-59 (2010), doi:10.2174/1874364101004010052.
Goertz, A.D. et al., "Review of the impact of presbyopia on quality of life in the developing and developed world," *Acta Ophthalmol.*, 92(6):497-500 (2014).
Goldstein, I., "Oral phentolamine: an alpha-1, alpha-2 adrenergic antagonist for the treatment of erectile dysfunction," *Int J Impot Res.*, 12(S1):S75-S80 (2000).
Gomez-Gomar, A. et al., "HPLC method for the simultaneous determination of pilocarpine, isopilocarpine, pilocarpic acid and isopilocarpic acid," *Journal of Pharmaceutical and Biomedical Analysis.*, 7(12):1729-1734 (1989), doi:10.1016/0731-7085(89)80187-6.
Hays, R.D. et al., "Assessment of the Psychometric Properties of a Questionnaire Assessing Patient-Reported Outcomes With Laser In Situ Keratomileusis (PROWL)," *JAMA Ophthalmol.* 135(1):3-12 (2017).
Hersh, E.V. et al., "Phase Four, Randomized, Double-Blinded, Controlled Trial of Phentolamine Mesylate in Two- to Five-year-old Dental Patients," *Pediatr Dent*, 39(1), 39-45 (2017).
Hersh, E.V. et al., "Phentolamine mesylate for accelerating recovery from lip and tongue anesthesia," *Dent Clin North Am*, 54:631-642. doi: 10.1016/j.cden.2010.06.004 (2010).
Hill, C.E. et al., "Specificity of innervation of iris musculature by sympathetic nerve fibres in tissue culture," *Pflugers Arch*, 361(2), 127-134 (1976), doi:10.1007/BF00583456.
Holladay, J.T. et al., "Functional vision and corneal changes after laser in situ keratomileusis determined by contrast sensitivity, glare testing and corneal topography," *J Cataract Refract Surg.*, 25:664-669 (1999).
Holladay, J.T. et al., "Phentolamine Mesylate Ophthalmic Solution Once Daily Reduces Pupil Diameter and Improves Night Vision Disturbances," AAO Annual Meeting, PA025 (2018).
Holve, D., "Optical Coherence Tomography and Slit Lamp Imaging of Corneal Dystrophy in the Dutch Belted Rabbit," Unpublished data.
Hong, D., "Tropicamide," [Updated Jul. 4, 2020]. In: StatPearls [Internet]. Treasure Island (FL): StatPearls Publishing (2020).
Howe, J.W., "The objective assessment of contrast sensitivity function by electrophysiological means," *Brit J Ophthalmology.*, 68:626-638 (1984).
Ishikawa, H. et al., "Comparison of post-junctional alphaadrenoceptors in iris dilator muscle of humans, and albino and pigmented rabbits," *Naunyn Schmiedebergs Arch Pharmacol*, 354(6), 765-772 (1996), doi:10.1007/BF00166903.
Isopto, Isopto® Carpine (Pilocarpine Hydrochloride Ophthalmic Solution) FDA Documents 1%, 2% and 4%. Highlights of Prescribing Information (2010).
Israilov, S. et al., "Intracavernous injections for erectile dysfunction in patients with cardiovascular diseases and failure or contraindications for sildenafil citrate," *Int/ J Impot Res.*, 14:38-43 (2002).
Jackson, M. et al., "A Combination of Phentolamine Eye Drops and Low Dose Pilocarpine Improves Near Vision in VEGA-1 Phase 2 Presbyopia Trial," AAO (2022).
Jin, B. et al., "Degradation Characteristics of a Novel PAF Receptor Antagonist, SY0916, in Aqueous Solution." *Journal of Analytical Methods in Chemistry*, vol. 2019, Article ID 8789470, 8 pages (2019), https://doi.org/10.1155/2019/8789470.

Kan, X., "UPLC-MS/MS Determination of Phentolamine in Human Plasma and its Application to a Pharmacokinetic Study," *Drug Res* (Stuttg), 64(11):607-612 (2014), doi:10.1055/s-0033-1364002.
Kannarr, S. et al., "LYNX-1: A Pivotal Phase 3 Randomized Placebo-Controlled Trial of Phentolamine Ophthalmic Solution in Subjects with Dim Light Vision Disturbance," AAOpt Annual Meeting, Abstract ID 10526 (2022).
Karpecki, P.M. et al., "Phentolamine eye drops reverse pharmacologically induced mydriasis in a randomized phase 2b trial," *Optom Vis Sci.*, 98(3):234-242 (2021).
Kass, M A. et al., "The Ocular Hypertension Treatment Study: a randomized trial determines that topical ocular hypotensive medication delays or prevents the onset of primary open-angle glaucoma," *Arch Ophthalmol*, 120(6), 701-713; discussion 829-730 (2002), doi:10.1001/archopht.120.6.701.
Kato, C.O.S. et al., "Effects of brimonidine tartrate 0.1% ophthalmic solution on the pupil, refraction, and light reflex," *Sci Rep.*, 8(1):9003 (2018), doi:10.1038/s41598-018-27436-8.
Katz, J. et al., "VEGA-1: Phentolamine Ophthalmic Solution as a Single Agent Improves Distance-Corrected Near Visual Acuity in Patients with Presbyopia," ARVO Annual Meeting, Abstract ID 3712883 (2022).
Kennedy, "High-performance liquid chromatographic analysis of pilocarpine hydrochloride, isopilocarpine, pilocarpic acid and isopilocarpic acid in eye-drop preparations," *Journal of Chromatography A*, 212(3), 331-338, ISSN 0021-9673 (1981), https://doi.org/10.1016/S0021-9673(01)84046-2.
Kerger, B.D. et al., "An assay for phentolamine using high performance liquid chromotography with electrochemical detection," *Analyt Biochem*, 170:145-151 (1988) doi: 10.1016/0003-2697(88)90102-9.
Kesler A. et al., "Effect of brimonidine tartrate 0.2% ophthalmic solution on pupil size," *Journal of Cataract and Refractive Surgery* 30(8):1707-1710 (2004), doi:10.1016/j.jers.2004.02.043.
Kiel, J.W. and Reitsamer, H.A., "Paradoxical effect of phentolamine on aqueous flow in the rabbit," *J Ocul Pharmacol Ther*, 23(1), 21-26 (2007), doi:10.1089/jop.2006.0102.
Kimlin, J.A. et al., "Nighttime Driving in Older Adults: Effects of Glare and Association With Mesopic Visual Function," *Invest Ophthalmol Vis Sci*, 58(5), 2796-2803 (2017), doi:10.1167/iovs.16-21219.
Kinney, M., "Temporal Effects of 2% Pilocarpine Ophthalmic Solution on Human Pupil Size and Accommodation," *Military Medicine*, 185(Supplement_1):435-442 (2020), doi:10.1093/milmed/usz235.
Kirsten, R. et al., "Clinical pharmacokinetics of vasodilators. Part II," *Clin Pharmacokinet*, 35(1):9-36 (1998), doi: 10.2165/00003088-199835010-00002.
Klein, B.E. et al., "Prevalence of glaucoma. The Beaver Dam Eye Study," *Ophthalmology*, 99(10), 1499-1504 (1992), doi:10.1016/s0161-6420(92)31774-9.
Kobayashi, H. et al., "Efficacy of bunazosin hydrochloride 0.01% as adjunctive therapy of latanoprost or timolol," J Glaucoma 13(1), 73-80 (2004), doi:10.1097/00061198-200402000-00014.
Konno, F. and Takayanagi, I., "Characterization of postsynaptic alpha-1 adrenoceptors in the rabbit iris dilator smooth muscle," *Naunyn Schmiedebergs Arch Pharmacol* 333:271-276 (1986), doi: 10.1007/BF00512940.
Koss, M.C., & Gherezghiher, T., "Pharmacological characterization of alphaadrenoceptors involved in nictitating membrane and pupillary responses to sympathetic nerve stimulation in cats," *Naunyn Schmiedebergs Arch Pharmacol*, 337(1), 18-23 (1988), doi:10.1007/BF00169471.
Krupin, T. et al., "Effect of prazosin on aqueous humor dynamics in rabbits," *Arch Ophthalmol*, 98(9), 1639-1642 (1980), doi:10.1001/archopht.1980.01020040491021.
Kupersmith, M.J. et al., "Contrast sensitivity loss in multiple sclerosis," *Invest Ophthalmol Vis Sci.*, 25:632-639 (1984).
Kwon, Y.H. et al., "Primary open-angle glaucoma," *N Engl J Med*, 360(11), 1113-1124 (2009), doi:10.1056/NEJMra0804630.
Lai, J.S. et al., "The efficacy and safety of combined phacoemulsification, intraocular lens implantation, and limited goniosynechialysis, followed by diode laser peripheral iridoplasty, in the treatment of

(56) References Cited

OTHER PUBLICATIONS cataract and chronic angle-closure glaucoma," *J Glaucoma.*, 10(4):309-15 (2001), doi: 10.1097/00061198-200108000-00011. PMID: 11558816.
Langevin, N.E. et al., "Historical Data: Histopathology Lesions Observed in the Eyes of Control Rabbits in Topical Ocular Administration and Contact Lens Studies," *Toxicologic Pathology* 46(7): 799-820 (2018).
Lee, J.H. et al., "Efficacy of brimonidine tartrate 0.2% ophthalmic solution in reducing halos after laser in situ keratomileusis," *Journal of Cataract and Refractive Surgery*, 34(6):963-967 (2008), doi:10.1016/j.jcrs.2008.01.028.
Lewis, R.A. et al., "Fixed-dose combination of AR-13324 and latanoprost: A double-masked, 28-day, randomised, controlled study in patients with open-angle glaucoma or ocular hypertension," *Br. J. Ophthalmol.* 100, 339-344 (2016).
Lin et al., "Pharmacokinetics Study of Phentolamine Mesylate Injection in Healthy Volunteers. In Sichuan da xue xue bao. Yi xue ban = *Journal of Sichuan University*," Medical science edition, 49 (6), 929-933 (2018).
Liu, J.C., "Assessing the utility of 2.5% phenylephrine for diagnostic pupillary dilation," *Can J Ophthalmol*, 52(4), 349-354 (2017), doi:10.1016/j.jcjo.2017.01.023.
Lograno, M.D. and Reibaldi, A., "Receptor-responses in fresh human ciliary muscle," *Br J Pharmacol*, 87(2), 379-385 (1986), doi:10.1111/j.1476-5381.1986.tb10827.
Marshall, L.L. et al., "Therapy for Open-Angle Glaucoma.," *Consult Pharm*, 33(8), 432-445 (2018), doi:10.4140/TCP.n.2018.432.
Martinez, C.E. et al., "Effect of pupillary dilation on corneal optical aberrations after photorefractive keratectomy," *Arch Ophthalmol*, 116(8), 1053-1062 (1998), doi:10.1001/archopht.116.8.1053.
Marx-Gross, S. et al., "Brimonidine versus dapiprazole: Influence on pupil size at various illumination levels," *Journal of Cataract and Refractive Surgery*,31(7):1372-1376.(2005) doi:10.1016/j.jcrs.2004.12.064.
Matsuura, K. et al., "Determination of pilocarpine in aqueous humour by liquid chromatography—atmospheric pressure chemical ionization mass spectrometry," *Journal of Chromatography B: Biomedical Sciences and Applications*, 621(2):173-180, (1993)doi:10.1016/0378-4347(93)80093-J.
McAuliffe-Curtin, D. and Buckley, C., "Review of alpha adrenoceptor function in the eye," *Eye* 3:472-476 (1989), doi: 10.1038/eye.1989.71.
McDonald, M. et al., "MIRA-3: A 2nd Phase 3 Randomized Placebo-Controlled Trial of Phentolamine Ophthalmic Solution to Reverse Pharmacologically Induced Mydriasis," ASCRS Annual Meeting, Paper ID 81993 (2022).
McDonald, M.B. et al., "Phentolamine mesylate treatment of severe night-vision complaints," Presented at: Annual Meeting of the American Society of Cataract and Refractive Surgery; Mar. 25-29, 2011; San Diego, CA.
McDonald, M.B.et al., "Phentolamine Mesylate Treatment of Severe Night Vision Complaints," AAO Abstracts, PO433 (2010).
McDonnell, P.J. et al., "Associations of presbyopia with vision-targeted health-related quality of life," *Arch Ophthalmol*, 121(11), 1577-1581 (2003), doi:10.1001/archopht.121.11.1577.
McMahon, C.G., "A pilot study of the role of intracavernous injection of vasoactive intestinal peptide (VIP) and phentolamine mesylate in the treatment of erectile dysfunction," *Int J Impot Res.*, 4:233-6 (1996).
Mittag, T.W. et al., "Alpha-adrenergic antagonists: correlation of the effect on intraocular pressure and on alpha 2-adrenergic receptor binding specificity in the rabbit eye," *Exp Eye Res*, 40(4), 591-599 (1985), doi:10.1016/0014-4835(85)90081-8.
Mohammadpour, M. et al., "Updates on Managements for Keratoconus," *J Curr Ophthalmol*, 30(2):110-124 (2018).
Molinari, J.F. et al., "Dapiprazole clinical efficiency for counteracting tropicamide 1%," *Optom Vis Sci*, 71(5), 319-322 (1994), doi:10.1097/00006324-199405000-00003.
Molinari, J.F. et al., in *Optom Vis Sci* (1994) vol. 71(5), p. 319 (Abstract).

Monestam, E. and Lundqvist, B., "Long-time results and associations between subjective visual difficulties with car driving and objective visual function 5 years after cataract surgery," *J Cataract Refract Surg*, 32(1), 50-55. (2006), doi:10.1016/j.jcrs.2005.06.052.
Montes-Mico, R. et al., "Choice of spatial frequency for contrast sensitivity evaluation after corneal refractive surgery," *J. Refract. Surg.*, 17:646-651 (2001).
Montes-Mico, R. et al., "Visual performance with multifocal intraocular lenses: Mesopic contrast sensitivity under distance and near conditions," *Ophthalmology* 111:85-96 (2004).
Moore, C.P. et al., "Anterior Corneal Dystrophy of American Dutch Belted Rabbits: Biomicroscopic and Histopathologic Findings," *Vet. Pathol.*, 24:28-33 (1987).
Moore, P.A. et al., "Pharmacokinetics of lidocaine with epinephrine following local anesthesia reversal with phentolamine mesylate," In *Anesth. Prog.* 55(2);40-48. (2008), DOI: 10.2344/0003-3006(2008)55[40:POLWEF]2.0.CO;2.
Motolko, M.A. and Phelps, C.D., "Contrast sensitivity in asymmetric glaucoma," *Int Ophthalmol.*, 7(1):45-59 (1984).
Nagasubramanian, S.A., "Comparison of the Ocular Hypotensive Efficacy, Safety and Acceptability of Brimonidine 0.2% Twice Daily Versus Pilocarpine 2.0% Thrice Daily as Adjunct Therapy with Beta-Blockers," In: *Glaucoma Update VI. Springer Berlin Heidelberg*, 203-208 (2000), doi:10.1007/978-3-642-57056-8_31.
Nakamura, S. et al., "Evaluation of alpha-1 adrenoceptors in the rabbit iris: pharmacological characterization and expression of mRNA," *Br J Ophthalmol*, 127:1367-1374 (1999). doi:10.1038/sj.bjp.0702675.
National Center for Biotechnology Information (2022). PubChem Compound Summary for CID 517293, Phentolamine, methane sulfonate.
National Center for Biotechnology Information (2022). PubChem Compound Summary for CID 91430, Phentolamine mesylate.
National Institutes of Health. "NIH urges dilated eye exams to detect glaucoma," Accessed Apr. 24, 2020. https://www.nih.gov/news-events/news-releases/nih-urges-dilated-eye-exams-detect-glaucoma.
Neonatal Intensive Care, Children's Hospital, Neonatal Intensive Care Unit, May 26, 2011.
Nielsen, C.B. and Nielsen, P.J., "Effect of alpha- and beta-receptor active drugs on corneal thickness," *Acta Ophthalmol (Copenh)*, 63(3), 351-354 (1985), doi:10.1111/j.1755-3768.1985.tb06819.x.
Noordam, A. et al., "Quantitative Determination of Pilocarpine, Isopilocarpine, Pilocarpic Acid, and Isopilocarpic Acid in Clinical Ophthalmic Pilocarpine Formulations by Reversed-Phase Liquid Chromatography," *Journal of Pharmaceutical Sciences.*, 70(1):96-97 (1981), doi:10.1002/jps.2600700122.
Nyman, N., Optometrist*; Keates, Edwin U. "Physician†. Effects of Dapiprazole on the Reversal of Pharmacologically Induced Mydriasis," *Optometry and Vision Science*: 67(9):705-709 (1990).
Ogura, T. et al., "Properties of [3H]bunazosin binding in rat kidney," *Clin Ther.*, 10(5):559-567 (1988).
OraVerse Summary Basis of Approval (SBA). Clinical pharmacology and biopharmaceutics review. Application No. 22-159; 2007. Novalar. https://www.accessdata.fda.gov/drugsatfda_docs/nda/2008/022159s000_ClinPharmR.
OraVerse, "OraVerse (phentolamine mesylate) FDA Documents injection," Highlights of Prescribing Information. Septodont (2016a).
OraVerse, OraVerse FDA Documents. FDA approves OraVerse for pediatric dental patients 3 years and older. Septodont (2016b).
Oshika, T. et al., "Effect of bunazosin hydrochloride on intraocular pressure and aqueous humor dynamics in normotensive human eyes," *Arch Ophthalmol*, 109(11), 1569-1574, (1991). doi:10.1001/archopht.1991.01080110105046.
Oshika, T. et al., "Incidence of intraoperative floppy iris syndrome in patients on either systemic or topical alpha(1)-adrenoceptor antagonist," *Am. J. Ophthalmol.* 143, 150-151 (2007).
Owsley, C. and Sloane, M.E., "Contrast sensitivity, acuity, and the perception of 'real-world' targets," *Brit J Ophthalmology.*, 71:791-796 (1987).
Owsley, C., "Contrast Sensitivity," *Ophthalmol Clin N Am*, 16:171-177 (2003).

(56) References Cited

OTHER PUBLICATIONS

Padma-Nathan, H. et al., "Long-term safety and efficacy of oral phentolamine mesylate (Vasomax) in men with mild to moderate erectile dysfunction," *Int J Impot Res*, 14(4), 266-270 (2002), doi:10.1038/sj.ijir.3900885.

Park, S.Y. et al., "Clinical Efficacy of Pinhole Soft Contact Lenses for the Correction of Presbyopia," *Semin Ophthalmol*, 34(2), 06-114 (2019), doi:10.1080/08820538.2019.1586966.

Pepose, J. (2021c), "Phase 2 Clinical Trial To Evaluate The Efficacy Of Phentolamine Ophthalmic Solution And Low-Dose Pilocarpine For The Treatment Of Presbyopia," AAO Annual Meeting. Abstract ID 30068457.

Pepose, J. et al. (2022a), "Phentolamine Ophthalmic Solution as a Single Agent Improves Distance-Corrected Near Visual Acuity in Patients with Presbyopia, " ASCRS Annual Meeting, Paper ID 80665.

Pepose, J. et al. (2022b), "VEGA-1: Phentolamine Ophthalmic Solution in combination with Low Dose Pilocarpine Improves Distance-Corrected Intermediate Visual Acuity in Patients with Presbyopia," ARVO Annual Meeting, Abstract ID 3707817.

Pepose, J., et al., "A randomized phase 2 clinical trial of phentolamine mesylate eye drops in patients with severe night vision disturbances," *BMC Ophthalmol*. Oct 8;22(1):402, 2022, doi:10.1186/s12886-022-02621-6.

Pepose, J.P. et al., "Phentolamine mesylate ophthalmic solution provides long lasting pupil modulation and improves visual acuity," The Association for Research in Vision and Ophthalmology Meeting (2020).

Pepose, J.S et al., "Phentolamine mesylate ophthalmic solution provides lasting pupil modulation and improves near visual acuity in presbyopic glaucoma patients in a randomized phase 2b clinical trial," *Clin Ophthalmol*. 15:79-91 (2020) doi: 10.2147/OPTH. S278169. eCollection 2021.

Pepose, J.S., et al. (2021b) "Phase 2 Clinical Trial to Evaluate the Efficacy of Phentolamine Ophthalmic Solution and Low-Dose Pilocarpine for the Treatment of Presbyopia. Paper #76645," The American Society of Cataract and Refractive Surgery Meeting.

Pepose, J.S.et al., (2021a). "Phase 3 clinical trial to evaluate the efficacy of phentolamine ophthalmic solution on the reversal of pharmacologically induced mydriasis Paper #76599," The American Society of Cataract and Refractive Surgery Meeting.

Peter, J.V.S. et al., "Pharmacokinetics of Pilocarpine in Subjects with Varying Degrees of Renal Function," *Journal of Clinical Pharmacology*, 40(12 Pt 2):1470-1475 (2000).

Pop, M. and Payette, Y., "Risk factors for night vision complaints after LASIK for myopia," *Ophthalmology*, 111(1), 3-10 (2004), doi:10.1016/j.ophtha.2003.09.022.

Poulet, F.M. et al., "Development of hibernomas in rats dosed with phentolamine mesylate during the 24-month carcinogenicity study," *Toxicol Pathol*, 32(5), 558-566 (2004), doi:10.1080/01926230490505086.

Prata, T.S. et al., "Iris morphologic changes related to alpha (1) adrenergic receptor antagonists: implications for intraoperative floppy iris syndrome," *Ophthalmology*, 116:877-81 (2009).

Puell, M.C. et al., "Mesopic contrast sensitivity in the presence or absence of glare in a large driver population," *Graefes Arch Clin Exp Ophthalmol*, 242(9), 755-761 (2004) doi:10.1007/s00417-004-0951-6.

Radi, Z. et al., "Comparative pathophysiology, toxicology, and human cancer risk assessment of pharmaceutical-induced hibernoma," *Toxicol Appl Pharmacol*, 273(3), 456-463 (2013), doi:10.1016/j.taap.2013.10.011.

Rahman, M.Q. et al., "Brimonidine for glaucoma," *Expert Opinion on Drug Safety*;9(3):483-491 (2010), doi:10.1517/14740331003709736.

Regan, D. et al., "Visual acuity and contrast sensitivity in multiple sclerosis—hidden visual loss: an auxiliary diagnostic test," *Brain.*, 100(3):563-79 (1977).

Regitine, Novartis Pharmaceuticals Corporation, "Regitine—phentolamine mesylate injection, powder, lyophilized, for suspension; labeling," (1998).

Regitine, Regitine FDA Documents. Highlights of Prescribing Information (1998).

Rengstorff, R.H. and Doughty, C. B., "Mydriatic and cycloplegic drugs: a review of ocular and systemic complications," *Am J Optom Physiol Opt*, 59(2), 162-177 (1982).

Rev-Eyes Ophthalmic Eyedrops 0.5% (Bausch & Lomb), *Drug Reference Encyclopedia*.

REV-EYES. Federal Register; 78(92):27971, "Determination that REV-EYES (dapiprazole hydrochloride ophthalmic solution), 0.5%, was not withdrawn from sale for reasons of safety or effectiveness," (2013).

Rev-Eyes® dapiprazole hydrochloride ophthalmic solution 0.5%. NDA 019849, Dec. 31, 1990.

Rhopressa, Rhopressa pharmacology/toxicology NDA review and evaluation. *United States Food and Drug Administration* (2017).

Richards, D.A. et al., "Circulatory and alpha-adrenoceptor blocking effects of phentolamine," *Br J Clin Pharmacol* 5(6):507-513 (1978), doi: 10.1111/j.1365-2125.1978.tb01665.

Ridder, W.H. et al., "Contrast Sensitivity and Tear Layer Aberrometry in Dry Eye Patients," *Optometry and Vision Sciences*, 86:E1059-1068 (2009).

Robin, A.L. et al., "Adherence in glaucoma: objective measurements of once-daily and adjunctive medication use," *Am J Ophthalmol*, 144(4), 533-540 (2007), doi:10.1016/j.ajo.2007.06.012.

Romero-Jimenez, M. et al., "Keratoconus: a review," *Cont Lens Anterior Eye*, 33(4), 57-166; quiz 205, (2010)doi:10.1016/j.clae.2010.04.006.

Rosen, Emanuel S., "FRCSE Night vision disturbance," *Journal of Cataract & Refractive Surgery.*, 31(2):247-9 (2005).

Rutherford, B. et al., "Local and systemic toxicity of intraoral submucosal injections of phentolamine mesylate (OraVerse)," *Anesth Prog*, 56(4), 123-127 (2009), doi:10.2344/0003-3006-56.4.123.

Rutkowski, P.C. and Thompson, H.S., "Mydriasis and Increased Intraocular Pressure," *Arch Ophthalmol.* 87(1 ):21-24 (1972).

Sandoval, H.P. et al., "Comparison of visual outcomes, photopic contrast sensitivity, wavefront analysis, and patient satisfaction following cataract extraction and IOL implantation," *Eye*, 22:1469-1475 (2008).

Schallhorn, et al., "Comparison of night driving performance after wavefront-guided and conventional LASIK for moderate myopia," *Ophthalmology*, 116(4), 702-709 (2009), doi:10.1016/j.ophtha.2008.12.038.

Septodont Holding (2016): Approved Product Labeling for ORAVERSE (phentolamine mesylate; 0.4mg/1.7mL) for injection. NDA 022159, Mar. 2016. Available online at https://www.accessdata.fda.gov/drugsatfda_docs/label/2016/022159s011lbl.pdf, checked on Apr. 27, 2022.

Serle, J.B. et al., "Two Phase 3 Clinical Trials Comparing the Safety and Efficacy of Netarsudil to Timolol in Patients With Elevated Intraocular Pressure: Rho Kinase Elevated IOP Treatment Trial 1 and 2 (ROCKET-1 and ROCKET-2)," *Am J Ophthalmol.*, 186:116-27 (2017).

Shah, B. et al., "Influence of thymoxamine eye-drops on the mydriatic effect of tropicamide and phenylephrine alone and in combination," *Ophthalmic Physiol Opt*, 9(2), 153-155 (1989), doi:10.1111/j.1475-1313.1989.tb00835.

Shemesh, G. et al., "Effect of brimonidine tartrate 0.10% ophthalmic solution on pupil diameter," *Journal of Cataract and Refractive Surgery*, 37(3):486-489 (2011), doi:10.1016/j.jers.2010.09.026.

Sherwood, M.B. et al., "Twice-Daily 0.2% Brimonidine-0.5% Timolol Fixed-Combination Therapy vs Monotherapy With Timolol or Brimonidine in Patients With Glaucoma or Ocular Hypertension," *Arch. Ophthalmol.* 124, 1230 (2006).

Shiau, T. et al., "The role of episcleral venous pressure in glaucoma associated with Sturge-Weber syndrome," *J AAPOS*, 16(1), 61-64 (2012), doi:10.1016/j.jaapos.2011.09.014.

Shiose, Y. et al., "Epidemiology of glaucoma in Japan—a nationwide glaucoma survey," *Jpn J Ophthalmol*, 35(2), 133-155 (1991).

Silva, L.F.G. et al., "Phentolamine bioequivalence study," *In Int. J Clin. Pharmacol. Ther* 42 (1), pp. 43-49 (2004).

Sioufi, A. et al., "Gas chromatographic determination of phentolamine (Regitine®) in Human Plasma," *J Chromat* 222429-435 (1981), doi: 10.1016/s0378-4347(00)84143-2.

(56) References Cited

OTHER PUBLICATIONS

Sommer, A. et al., "Relationship between intraocular pressure and primary open angle glaucoma among white and black Americans," The Baltimore Eye Survey. *Arch Ophthalmol*, 109(8), 1090-1095 (1991), doi:10.1001/archopht.1991.01080080050026.

Steiner, T.F., "State of independent optometry: optometry dominates primary eyecare," *Review of Optometric Business* (2013).

Steinhauer, S.R. et al., "Sympathetic and parasympathetic innervation of pupillary dilation during sustained processing," *Int J Psychophysiol*, 52(1), 77-86 (2004), doi:10.1016/j.ijpsycho.2003.12.005.

Sternitzke, K.D. et al., "High-performance liquid chromatographic determination of pilocarpitie hydrochloride and its degradation products using a /I-cyclodextrin column," *Journal of Chromatography*, 0(589):159-164 (1992), doi:10.1016/0021-9673(92)80017.

Suzuki, F. et al., "Distribution of alpha-1 adrenoceptor subtypes in RNA and protein in rabbit eyes," *Br J Ophthalmol*, 135:600-608 (2002), doi: 10.1038/sj.bjp.0704503.

Takayanagi, I. et al., "Alpha 1B-adrenoceptor mechanisms in rabbit iris dilator." *Jpn J Pharmacol*, 59(3), 301-305 (1992), doi:10.1254/jjp.59.301.

Tang, W. et al., "Visual performance of lasik patients," *Ann Acad Med Singapore*, 35:541-6 (2006).

Tanzer, J.M. et al., "A Pharmacokinetic and Pharmacodynamic Study of Intravenous Pilocarpine in Humans," *J Dent Res.* 74(12):1845-1849 (1995), doi:10.1177/00220345950740120701.

Taylor, S.H. et al., "The circulatory effects of phentolamine in man," *Circulation*, 31:741-754 (1965), doi: 10.1161/01.cir.31.5.741.

Tham, Y. C. et al., "Global prevalence of glauco ma and projections of glaucoma burden through 2040: a systematic review and meta-analysis," *Ophthalmology*, 121(11), 2081-2090 (2014), doi:10.1016/j.ophtha.2014.05.013.

Thomas, J., "Normal and amblyopic contrast sensitivity functions in central and peripheral retinas," *Invest. Ophthalmol Visual Sci.* 17:746-753 (1978).

Thordsen, J.E. et al., "Miotic effect of brimonidine tartrate 0.15% ophthalmic solution in normal eyes," *Journal of Cataract and Refractive Surgery*, 30(8):1702-1706 (2004), doi:10.1016/j.jcrs.2003.12.037.

Trew, D. R. et al., "Ocular responses in healthy subjects to topical bunazosin 0.3%—an alpha 1-adrenoceptor antagonist," *Br J Ophthalmol*, 75(7), 411-413 (1991), doi:10.1136/bjo.75.7.411.

Karanfil et al., "Update on Presbyopia-correcting Drops", European Ophthalmic Review, 2017, 11(2):99-102.

Suzuki, Koutaro, [In what cases are mydriatics used? types of mydriatics and dilated eye exams] Donnatoki, Sandosuruno? sandoyaku no shurui to sando no hitsuyona kensa (in Japanese), [The Japanese Journal of Ophthalmic Caring] Ganka care (in Japanese), 2006, 8(7):586-589.

Web Archives of the World | Web Archiving Project by National Diet Library, [online], Sep. 15, 2016, [searched on Aug. 30, 2023], Internet <URL: https://web.archive.org/web/20160915211443/https://www.jacd.info/method/ganteikensa.htm>, 7 pages.

Dungan et al., "Amidephrine—I: Pharmacologic Characterization of a Sympathomimetic Alkylsulfonamidophenethanolamine", Int J Neuropharmacol., Jul. 1965, 4:219-234.

Korczyn et al., "The effect of L-dopa on pupillary diameter in mice", Experientia, Apr. 1982, 38(4):481-482.

Presbyopia (year 2011)—Internet publication—https://web.archive.org/web/20111019203251/https://excimerclinic.ru/long-sight/presbiopy.

Midriasis (year 2014)—LookMedBook—Internet publication—https://web.archive.org/web/20140209222614/ https://lookmedbook.ru/disease/midriaz.

METHODS AND COMPOSITIONS FOR TREATMENT OF PRESBYOPIA, MYDRIASIS, AND OTHER OCULAR DISORDERS

CROSS-REFERENCE TO RELATED APPLICATIONS

This application is a continuation of U.S. patent application Ser. No. 17/230,270, filed Apr. 14, 2021, which is a continuation of U.S. patent application Ser. No. 16/841,026, filed Apr. 6, 2020, now U.S. Pat. No. 10,993,932, which is a continuation of international patent application no. PCT/US2019/058182, filed Oct. 25, 2019, which claims the benefit of and priority to U.S. Provisional Patent Application Ser. No. 62/751,391, filed Oct. 26, 2018; the contents of each of which are hereby incorporated by reference in their entirety.

FIELD OF THE INVENTION

The invention provides methods, compositions, and kits containing an alpha-adrenergic antagonist, such as phentolamine, for use in monotherapy or as part of a combination therapy to treat patients suffering from presbyopia, mydriasis, and/or other ocular disorders.

BACKGROUND

Presbyopia is a disorder of the eye associated with aging that results in the inability to focus on nearby objects. Presbyopia is generally caused by a hardening of the eye's lens, which reduces its ability to flex. People often first notice the effects of presbyopia around 40 years of age, with the effects becoming increasingly more pronounced over the following two decades. The effects of presbyopia can have a significant negative impact on quality of life, for example, interfering with activities involving reading.

Existing treatments for presbyopia are not effective for all patients and/or have undesirable characteristics. A common treatment for presbyopia is the use of corrective lenses (for example, reading glasses or bifocals), which must then be carried by the patient. Additionally, bifocal or multifocal lenses, including contact lenses, can be difficult to use, particularly when undertaking tasks requiring frequent changes between viewing near and far objects. Monovision treatment approaches, where one eye is optimized for distance vision and lenses or surgical methods compensate for presbyopia in the other eye, result in impaired depth perception and can be disorienting. Surgical approaches, such as LASIK and corneal inlays, also present all the risks inherent to surgical procedures. Despite ongoing research, there are currently no non-invasive, pharmacological treatments for presbyopia that have been approved as safe and effective by the U.S. Food and Drug Administration.

Mydriasis is a disorder of the eye characterized by an unusually dilated pupil, frequently caused by one or more of disease, trauma, or a pharmacological agent. The pharmacological agent could be, for example, an agent administered to the eye to cause pupil dilation as part of an eye examination. Alternatively, the pharmacological agent could be an agent administered to the patient for other reasons, and may be a single administration of the agent to the patient or an agent administered on multiple occasions. The negative effects of mydriasis can include sensitivity to light and inability to focus, particularly in bright environments. Existing treatments for mydriasis vary, based on the cause of the mydriasis, but are not effective for all patients and/or have undesirable characteristics. One treatment for mydriasis described in the literature is REV-EYES™ (dapiprazole hydrochloride ophthalmic solution). A typical administration protocol for REV-EYES™ is to administer two drops of the ophthalmic solution to the patient's eye and then after five minutes administer an additional two drops of the ophthalmic solution to the patient's eye. Some drawbacks of REV-EYES™ are that it has been reported to cause a significant burning sensation upon administration, which is unpleasant for the patient, as well as significant eye redness. The need exists for better treatments for mydriasis.

The present invention addresses the aforementioned need for methods and compositions for treating patients suffering from presbyopia, mydriasis, and other ocular disorders while minimizing undesirable side effects, and the invention provides other related advantages.

SUMMARY

The invention provides methods, compositions, and kits containing an alpha-adrenergic antagonist, such as phentolamine, for use in monotherapy or as part of a combination therapy to treat patients suffering from presbyopia, mydriasis, and/or other ocular disorders. The alpha-adrenergic antagonist, such as phentolamine, is administered topically to the eye of the patient, preferably in the form of a liquid aqueous ophthalmic formulation. Desirably the alpha-adrenergic antagonist is administered to the patient once daily, alone or in combination with an additional agent, in order to reduce pupil diameter of the patient, such as to have a pupil diameter of less than 2 mm, 1.8 mm, or 1.6 mm, or to have a pupil diameter reduction of at least 1 mm, 2 mm, 3 mm, or more. In certain embodiments, the alpha-adrenergic antagonist is administered to the patient once daily, alone or in combination with an additional agent, in order to reduce pupil diameter of the patient, such as to have a pupil diameter of less than 3.0, 2.8, 2.6, 2.4, or 2.2 mm. Such reduction in pupil diameter due to the alpha-adrenergic antagonist provides therapeutic benefits to patients suffering from presbyopia or mydriasis. The reduction in pupil diameter may be characterized according to the percent reduction in pupil diameter due to administering the alpha-adrenergic antagonist, such as where the reduction in pupil diameter is at least 5%, 10%, 15%, 20%, 30%, or 40%. One benefit of therapeutic methods described herein is that the patient may experience an improvement in visual performance, for example, an improvement in the patient's ability to see clearly and/or ability to distinguish between an object and its background. The improvement in visual performance may include improvement in visual performance at near distance and at far distance. Another benefit of therapeutic methods described herein is that there are methods providing a once daily administration protocol, which is easier for patients than a dosing protocol that requires administration of therapeutic agent(s) multiple times per day. Yet another benefit of therapeutic methods described herein is that there are methods providing for rapid onset of treatment, where, for example, therapeutic benefits can be observed as early as within about 30 minutes after administering, for example, an alpha-adrenergic antagonist such as phentolamine to an eye of the patient. In certain embodiments, the therapeutic benefits can be observed within 30 to 60 minutes after administering, for example, an alpha-adrenergic antagonist such as phentolamine to an eye of the patient. In certain embodiments, the therapeutic benefits can be observed as early as within about 1 hour after administering, for example, an alpha-adrenergic antagonist such as phentolamine to an eye of the patient. Exemplary aspects and embodiments of the invention are described below.

One aspect of the invention provides a method of treating presbyopia in a patient. The method comprises administering to an eye of a patient in need thereof a dosage of an alpha-adrenergic antagonist in an amount effective to thereby treat the presbyopia, wherein the dosage is administered to the eye no more than once per day. The dosage may be administered at or near the bedtime of the patient. One benefit of such a dosing protocol is that it minimizes eye redness experienced by the patient during the patient's waking hours, while achieving a reduction in pupil diameter that is desirable for treatment of presbyopia. In certain embodiments, the dosage contains phentolamine mesylate.

Another aspect of the invention provides a method of treating presbyopia in a patient while minimizing eye redness during the patient's waking hours. The method comprises administering to an eye of a patient in need thereof only at or near the bedtime of the patient a dosage of an alpha-adrenergic antagonist in an amount effective to thereby treat the presbyopia. One benefit of the dosing protocol is that it minimizes eye redness experienced by the patient during the patient's waking hours, while achieving a reduction in pupil diameter that is desirable for treatment of presbyopia. In certain embodiments, the dosage contains phentolamine mesylate. In certain embodiments, the method further comprises administering to said eye of the patient an additional agent that facilitates reduction of the patient's pupil or improves visual performance. In certain embodiments, the method further comprises administering to said eye of the patient an additional agent that facilitates reduction of the patient's pupil. In certain embodiments, the method further comprises administering to said eye of the patient an additional agent that improves visual performance. In other embodiments, the alpha-adrenergic antagonist is the only agent administered that treats presbyopia.

Another aspect of the invention provides a method of treating presbyopia in a patient according to a monotherapy treatment regimen. The method comprises administering to an eye of a patient in need thereof a dosage of a single therapeutic agent in an amount effective for treatment of presbyopia, wherein the single therapeutic agent is an alpha-adrenergic antagonist. The dosage may be administered to the eye of the patient according to a particular dosing protocol, such as administration to the eye of the patient once per day, which may be, for example, at or near the bed time of the patient. Such dosing protocol may entail, for example, administering the dosage to the eye of the patient for at least three or seven consecutive days. In certain embodiments, the single therapeutic agent is phentolamine mesylate.

Another aspect of the invention provides a method of treating mydriasis in a patient. The method comprises administering to an eye of a patient in need thereof a dosage of an alpha-adrenergic antagonist in an amount effective to thereby treat the mydriasis. In certain embodiments, the mydriasis is due to the patient having received one or more of an adrenergic or parasympatholyic agent. In certain embodiments, the mydriasis is due to the patient having received one or more of an alpha agonist, a TAAR1 agonist, or NSAID. In certain embodiments, the mydriasis is due to the patient having received one or more of atropine, cyclopentolate, homatropine, scopolamine, tropicamide, phenylephrine, or a pharmaceutically acceptable salt thereof. In certain embodiments, the mydriasis is due to the patient having received one or more of atropine, cyclopentolate, homatropine, scopolamine, tropicamide, or a pharmaceutically acceptable salt thereof. In certain embodiments, the mydriasis is due to the patient having received one or more of atropine, cyclopentolate, homatropine, scopolamine, tropicamide, flubiprofen, suprofen, hydroxyamphetamine, phenylephrine, cyclopentolate, ketorolac, or a pharmaceutically acceptable salt thereof. In certain embodiments, the single therapeutic agent is phentolamine mesylate.

The invention also provides for reducing eye redness due to administration of the alpha-adrenergic antagonist. In certain embodiments, the method further comprises administering an agent that reduces eye redness. Exemplary agents that reduce eye redness include brimonidine, tetrahydrozoline, oxymetazoline, naphthazoline, or a pharmaceutically acceptable salt thereof, such as LUMIFY® (which is a commercially available ophthalmic solution containing brimonidine tartrate (0.025% w/w)).

Another aspect of the invention provides a pharmaceutical composition comprising an alpha-adrenergic antagonist and a second therapeutic agent selected from the group consisting of a muscarinic acetylcholine receptor agonist, an alpha-2 adrenergic agonist, a prostaglandin, and a lipoic acid choline ester. Preferably, the pharmaceutical composition is formulated for ophthalmic administration.

DETAILED DESCRIPTION OF THE INVENTION

Figure 1:
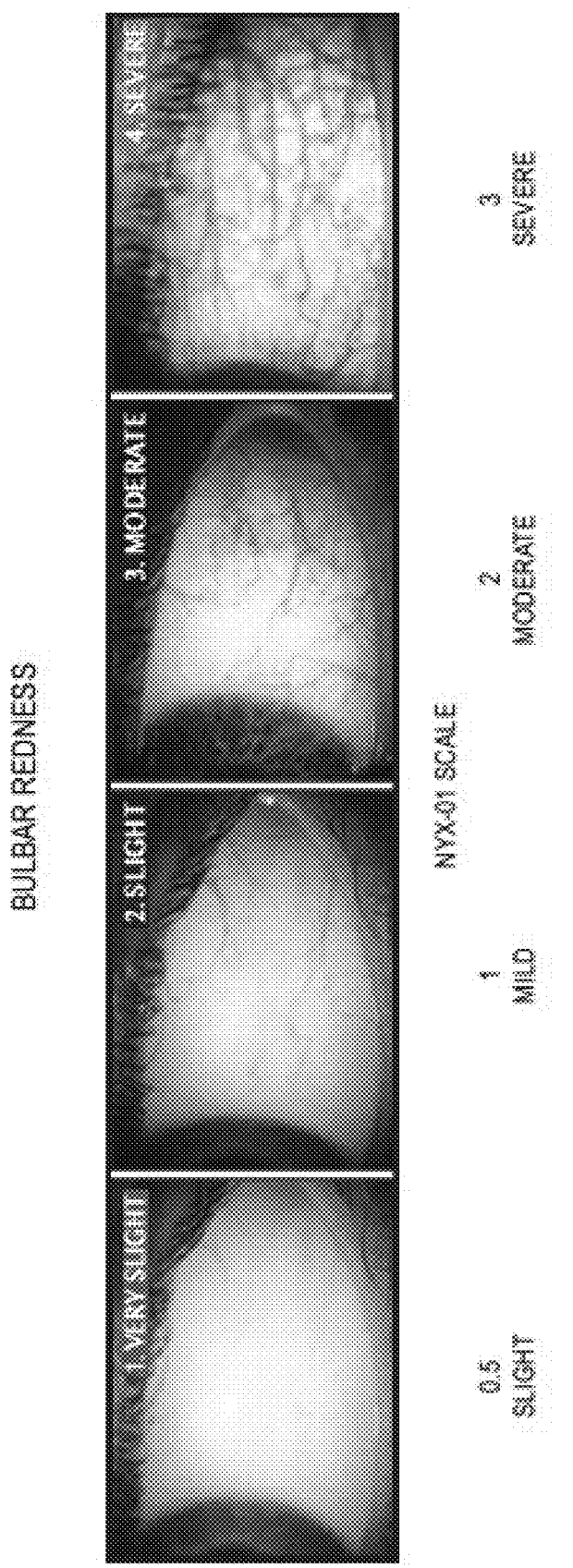
FIG. 1 depicts exemplary eye redness as measured according to (1) the CCLRU Redness Grading Scale, and (2) the NYX-001 Redness Grading Scale.

The invention provides methods, compositions, and kits containing an alpha-adrenergic antagonist, such as phentolamine, for use in monotherapy or as part of a combination therapy to treat patients suffering from presbyopia, mydriasis, and/or other ocular disorders. The alpha-adrenergic antagonist, such as phentolamine, is administered topically to the eye of the patient, preferably in the form of a liquid aqueous ophthalmic formulation. Desirably the alpha-adrenergic antagonist is administered to the patient once daily, alone or in combination with an additional agent, in order to reduce pupil diameter of the patient, such as to have a pupil diameter of less than 2 mm, 1.8 mm, or 1.6 mm, or to have a pupil diameter reduction of at least 1 mm, 2 mm, 3 mm, or more. In certain embodiments, the alpha-adrenergic antagonist is administered to the patient once daily, alone or in combination with an additional agent, in order to reduce pupil diameter of the patient, such as to have a pupil diameter of less than 3.0, 2.8, 2.6, 2.4, or 2.2 mm. The reduction in pupil diameter may be characterized according to the percent reduction in pupil diameter due to administering the alpha-adrenergic antagonist, such as where the reduction in pupil diameter is at least 5%, 10%, 15%, 20%, 30%, or 40%. Such reduction in pupil diameter due to the alpha-adrenergic antagonist provides therapeutic benefits to patients suffering from presbyopia or mydriasis. One benefit of therapeutic methods described herein is that the patient may experience an improvement in visual performance, for example, an improvement in the patient's ability to see clearly and/or ability to distinguish between an object and its background. The improvement in visual performance may include improvement in visual performance at near distance and at far distance. Another benefit of therapeutic methods described herein is that there are methods providing a once daily administration protocol, which is easier for patients than a dosing protocol that requires administration of therapeutic agent(s) multiple times per day. Yet another benefit of therapeutic methods described herein is that there are methods providing for rapid onset of treatment, where, for example, therapeutic benefits can be observed as early as within about 30 minutes after administering, for example, an alpha-adrenergic antagonist such as phentolamine to an eye of the patient. In certain embodiments, the therapeutic benefits can be observed within 30 to 60 minutes after administering, for example, an alpha-adrenergic antagonist such as phentolamine to an eye of the patient. In certain embodiments, the therapeutic benefits can be observed as early as within about 1 hour after administering, for example, an alpha-adrenergic antagonist such as phentolamine to an eye of the patient. Exemplary aspects and embodiments of the invention are described below. Various aspects of the invention are set forth below in sections; however, aspects of the invention described in one particular section are not to be limited to any particular section.

Definitions

To facilitate an understanding of the present invention, a number of terms and phrases are defined below.

The terms "a," "an" and "the" as used herein mean "one or more" and include the plural unless the context is inappropriate.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. Unless specified otherwise, an effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin in Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_3$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate (mesylate), 2-naphthalenesulfonate, nicotinate, oxalate, palmoate, pectinate, persulfate, phenylpropionate, picrate, pivalate, propionate, succinate, sulfate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "alkanoate" is art-recognized and refers to alkyl-C(O)O—.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

As used herein, the term "EV06" refers to a compound having the following chemical structure:

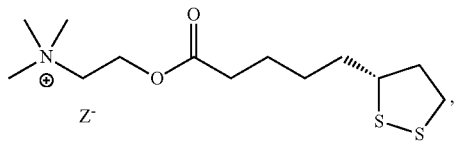 [SMILES: C[N+](C)(C)CCOC(=O)CCCC[C@@H]1CCSS1]

an optical isomer, or a mixture thereof, where Z is an anion. Anion $Z^-$ can be any pharmaceutically acceptable anion. Non-limiting examples of anions include chloride, bromide, iodide, sulfate, methanesulfonate, nitrate, maleate, acetate, citrate, fumarate, hydrogen fumarate, tartrate (e.g., (+)-tartrate, (−)-tartrate, or a mixture thereof), succinate, benzoate, and anions of an amino acid such as glutamic acid. In some embodiments, the anion is chloride. In some embodiments, the anion is tartrate.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Therapeutic Methods

The invention provides methods for treating patients suffering from presbyopia, mydriasis, and/or other ocular disorders by administering to the eye of the patient an alpha-adrenergic antagonist, such as phentolamine. The alpha-adrenergic antagonist is administered topically to the eye of the patient, preferably in the form of a liquid aqueous ophthalmic formulation. Various aspects and embodiments of the therapeutic methods are described in the sections below. The sections are arranged for convenience and information in one section is not to be limited to that section, but may be applied to methods in other sections.

A. First Method

One aspect of the invention provides a method of treating presbyopia in a patient, comprising administering to an eye of a patient in need thereof a dosage of an alpha-adrenergic antagonist in an amount effective to thereby treat the presbyopia, wherein the dosage is administered to the eye no more than once per day.

The method may be further characterized by additional features, such as the dosing regimen and the identity of the dosage, as described in more detail below. The invention embraces all permutations and combinations of these features. For example, in certain embodiments, the dosage is administered at or near the bedtime of the patient. In certain embodiments, the dosage is administered within 1 hour of the patient's bedtime.

In certain embodiments, the dosage comprises a pharmaceutically acceptable salt of phentolamine. In certain embodiments, the dosage comprises phentolamine mesylate.

B. Second Method

Another aspect of the invention provides a method of treating presbyopia in a patient while minimizing eye redness during the patient's waking hours, comprising administering to an eye of a patient in need thereof only at or near the bedtime of the patient a dosage of an alpha-adrenergic antagonist in an amount effective to thereby treat the presbyopia.

The method may be further characterized by additional features, such as the dosing regimen and the administration, identity, and amount of an additional agent, as described in more detail below. The invention embraces all permutations and combinations of these features. For example, in certain embodiments, the dosage is administered to the eye no more than once per day. In certain embodiments, the dosage comprises a pharmaceutically acceptable salt of phentolamine. In certain embodiments, the dosage comprises phentolamine mesylate.

C. Third Method

Another aspect of the invention provides a method of treating presbyopia in a patient, comprising administering to an eye of a patient in need thereof a dosage of an alpha-adrenergic antagonist in an amount effective to thereby treat the presbyopia.

The method may be further characterized by additional features, such as the dosing regimen and the administration, identity, and amount of an additional agent, as described in more detail below. The invention embraces all permutations and combinations of these features.

In certain embodiments, the dosage is administered to the patient daily. In certain embodiments, the dosage is administered to the patient twice per day. In certain embodiments, the dosage comprises a pharmaceutically acceptable salt of phentolamine. In certain embodiments, the dosage comprises phentolamine mesylate.

In certain embodiments, the dosage of alpha-adrenergic antagonist is 1% w/w phentolamine mesylate solution. In certain embodiments, the dosage of alpha-adrenergic antagonist is 1.5% w/w phentolamine mesylate solution. In certain embodiments, the dosage of alpha-adrenergic antagonist is 2% w/w phentolamine mesylate solution.

In certain embodiments, the dosage is administered as a single eye drop. In certain embodiments, the dosage is administered as two eye drops.

In certain embodiments, the dosage is administered to the patient as a fixed dose combination with an additional therapeutic agent. In certain embodiments, the additional therapeutic agent is pilocarpine.

D. Additional Features of the First, Second, and Third Therapeutic Methods

The First, Second, and Third Therapeutic Methods may be further characterized according additional features. One feature is whether an additional agent is administered (e.g., an agent that facilitates reduction of the patient's pupil or improves visual performance). Another feature is whether the dosage of alpha-adrenergic antagonist is administered sequentially or concurrently with an additional agent.

In certain embodiments, the method further comprises administering to said eye of the patient an additional agent that facilitates reduction of the patient's pupil or improvement in visual performance. In certain embodiments, the method further comprises administering to said eye of the patient an additional agent that facilitates reduction of the patient's pupil. This desirably results in further reduction in the patient's pupil diameter beyond that achieved when administering just the alpha-adrenergic antagonist. In certain embodiments, the method further comprises administering to said eye of the patient an additional agent that facilitates improvement in visual performance.

In certain embodiments, the additional agent is administered to said eye of the patient concurrently with the dosage of alpha-adrenergic antagonist. In certain embodiments, the additional agent is administered to said eye of the patient sequentially either before or after administering to said eye of the patient the dosage of alpha-adrenergic antagonist.

The method may be further characterized according to the amount of additional agent administered to an eye of the patient. For example, in certain embodiments, the additional agent is administered to the eye of the patient in an amount ranging from about 0.0001 mg to about 0.001 mg. In certain embodiments, the additional agent is administered to the eye of the patient in an amount ranging from about 0.001 mg to about 0.01 mg. In certain embodiments, the additional agent is administered to the eye of the patient in an amount ranging from about 0.01 mg to about 0.1 mg. In certain embodiments, the additional agent is administered to the eye of the patient in an amount ranging from about 0.1 mg to about 0.5 mg. In certain embodiments, the additional agent is administered to the eye of the patient in an amount ranging from about 0.5 mg to about 1.0 mg. In certain embodiments, the additional agent is administered to the eye of the patient in an amount ranging from about 1.0 mg to about 1.5 mg. In certain embodiments, the additional agent is administered to the eye of the patient in an amount ranging from about 1.5 mg to about 2.0 mg. In certain embodiments, the additional agent is administered to the eye of the patient in an amount ranging from about 2.0 mg to about 2.5 mg. In certain embodiments, the additional agent is administered to the eye of the patient in an amount ranging from about 2.5 mg to about 3.0 mg. In certain embodiments, the additional agent is administered to the eye of the patient in an amount ranging from about 2.5 mg to about 3.0 mg. In certain embodiments, the additional agent is administered to the eye of the patient in an amount ranging from about 0.001 mg to about 0.1 mg. In certain embodiments, the additional agent is administered to the eye of the patient in an amount ranging from about 0.1 mg to about 1.0 mg. In certain embodiments, the additional agent is administered to the eye of the patient in an amount ranging from about 1.0 mg to about 2.0 mg. In certain embodiments, the additional agent is administered to the eye of the patient in an amount ranging from about 0.1 mg to about 0.125 mg. In certain embodiments, the additional agent is administered to the eye of the patient in an amount ranging from about 0.125 mg to about 0.25 mg. In certain embodiments, the additional agent is administered to the eye of the patient in an amount ranging from about 0.25 mg to about 0.50 mg. In certain embodiments, the additional agent is administered to the eye of the patient in an amount ranging from about 0.50 mg to about 0.75 mg. In certain embodiments, the additional agent is administered to the eye of the patient in an amount ranging from about 0.75 mg to about 1.0 mg. In certain embodiments, the additional agent is administered to the eye of the patient in an amount ranging from about 1.25 mg to about 1.5 mg.

The method may be further characterized according to the identity of the additional agent. In certain embodiments, the additional agent improves visual performance. In certain embodiments, the additional agent facilitates reduction of the patient's pupil. In certain embodiments, the additional agent is selected from the group consisting of a muscarinic acetylcholine receptor agonist, an alpha-2 adrenergic agonist, a prostaglandin, and a lipoic acid choline ester.

In certain embodiments, the additional agent is a muscarinic acetylcholine receptor agonist.

In certain embodiments, the additional agent is pilocarpine or a pharmaceutically acceptable salt thereof. In certain embodiments, the additional agent is pilocarpine hydrochloride. In certain embodiments, the additional agent is administered to the eye of the patient in an amount ranging from about 0.1 mg to about 1.0 mg. In certain embodiments, the additional agent is administered to the eye of the patient in an amount ranging from about 0.1 mg to about 0.3 mg. In certain embodiments, the additional agent is administered to the eye of the patient in an amount of about 0.2 mg. In certain other embodiments, the additional agent is administered to the eye of the patient in an amount ranging from about 0.3 mg to about 0.6 mg.

In certain embodiments, the additional agent is pilocarpine or a pharmaceutically acceptable salt thereof, which is administered to the patient in the form of an ophthalmic solution. In certain embodiments, the ophthalmic solution contains pilocarpine or pharmaceutically acceptable salt thereof in the amount of from about 0.1% w/w to about 3% w/w. In certain embodiments, the ophthalmic solution contains pilocarpine or pharmaceutically acceptable salt thereof in the amount of from about 0.2% w/w to about 0.4% w/w. In certain embodiments, the ophthalmic solution contains pilocarpine or pharmaceutically acceptable salt thereof in the amount of from about 1% w/w to about 2% w/w. In certain embodiments, the one drop of the ophthalmic solution containing pilocarpine or pharmaceutically acceptable salt is administered to the patient's eye.

In certain embodiments, one drop of an ocular formulation is administered to an eye of the patient, wherein the ocular formulation comprises pilocarpine in an amount ranging from about 0.001% to about 0.1% w/w, about 0.001% to about 2% w/w, about 0.01% to about 2% w/w, or about 0.01% to about 4% w/w. In certain embodiments, one drop of an ocular formulation is administered to an eye of the patient, wherein the ocular formulation comprises pilocarpine in an amount of about 0.01%, 0.25%, 0.5%, 1%, 2%, or 4% w/w.

In certain embodiments, the additional agent is carbachol or a pharmaceutically acceptable salt thereof. In certain embodiments, the additional agent is carbachol. In certain embodiments, the additional agent is administered to the eye of the patient in an amount ranging from about 0.5 mg to about 2.5 mg. In certain embodiments, the additional agent is administered to the eye of the patient in an amount ranging from about 0.5 mg to about 1.0 mg. In certain other embodiments, the additional agent is administered to the eye of the patient in an amount ranging from about 1.0 mg to about 1.5 mg. In certain embodiments, the additional agent is administered to the eye of the patient in an amount of about 1.2 mg.

In certain embodiments, one drop of an ocular formulation is administered to an eye of the patient, wherein the ocular formulation comprises carbochol in an amount ranging from about 0.001% to about 0.1% w/w, about 0.001% to about 3% w/w, about 0.1% to about 1.5% w/w, or about 0.1% to about 2% w/w. In certain embodiments, one drop of an ocular formulation is administered to an eye of the patient, wherein the ocular formulation comprises carbochol in an amount of about 0.1%, 0.25%, 0.5%, 0.75, 1.5%, 2%, 2.25%, or 3% w/w.

In certain embodiments, the additional agent is bethanechol or a pharmaceutically acceptable salt thereof. In certain embodiments, the additional agent is a bethanechol salt. In certain embodiments, the additional agent is bethanechol chloride. In certain embodiments, the additional agent is administered to the eye of the patient in an amount ranging from about 0.1 mg to about 3 mg. In certain embodiments, the additional agent is administered to the eye of the patient in an amount ranging from about 0.1 mg to about 1 mg. In certain other embodiments, the additional agent is administered to the eye of the patient in an amount ranging from about 1 mg to about 2 mg. In certain embodiments, the additional agent is administered to the eye of the patient in an amount of about 1.2 mg.

In certain embodiments, one drop of an ocular formulation is administered to an eye of the patient, wherein the ocular formulation comprises bethanechol chloride in an amount ranging from about 0.001% to about 0.1% w/w, about 0.001% to about 0.01% w/w, or about 0.01% to about 0.1% w/w. In certain embodiments, one drop of an ocular formulation is administered to an eye of the patient, wherein the ocular formulation comprises bethanechol chloride in an amount of about 0.001%, 0.01%, or 0.1% w/w.

In certain embodiments, the additional agent is aceclidine or a pharmaceutically acceptable salt thereof. In certain embodiments, the additional agent is aceclidine hydrochloride. In certain embodiments, the additional agent is administered to the eye of the patient in an amount ranging from about 0.01 mg to about 4 mg. In certain embodiments, the additional agent is administered to the eye of the patient in an amount ranging from about 0.01 mg to about 0.1 mg. In certain embodiments, the additional agent is administered to the eye of the patient in an amount of about 0.01 mg. In certain other embodiments, the additional agent is administered to the eye of the patient in an amount ranging from about 0.1 mg to about 1.5 mg.

In certain embodiments, one drop of an ocular formulation is administered to an eye of the patient, wherein the ocular formulation comprises aceclidine hydrochloride in an amount ranging from about 0.001% to about 0.1% w/w, about 0.001% to about 1.5% w/w, about 0.001% to about 3% w/w, about 1.35% to about 1.65% w/w, or about 0.01% to about 2% w/w. In certain embodiments, one drop of an ocular formulation is administered to an eye of the patient, wherein the ocular formulation comprises aceclidine hydrochloride in an amount of about 0.01%, 0.1%, 0.25%, 0.5%, 1%, 1.5%, 2%, 3%, or 4% w/w.

In certain embodiments, the additional agent is oxotremorine or a pharmaceutically acceptable salt thereof. In certain embodiments, the additional agent is oxotremorine. In certain embodiments, the additional agent is administered to the eye of the patient in an amount ranging from about 0.1 mg to about 1.0 mg. In certain embodiments, the additional agent is administered to the eye of the patient in an amount ranging from about 0.1 mg to about 0.3 mg. In certain embodiments, the additional agent is administered to the eye of the patient in an amount of about 0.2 mg. In certain other embodiments, the additional agent is administered to the eye of the patient in an amount ranging from about 0.3 mg to about 0.6 mg.

In certain embodiments, one drop of an ocular formulation is administered to an eye of the patient, wherein the ocular formulation comprises oxotremorine in an amount ranging from about 0.001% to about 0.1% w/w, about 0.001% to about 2% w/w, about 0.01% to about 2% w/w, or about 0.01% to about 4% w/w. In certain embodiments, one drop of an ocular formulation is administered to an eye of the patient, wherein the ocular formulation comprises oxotremorine in an amount of about 0.01%, 0.25%, 0.5%, 1%, 2%, or 4% w/w.

In certain embodiments, the additional agent is methacholine or a pharmaceutically acceptable salt thereof. In certain embodiments, the additional agent is methacholine. In certain embodiments, the additional agent is administered to the eye of the patient in an amount ranging from about 0.1 mg to about 1.0 mg. In certain embodiments, the additional agent is administered to the eye of the patient in an amount ranging from about 0.1 mg to about 0.3 mg. In certain embodiments, the additional agent is administered to the eye of the patient in an amount of about 0.2 mg. In certain other embodiments, the additional agent is administered to the eye of the patient in an amount ranging from about 0.3 mg to about 0.6 mg.

In certain embodiments, one drop of an ocular formulation is administered to an eye of the patient, wherein the ocular formulation comprises methacholine in an amount ranging from about 0.001% to about 0.1% w/w, about 0.001% to about 2% w/w, about 0.01% to about 2% w/w, or about 0.01% to about 4% w/w. In certain embodiments, one drop of an ocular formulation is administered to an eye of the patient, wherein the ocular formulation comprises methacholine in an amount of about 0.01%, 0.25%, 0.5%, 1%, 2%, or 4% w/w.

In certain embodiments, the additional agent is muscarine or a pharmaceutically acceptable salt thereof. In certain embodiments, the additional agent is muscarine. In certain embodiments, the additional agent is administered to the eye of the patient in an amount ranging from about 0.1 mg to about 1.0 mg. In certain embodiments, the additional agent is administered to the eye of the patient in an amount ranging from about 0.1 mg to about 0.3 mg. In certain embodiments, the additional agent is administered to the eye of the patient in an amount of about 0.2 mg. In certain other embodiments, the additional agent is administered to the eye of the patient in an amount ranging from about 0.3 mg to about 0.6 mg.

In certain embodiments, one drop of an ocular formulation is administered to an eye of the patient, wherein the ocular formulation comprises muscarine in an amount ranging from about 0.001% to about 0.1% w/w, about 0.001% to about 2% w/w, about 0.01% to about 2% w/w, or about 0.01% to about 4% w/w. In certain embodiments, one drop of an ocular formulation is administered to an eye of the patient, wherein the ocular formulation comprises muscarine in an amount of about 0.01%, 0.25%, 0.5%, 1%, 2%, or 4% w/w.

In certain embodiments, the additional agent is an alpha-2 adrenergic agonist. In certain embodiments, the additional agent is brimonidine or a pharmaceutically acceptable salt thereof. In certain embodiments, the additional agent is brimonidine tartrate. In certain embodiments, the additional agent is administered to the eye of the patient in an amount ranging from about 0.01 mg to about 4 mg. In certain embodiments, the additional agent is administered to the eye of the patient in an amount ranging from about 0.01 mg to about 0.1 mg. In certain embodiments, the additional agent is administered to the eye of the patient in an amount of about 0.1 mg. In certain other embodiments, the additional agent is administered to the eye of the patient in an amount ranging from about 0.1 mg to about 1 mg.

In certain embodiments, one drop of an ocular formulation is administered to an eye of the patient, wherein the ocular formulation comprises brimonidine tartrate in an amount ranging from about 0.01% to about 4% w/w, about 0.02% to about 4% w/w, about 0.02% to about 0.2% w/w, about 0.2% to about 3% w/w, or about 0.01% to about 2% w/w. In certain embodiments, one drop of an ocular formulation is administered to an eye of the patient, wherein the ocular formulation comprises brimonidine tartrate in an amount of about 0.01%, 0.02%, 0.1%, 0.2%, 0.5%, 1%, 1.5%, 2%, 3%, or 4% w/w.

In certain embodiments, the additional agent is carbamoylcholine or a pharmaceutically acceptable salt thereof. In certain embodiments, the additional agent is administered to the eye of the patient in an amount ranging from about 0.01 mg to about 4 mg. In certain embodiments, the additional agent is administered to the eye of the patient in an amount ranging from about 0.01 mg to about 0.1 mg. In certain embodiments, the additional agent is administered to the eye of the patient in an amount of about 0.1 mg. In certain other embodiments, the additional agent is administered to the eye of the patient in an amount ranging from about 0.1 mg to about 1 mg.

In certain embodiments, one drop of an ocular formulation is administered to an eye of the patient, wherein the ocular formulation comprises carbamoylcholine or a pharmaceutically acceptable salt thereof in an amount ranging from about 0.01% to about 4% w/w, about 0.02% to about 4% w/w, about 0.02% to about 0.2% w/w, about 0.2% to about 3% w/w, or about 0.01% to about 2% w/w. In certain embodiments, one drop of an ocular formulation is administered to an eye of the patient, wherein the ocular formulation comprises carbamoylcholine or a pharmaceutically acceptable salt thereof in an amount of about 0.01%, 0.02%, 0.1%, 0.2%, 0.5%, 1%, 1.5%, 2%, 3%, or 4% w/w.

In certain embodiments, the additional agent is physostigmine or a pharmaceutically acceptable salt thereof. In certain embodiments, the additional agent is administered to the eye of the patient in an amount ranging from about 0.01 mg to about 4 mg. In certain embodiments, the additional agent is administered to the eye of the patient in an amount ranging from about 0.01 mg to about 0.1 mg. In certain embodiments, the additional agent is administered to the eye of the patient in an amount of about 0.1 mg. In certain other embodiments, the additional agent is administered to the eye of the patient in an amount ranging from about 0.1 mg to about 1 mg.

In certain embodiments, one drop of an ocular formulation is administered to an eye of the patient, wherein the ocular formulation comprises physostigmine or a pharmaceutically acceptable salt thereof in an amount ranging from about 0.01% to about 4% w/w, about 0.02% to about 4% w/w, about 0.02% to about 0.2% w/w, about 0.2% to about 3% w/w, or about 0.01% to about 2% w/w. In certain embodiments, one drop of an ocular formulation is administered to an eye of the patient, wherein the ocular formulation comprises physostigmine or a pharmaceutically acceptable salt thereof in an amount of about 0.01%, 0.02%, 0.1%, 0.2%, 0.5%, 1%, 1.5%, 2%, 3%, or 4% w/w.

In certain embodiments, the additional agent is echothiophate or a pharmaceutically acceptable salt thereof. In certain embodiments, the additional agent is administered to the eye of the patient in an amount ranging from about 0.01 mg to about 4 mg. In certain embodiments, the additional agent is administered to the eye of the patient in an amount ranging from about 0.01 mg to about 0.1 mg. In certain embodiments, the additional agent is administered to the eye of the patient in an amount of about 0.1 mg. In certain other embodiments, the additional agent is administered to the eye of the patient in an amount ranging from about 0.1 mg to about 1 mg.

In certain embodiments, one drop of an ocular formulation is administered to an eye of the patient, wherein the ocular formulation comprises echothiophate or a pharmaceutically acceptable salt thereof in an amount ranging from about 0.01% to about 4% w/w, about 0.02% to about 4% w/w, about 0.02% to about 0.2% w/w, about 0.2% to about 3% w/w, or about 0.01% to about 2% w/w. In certain embodiments, one drop of an ocular formulation is administered to an eye of the patient, wherein the ocular formulation comprises echothiophate or a pharmaceutically acceptable salt thereof in an amount of about 0.01%, 0.02%, 0.1%, 0.2%, 0.5%, 1%, 1.5%, 2%, 3%, or 4% w/w.

In certain embodiments, the additional agent is acetylcholine or a pharmaceutically acceptable salt thereof. In certain embodiments, the additional agent is administered to the eye of the patient in an amount ranging from about 0.01 mg to about 4 mg. In certain embodiments, the additional agent is administered to the eye of the patient in an amount ranging from about 0.01 mg to about 0.1 mg. In certain embodiments, the additional agent is administered to the eye of the patient in an amount of about 0.1 mg. In certain other embodiments, the additional agent is administered to the eye of the patient in an amount ranging from about 0.1 mg to about 1 mg.

In certain embodiments, one drop of an ocular formulation is administered to an eye of the patient, wherein the ocular formulation comprises acetylcholine or a pharmaceutically acceptable salt thereof in an amount ranging from about 0.01% to about 4% w/w, about 0.02% to about 4% w/w, about 0.02% to about 0.2% w/w, about 0.2% to about 3% w/w, or about 0.01% to about 2% w/w. In certain embodiments, one drop of an ocular formulation is administered to an eye of the patient, wherein the ocular formulation comprises acetylcholine or a pharmaceutically acceptable salt thereof in an amount of about 0.01%, 0.02%, 0.1%, 0.2%, 0.5%, 1%, 1.5%, 2%, 3%, or 4% w/w.

In certain embodiments, the additional agent is a prostaglandin. In certain embodiments, the additional agent is dinoprostone or a pharmaceutically acceptable salt thereof. In certain embodiments, the additional agent is dinoprostone. In certain embodiments, the additional agent is administered to the eye of the patient in an amount ranging from about 0.1 mg to about 4 mg. In certain embodiments, the additional agent is administered to the eye of the patient in an amount ranging from about 0.1 mg to about 1 mg. In certain other embodiments, the additional agent is administered to the eye of the patient in an amount ranging from about 1 mg to about 3 mg. In certain embodiments, the additional agent is administered to the eye of the patient in an amount ranging from about 0.001 mg to about 0.1 mg. In certain embodiments, the additional agent is administered to the eye of the patient in an amount ranging from about 0.0025 mg to about 0.01 mg. In certain embodiments, the additional agent is administered to the eye of the patient in an amount of about 0.0025 mg. In certain embodiments, one drop of an ocular formulation is administered to an eye of the patient, wherein the ocular formulation comprises dinoprostone in an amount of about 0.002%, 0.003%, 0.004%, 0.005%, 0.006%, 0.007%, or 0.01% w/w.

In certain embodiments, the additional agent is latanaprost or a pharmaceutically acceptable salt thereof. In certain embodiments, the additional agent is latanaprost. In certain embodiments, the additional agent is administered to the eye of the patient in an amount ranging from about 0.001 mg to about 0.1 mg. In certain embodiments, the additional agent is administered to the eye of the patient in an amount ranging from about 0.0025 mg to about 0.01 mg. In certain embodiments, the additional agent is administered to the eye of the patient in an amount of about 0.0025 mg. In certain embodiments, one drop of an ocular formulation is administered to an eye of the patient, wherein the ocular formulation comprises latanaprost in an amount of about 0.002%, 0.003%, 0.004%, 0.005%, 0.006%, 0.007%, or 0.01% w/w. In certain embodiments, the additional agent is latanaprost, which is administered to the eye of the patient in an amount ranging from about 0.5 to about 1.0 micrograms, about 1.0 to about 1.5 micrograms, about 1.5 to about 2.0 micrograms of latanaoprost, or about 2.0 to about 5.0 micrograms of latanaoprost.

In certain embodiments, the additional agent is bimatoprost or a pharmaceutically acceptable salt thereof. In certain embodiments, the additional agent is bimatoprost. In certain embodiments, the additional agent is administered to the eye of the patient in an amount ranging from about 0.001 mg to about 0.1 mg. In certain embodiments, the additional agent is administered to the eye of the patient in an amount ranging from about 0.001 mg to about 0.003 mg. In certain embodiments, the additional agent is administered to the eye of the patient in an amount of about 0.002 mg. In certain embodiments, one drop of an ocular formulation is administered to an eye of the patient, wherein the ocular formulation comprises bimatoprost in an amount of about 0.001%, 0.005%, 0.008%, 0.009, 0.01%, 0.02%, 0.03%, 0.04%, or 0.05% w/w.

In certain embodiments, the additional agent is travoprost or a pharmaceutically acceptable salt thereof. In certain embodiments, the additional agent is travoprost. In certain embodiments, the additional agent is administered to the eye of the patient in an amount ranging from about 0.001 mg to about 0.1 mg. In certain embodiments, the additional agent is administered to the eye of the patient in an amount ranging from about 0.001 mg to about 0.01 mg. In certain embodiments, the additional agent is administered to the eye of the patient in an amount of about 0.005 mg. In certain embodiments, one drop of an ocular formulation is administered to an eye of the patient, wherein the ocular formulation comprises travoprost in an amount of about 0.002%, 0.003%, 0.004%, 0.005%, 0.006%, 0.007%, or 0.01% w/w.

In certain embodiments, the additional agent is EV06 or a pharmaceutically acceptable salt thereof. In certain embodiments, the additional agent is EV06 chloride. In certain embodiments, the additional agent is EV06 tartrate. In certain embodiments, the additional agent is administered to the eye of the patient in an amount ranging from about 0.25 mg to about 1.2 mg. In certain embodiments, the additional agent is administered to the eye of the patient in an amount ranging from about 0.25 mg to about 0.5 mg. In certain other embodiments, the additional agent is administered to the eye of the patient in an amount ranging from about 0.5 mg to about 0.75 mg. In certain embodiments, the additional agent is administered to the eye of the patient in an amount of about 0.6 mg.

In certain embodiments, the additional agent is a cholinesterase inhibitor.

In certain embodiments, yet another therapeutic agent is administered to the eye of the patient. In such embodiments, the method further comprises administering to the eye of the patient an alpha adrenergic agonist, such as brimonidine or a pharmaceutically acceptable salt thereof.

E. Fourth Method

Another aspect of the invention provides a method of treating presbyopia in a patient according to a monotherapy treatment regimen, comprising administering to an eye of a patient in need thereof a dosage of a single therapeutic agent in an amount effective for treatment of presbyopia, wherein the single therapeutic agent is an alpha-adrenergic antagonist.

The method may be further characterized by additional features, such as the dosing regimen and the identity of the dosage, as described in more detail below. The invention embraces all permutations and combinations of these features.

Accordingly, in certain embodiments, the dosage is administered at or near the bedtime of the patient. In certain embodiments, the dosage is administered within 1 hour of the patient's bedtime. In certain embodiments, the dosage comprises a pharmaceutically acceptable salt of phentolamine. In certain embodiments, the dosage comprises phentolamine mesylate.

In certain embodiments, the dosage of a single therapeutic agent is 1% w/w phentolamine mesylate solution. In certain embodiments, the dosage of a single therapeutic agent is 1.5% w/w phentolamine mesylate solution. In certain embodiments, the dosage of a single therapeutic agent is 2% w/w phentolamine mesylate solution.

In certain embodiments, the dosage is administered as a single eye drop. In certain embodiments, the dosage is administered as two eye drops.

F. Fifth Method

Another aspect of the invention provides a method of treating mydriasis in a patient, comprising administering to an eye of a patient in need thereof a dosage of an alpha-adrenergic antagonist in an amount effective to thereby treat the mydriasis.

The method may be further characterized by additional features, such as the cause of the mydriasis and the amount of reduction in pupil diameter the patient experiences. The invention embraces all permutations and combinations of these features.

Accordingly, in certain embodiments, the mydriasis is due to the patient having received an agent that causes pupil dilation. In certain embodiments, the mydriasis is due to the patient having received one or more of an adrenergic or parasympatholyic agent. In certain embodiments, the mydriasis is due to the patient having received one or more of an alpha agonist, a TAAR1 agonist, or NSAID. In certain embodiments, the mydriasis is due to the patient having received one or more of atropine, cyclopentolate, homatropine, scopolamine, tropicamide, flubiprofen, suprofen, hydroxyamphetamine, phenylephrine, cyclopentolate, ketorolac, or a pharmaceutically acceptable salt thereof. In certain embodiments, the mydriasis is due to the patient having received one or more of atropine, cyclopentolate, homatropine, scopolamine, tropicamide, phenylephrine, or a pharmaceutically acceptable salt thereof. In certain embodiments, the mydriasis is due to the patient having received one or more of atropine, cyclopentolate, homatropine, scopolamine, tropicamide, or a pharmaceutically acceptable salt thereof. In certain embodiments, the mydriasis is due to the patient having received atropine, homatropine, scopolamine, or a pharmaceutically acceptable salt thereof. In certain embodiments, the mydriasis is due to the patient having received cyclopentolate or a pharmaceutically acceptable salt thereof. In certain embodiments, the mydriasis is due to the patient having received tropicamide or a pharmaceutically acceptable salt thereof. In certain embodiments, the mydriasis is due to the patient having received phenylephrine or a pharmaceutically acceptable salt thereof.

In certain embodiments, the mydriasis is due to the patient having received flubiprofen or a pharmaceutically acceptable salt thereof. In certain embodiments, the mydriasis is due to the patient having received flubiprofen sodium. In certain embodiments, the mydriasis is due to the patient having received suprofen or a pharmaceutically acceptable salt thereof. In certain embodiments, the mydriasis is due to the patient having received hydroxyamphetamine or a pharmaceutically acceptable salt thereof. In certain embodiments, the mydriasis is due to the patient having received tropicamide or a pharmaceutically acceptable salt thereof. In certain embodiments, the mydriasis is due to the patient having received cyclopentolate or a pharmaceutically acceptable salt thereof. In certain embodiments, the mydriasis is due to the patient having received ketorolac or a pharmaceutically acceptable salt thereof. In certain embodiments, the mydriasis is due to the patient having received hydroxyamphetamine hydrobromide and tropicamide, which is marketed as PAREMYD®. In certain embodiments, the mydriasis is due to the patient having received cyclopentolate hydrochloride and phenylephrine hydrochloride, which is marketed as CYCLOMYDRIL®. In certain embodiments, the mydriasis is due to the patient having received scopolamine and phenylephrine. In certain embodiments, the mydriasis is due to the patient having received ketorolac and phenylephrine, which is marketed as OMIDRIA®.

The method may be further characterized according to the dosing regimen. For example, in certain embodiments, the dosage is administered to the eye no more than once per day. In certain embodiments, the dosage is administered to the eye no more than once every two days. In certain embodiments, the dosage is administered to the eye of the patient after the patient has completed an eye examination in which a pupil dilating agent was administered to the patient's eye.

The method may be further characterized according to the amount of reduction in pupil diameter. For example, in certain embodiments, the patient experiences at least a 1 mm reduction in pupil diameter when measured under mesopic conditions relative to the diameter of the patient's pupil under the same mesopic conditions but not having received said dosage. In certain embodiments, the patient experiences at least a 2 mm reduction in pupil diameter when measured under mesopic conditions relative to the diameter of the patient's pupil under the same mesopic conditions but not having received said dosage. In certain embodiments, the patient experiences at least a 3 mm reduction in pupil diameter when measured under mesopic conditions relative to the diameter of the patient's pupil under the same mesopic conditions but not having received said dosage. In certain embodiments, the patient experiences at least a 4 mm, 5 mm, or greater reduction in pupil diameter when measured under mesopic conditions relative to the diameter of the patient's pupil under the same mesopic conditions but not having received said dosage. In certain other embodiments, the patient experiences a reduction in pupil diameter ranging from about 0.5 mm to about 5 mm when measured under mesopic conditions relative to the diameter of the patient's pupil under the same mesopic conditions but not having received said dosage.

In certain embodiments, the patient experiences at least a 1 mm reduction in pupil diameter when measured under photopic conditions relative to the diameter of the patient's pupil under the same photopic conditions but not having received said dosage. In certain embodiments, the patient experiences at least a 2 mm reduction in pupil diameter when measured under photopic conditions relative to the diameter of the patient's pupil under the same photopic conditions but not having received said dosage. In certain embodiments, the patient experiences at least a 3 mm reduction in pupil diameter when measured under photopic conditions relative to the diameter of the patient's pupil under the same photopic conditions but not having received said dosage. In certain embodiments, the patient experiences at least a 4 mm, 5 mm, or greater reduction in pupil diameter when measured under photopic conditions relative to the diameter of the patient's pupil under the same photopic conditions but not having received said dosage. In certain other embodiments, the patient experiences a reduction in pupil diameter ranging from about 0.5 mm to about 5 mm when measured under photopic conditions relative to the diameter of the patient's pupil under the same photopic conditions but not having received said dosage.

In certain embodiments, the patient experiences at least a 1 mm reduction in pupil diameter relative to the diameter of the patient's pupil measured under the same conditions (e.g., mesopic or photopic) but not having received said dosage. In certain embodiments, the patient experiences at least a 2 mm reduction in pupil diameter relative to the diameter of the patient's pupil measured under the same conditions (e.g., mesopic or photopic) but not having received said dosage. In certain embodiments, the patient experiences at least a 3 mm reduction in pupil diameter relative to the diameter of the patient's pupil measured under the same conditions (e.g., mesopic or photopic) but not having received said dosage. In certain embodiments, the patient experiences at least a 4 mm, 5 mm, or greater reduction in pupil diameter relative to the diameter of the patient's pupil measured under the same conditions (e.g., mesopic or photopic) but not having received said dosage. In certain embodiments, the patient experiences at least a 4 mm, 5 mm, or greater reduction in pupil diameter relative to the diameter of the patient's pupil measured under the same conditions (e.g., mesopic or photopic) but not having received said dosage. In certain other embodiments, the patient experiences a reduction in pupil diameter ranging from about 0.5 mm to about 5 mm relative to the diameter of the patient's pupil under the same conditions (e.g., mesopic or photopic) but not having received said dosage.

G. Sixth Method

Another aspect of the invention provides a method of preventing progressive myopia in a patient, comprising administering to an eye of a patient in need thereof a dosage of an alpha-adrenergic antagonist in an amount effective to thereby prevent progressive myopia.

The method may be further characterized by additional features. For example, in certain embodiments, the patient is an adult human. In certain other embodiments, the patient is a pediatric human. In certain embodiments, the method further comprises administering to the eye of the patient one or more additional agents described herein. The invention embraces all permutations and combinations of these features.

H. Additional Features of the First, Second, Third and Fourth Therapeutic Methods Additional features that may characterize the First, Second, Third, and Fourth therapeutic methods described herein (e.g., the methods described in Parts A-D above) are provided below and include, for example, the degree of eye redness, the dosing regimen of the alpha-adrenergic antagonist, the duration of the therapeutic effect against presbyopia, and the pupil diameter in the eye that received the dosage. A more thorough description of such features is provided below. The invention embraces all permutations and combinations of these features.

Degree of Eye Redness

The methods may be further characterized according to the degree of eye redness the patient experiences. The degree of eye redness can be evaluated and characterized using procedures described in the literature, such as the Cornea and Contact Lens Research Unit (CCLRU) Redness Grading Scale developed by the School of Optometry, University of New South Wales. See, for example, Terry et al. in *Optom. Vis. Sci.* (1993) vol. 70, pages 234-243; and Pult et al. in *Ophthal. Physiol. Opt.* (2008) vol. 28, pages 13-20. The CCLRU Redness Grading Scale evaluates eye redness on a four-point scale: (0) no eye redness, (1) very slight eye redness, (2) slight eye redness, (3) moderate eye redness, and (4) severe eye redness. See FIG. 1 for an illustration of the eye redness scale.

In certain embodiments, the patient experiences an increase in eye redness of no more than two grades measured using the CCLRU Redness Grading Scale during the patient's waking hours compared to the patient's level of eye redness without receiving said dosage of alpha-adrenergic antagonist. In certain embodiments, the patient experiences an increase in eye redness of no more than one grade measured using the CCLRU Redness Grading Scale during the patient's waking hours compared to the patient's level of eye redness without receiving said dosage of alpha-adrenergic antagonist. In certain embodiments, any increase in eye redness experienced by the patient is less than one grade measured using the CCLRU Redness Grading Scale during the patient's waking hours compared to the patient's level of eye redness without receiving said dosage of alpha-adrenergic antagonist.

Dosing Regimen of the Alpha-Adrenergic Antagonist

The methods may be further characterized according to the dosing regimen of the alpha-adrenergic antagonist. For example, in certain embodiments, the dosage of alpha-adrenergic antagonist is administered on a daily basis.

In certain embodiments, the dosage of alpha-adrenergic antagonist is administered for at least three consecutive days. In certain embodiments, the dosage of alpha-adrenergic antagonist is administered for at least seven consecutive days. In certain embodiments, the dosage of alpha-adrenergic antagonist is administered for at least fourteen consecutive days.

In certain embodiments, the dosage is administered one per day. In certain embodiments, the dosage is administered multiple times per day, such as two or three times per day.

In certain embodiments, the dosage is administered as a single eye drop. In certain embodiments, the dosage is administered as two eye drops.

Duration of Therapeutic Effect Against Presbyopia

The methods may be further characterized according to the duration of the therapeutic effect against presbyopia. For example, in certain embodiments, the method provides a therapeutic effect against presbyopia for a duration of at least 6 hours. In certain embodiments, the method provides a therapeutic effect against presbyopia for a duration of at least 12 hours. In certain embodiments, the method provides a therapeutic effect against presbyopia for a duration of at least 16 hours. In certain embodiments, the method provides a therapeutic effect against presbyopia for a duration of at least 18 hours. In certain embodiments, the method provides a therapeutic effect against presbyopia for a duration of at least 20 hours. In certain embodiments, the method provides a therapeutic effect against presbyopia for a duration of at least 24 hours. In certain embodiments, the method provides a therapeutic effect against presbyopia for a duration of at least 36 hours. In certain embodiments, the method provides a therapeutic effect against presbyopia for a duration of at least 48 hours.

Improvement in Patient's Vision

The methods may be further characterized according to the improvement in the patient's vision. For example, in certain embodiments, the method provides an improvement in visual acuity characterized by at least a one-line improvement in the patient's vision measured using a vision chart. In certain embodiments, the method results in an improvement in visual acuity characterized by at least a two-line improvement in the patient's vision measured using a vision chart. In certain embodiments, the method results in an improvement in visual acuity characterized by at least a three-line improvement in the patient's vision measured using a vision chart. In certain embodiments, the method results in an improvement in visual acuity characterized by an improvement in the patient's vision of four or more lines measured using a vision chart. In certain embodiments, the vision chart is a Snellen chart. In certain other embodiments, the vision chart is a Jaeger chart. In certain other embodiments, the vision chart is a Rosenbaum chart or an ETDRS chart. In certain embodiments, the improvement in visual acuity is measured at a near distance (e.g., about 1, 2, or 3 feet). In certain embodiments, the improvement in visual acuity is measured at a far distance (e.g., about 20, 25, or 30 feet). In certain embodiments, the improvement in visual acuity is an improvement in near-vision visual acuity. In certain embodiments, the improvement in visual acuity is an improvement in distance visual acuity. In certain embodiments, the improvement in visual acuity is (i) an improvement in near-vision visual acuity and (ii) an improvement in distance visual acuity.

The method may be further characterized according to the duration of the improvement in the patient's vision. In certain embodiments, the patient experiences said improvement for a duration of at least 6 hours. In certain embodiments, the patient experiences said improvement for a duration of at least 12 hours. In certain embodiments, the patient experiences said improvement for a duration of at least 18 hours. In certain embodiments, the patient experiences said improvement for a duration of at least 20 hours. In certain embodiments, the patient experiences said improvement for a duration of at least 24 hours. In certain embodiments, the patient experiences said improvement for a duration of at least 30 hours. In certain embodiments, the patient experiences said improvement for a duration of at least 48 hours.

Pupil Diameter in the Eye that Received the Dosage

The methods may be further characterized according to the pupil diameter in the eye that received the dosage and the duration that said pupil diameter is maintained. For example, in certain embodiments, as a result of the administering, the patient experiences the effect of having a pupil diameter of less than 3.0 in the eye that received said dosage when measured under photopic conditions. In certain embodiments, as a result of the administering, the patient experiences the effect of having a pupil diameter of less than 2.8 in the eye that received said dosage when measured under photopic conditions. In certain embodiments, as a result of the administering, the patient experiences the effect of having a pupil diameter of less than 2.6 mm in the eye that received said dosage when measured under photopic conditions. In certain embodiments, as a result of the administering, the patient experiences the effect of having a pupil diameter of less than 2.4 mm in the eye that received said dosage when measured under photopic conditions. In certain embodiments, as a result of the administering, the patient experiences the effect of having a pupil diameter of less than 2.2 mm in the eye that received said dosage when measured under photopic conditions. In certain embodiments, the patient experiences the effect of having a pupil diameter of less than 2 mm in the eye that received said dosage when measured under photopic conditions. In certain embodiments, as a result of the administering, the patient experiences the effect of having a pupil diameter of less than 1.9 mm in the eye that received said dosage when measured under photopic conditions. In certain embodiments, as a result of the administering, the patient experiences the effect of having a pupil diameter of less than 1.8 mm in the eye that received said dosage when measured under photopic conditions. In certain embodiments, as a result of the administering, the patient experiences the effect of having a pupil diameter of less than 1.7 mm in the eye that received said dosage when measured under photopic conditions. In certain embodiments, as a result of the administering, the patient experiences the effect of having a pupil diameter of less than 1.6 mm in the eye that received said dosage when measured under photopic conditions.

In certain embodiments, the patient experiences said effect for a duration of at least 6 hours. In certain embodiments, the patient experiences said effect for a duration of at least 12 hours. In certain embodiments, the patient experiences said effect for a duration of at least 18 hours. In certain embodiments, the patient experiences said effect for a duration of at least 20 hours. In certain embodiments, the patient experiences said effect for a duration of at least 24 hours. In certain embodiments, the patient experiences said effect for a duration of at least 30 hours. In certain embodiments, the patient experiences said effect for a duration of at least 48 hours.

Reduction in Intraocular Pressure

Another benefit that may be experienced by patients is a reduction in intraocular pressure in an eye that receives an alpha-adrenergic antagonist.

I. General Considerations for Therapeutic Methods

General considerations that may be applied to therapeutic methods described herein (e.g., the methods described in Parts A-H above) are provided below and include, for example, the identity of the alpha-adrenergic antagonist, the dosage of alpha-adrenergic antagonist, the formulation of the dosage, and patient populations that may derive particular benefits from the therapeutic methods. A more thorough description of such features is provided below. The invention embraces all permutations and combinations of these features.

Identity of the Alpha-Adrenergic Antagonist

The methods may be further characterized according to the identity of the alpha-adrenergic antagonist. For example, in certain embodiments, the alpha-adrenergic antagonist is phentolamine, phenoxybenzamine, tolazoline, trazodone, alfuzosin, doxazosin, prazosin, tamsulosin, terazosin, silodosin, atipamezole, idazoxan, mirtazapine, yohimbine, fenoldopam, thymoxamine, or a pharmaceutically acceptable salt of any of the foregoing. In certain embodiments, the alpha-adrenergic antagonist is phentolamine or a pharmaceutically acceptable salt thereof. In certain embodiments, the alpha-adrenergic antagonist is a pharmaceutically acceptable salt of phentolamine. In certain embodiments, the alpha-adrenergic antagonist is phentolamine mesylate. In certain other embodiments, the alpha-adrenergic antagonist is fenoldopam or a pharmaceutically acceptable salt thereof. In certain embodiments, the alpha-adrenergic antagonist is fenoldopam mesylate.

In certain embodiments, the alpha-adrenergic antagonist is a non-selective alpha-adrenergic antagonist. In certain embodiments, the alpha-adrenergic antagonist is a reversible, non-selective alpha-adrenergic antagonist.

In certain embodiments, the alpha-adrenergic antagonist is characterized according to its activity towards certain alpha-adrenergic receptors. Accordingly, in certain embodiments, the alpha-adrenergic antagonist has antagonist activity towards an alpha-1 adrenergic receptor. Activity toward the alpha-1 adrenergic receptor may be further characterized according to whether there is activity toward one or more of the alpha-1 adrenergic receptor subtypes (e.g., alpha-1A, alpha-1B, and alpha-1D). Accordingly, in certain embodiments, the alpha-adrenergic antagonist has antagonist activity towards the alpha-1A adrenergic receptor. In certain embodiments, the alpha-adrenergic antagonist has antagonist activity towards the alpha-1B adrenergic receptor. In certain embodiments, the alpha-adrenergic antagonist has antagonist activity towards the alpha-1D adrenergic receptor. In certain embodiments, the alpha-adrenergic antagonist has antagonist activity towards each of the alpha-1 adrenergic receptor subtypes.

In certain embodiments, the alpha-adrenergic antagonist has antagonist activity towards an alpha-2 adrenergic receptor. Activity toward the alpha-2 adrenergic receptor may be further characterized according to whether there is activity toward one or more of the alpha-2 adrenergic receptor subtypes (e.g., alpha-2A, alpha-2B, and alpha-2C). Accordingly, in certain embodiments, the alpha-adrenergic antagonist has antagonist activity towards the alpha-2A adrenergic receptor. In certain embodiments, the alpha-adrenergic antagonist has antagonist activity towards the alpha-2B adrenergic receptor. In certain embodiments, the alpha-adrenergic antagonist has antagonist activity towards the alpha-2C adrenergic receptor. In certain embodiments, the alpha-adrenergic antagonist has antagonist activity towards each of the alpha-2 adrenergic receptor subtypes.

The alpha-adrenergic antagonist may be characterized according to its activity towards (i) an alpha-1 adrenergic receptor versus (ii) an alpha-2 adrenergic receptor. In certain embodiments, the alpha-adrenergic antagonist has antagonist activity at both (i) an alpha-1 adrenergic receptor and (ii) an alpha-2 adrenergic receptor. In certain embodiments, the alpha-adrenergic antagonist has antagonist activity at (i) an alpha-1 adrenergic receptor but not (ii) an alpha-2 adrenergic receptor. In certain embodiments, the alpha-adrenergic antagonist has antagonist activity at (i) an alpha-2 adrenergic receptor but not (ii) an alpha-1 adrenergic receptor. In certain embodiments, the inhibitory activity (as, for example, measured by an $IC_{50}$ value) of the alpha-adrenergic antagonist is at least 10-fold greater towards (i) the alpha-1 adrenergic receptor compared to the (ii) alpha-2 adrenergic receptor. In certain embodiments, the inhibitory activity (as, for example, measured by an $IC_{50}$ value) of the alpha-adrenergic antagonist is at least 10-fold greater towards (i) the alpha-2 adrenergic receptor compared to (ii) the alpha-1 adrenergic receptor.

Dosage of Alpha-Adrenergic Antagonist

The methods may be further characterized according to the dosage of the alpha-adrenergic antagonist. For example, in certain embodiments, the dosage of alpha-adrenergic antagonist is less than about 2 mg. In certain embodiments, the dosage of alpha-adrenergic antagonist is less than about 1.5 mg. In certain embodiments, the dosage of alpha-adrenergic antagonist is less than about 1 mg. In certain embodiments, the dosage of alpha-adrenergic antagonist is less than about 0.5 mg.

Dosage of Phentolamine or Pharmaceutically Acceptable Salt Thereof

When the alpha-adrenergic antagonist is phentolamine or a pharmaceutically acceptable salt thereof, the methods may be further characterized according to the amount of phentolamine or pharmaceutically acceptable salt thereof in the dosage. For example, in certain embodiments, the dosage contains from about 0.1 mg to about 2.0 mg of phentolamine or a pharmaceutically acceptable salt thereof. In certain embodiments, the dosage contains from about 0.5 mg to about 1.0 mg of phentolamine or a pharmaceutically acceptable salt thereof.

In certain other embodiments, the dosage contains from about 0.1 mg to about 2.0 mg of phentolamine mesylate. In certain embodiments, the dosage contains from about 0.2 mg to about 0.7 mg of phentolamine mesylate. In certain embodiments, the dosage contains about 0.25 mg of phentolamine mesylate. In certain other embodiments, the dosage contains from about 0.4 mg to about 0.6 mg of phentolamine mesylate. In certain embodiments, the dosage contains about 0.5 mg of phentolamine mesylate. In certain other embodiments, the dosage contains from about 0.8 mg to about 1.2 mg of phentolamine mesylate. In certain embodiments, the dosage contains about 1 mg of phentolamine mesylate.

The dosage of phentolamine or a pharmaceutically acceptable salt thereof is desirably administered to the eye of the patient in the form of an ophthalmic solution, which is delivered to the eye in the form of an eye drop. In certain embodiments, the dosage is administered as one eye drop. A standard eye drop typically contains from about 0.03 mL to about 0.05 mL of solution. Preferably, an eye drop contains about 0.05 mL of solution.

In certain embodiments, the dosage may be in the form of an ophthalmic solution. For example, in certain embodiments, the dosage is an ophthalmic solution containing an aqueous pharmaceutically acceptable carrier and phentolamine or a pharmaceutically acceptable salt thereof. In certain embodiments, the dosage is an ophthalmic solution containing water, a polyol, and phentolamine or a pharmaceutically acceptable salt thereof. In certain embodiments, the dosage is an ophthalmic solution containing water, a polyol, an alkali metal carboxylate, and phentolamine or a pharmaceutically acceptable salt thereof.

In certain other embodiments, the dosage is an ophthalmic solution containing an aqueous pharmaceutically acceptable carrier and phentolamine mesylate. In certain embodiments, the dosage is an ophthalmic solution containing water, mannitol, and phentolamine mesylate. In certain embodiments, the dosage is an ophthalmic solution containing water, mannitol, sodium acetate, and phentolamine mesylate.

In certain other embodiments, the dosage is an aqueous ophthalmic solution free of a chelating agent containing:
(a) about 0.1% (w/v) to about 2% (w/v) of phentolamine mesylate;
(b) about 1% (w/v) to about 6% (w/v) of at least one polyol compound selected from the group consisting of mannitol, glycerol, and propylene glycol;
(c) about 1 mM to about 6 mM of an alkali metal acetate; and
(d) water;
wherein the solution has a pH in the range of 4 to 6 and does not contain a chelating agent.

In certain embodiments, the dosage is an aqueous ophthalmic solution free of a chelating agent containing:
(a) about 0.5% (w/v) to about 2% (w/v) of phentolamine mesylate;
(b) about 1% (w/v) to about 6% (w/v) of at least one polyol compound selected from the group consisting of mannitol, glycerol, and propylene glycol;
(c) about 1 mM to about 6 mM of an alkali metal acetate; and
(d) water;
wherein the solution has a pH in the range of 4.5 to 5.5 and does not contain a chelating agent.

In certain embodiments, the at least one polyol is mannitol. In certain embodiments, the solution contains 4% (w/v) mannitol. In certain embodiments, the alkali metal acetate is sodium acetate. In certain embodiments, the solution comprises 3 mM sodium acetate.

In certain embodiments, the dosage is an aqueous ophthalmic solution free of a chelating agent containing:
(a) about 0.25% (w/v) to about 2% (w/v) of phentolamine mesylate;
(b) about 3% (w/v) to about 5% (w/v) of mannitol;
(c) about 2 mM to about 4 mM of sodium acetate; and
(d) water;
wherein the solution has a pH in the range of 4.5 to 5.2 and does not contain a chelating agent.

In certain embodiments, the dosage is an aqueous ophthalmic solution free of a chelating agent containing:
(a) about 0.5% (w/v) to about 2% (w/v) of phentolamine mesylate;
(b) about 3% (w/v) to about 5% (w/v) of mannitol;
(c) about 2 mM to about 4 mM of sodium acetate; and
(d) water;
wherein the solution has a pH in the range of 4.6 to 5.2 and does not contain a chelating agent.

In certain embodiments, the dosage is an aqueous ophthalmic solution free of a chelating agent containing:
(a) about 0.5% (w/v) to about 1% (w/v) of phentolamine mesylate;
(b) about 4% mannitol;
(c) about 3 mM sodium acetate; and
(d) water;
wherein the solution has a pH in the range of 4.6 to 5.2 and does not contain a chelating agent.

In certain embodiments, the dosage is an aqueous ophthalmic solution containing:
(a) about 0.25% (w/v) to about 2% (w/v) of phentolamine mesylate;
(b) about 3% (w/v) to about 5% (w/v) of mannitol;
(c) about 1 mM to about 6 mM of sodium acetate; and
(d) water;
wherein the solution has a pH in the range of 4.5 to 5.2 and does not contain any additional component that is a chelating agent.

In certain embodiments, the dosage is an aqueous ophthalmic solution containing:
(a) about 1% (w/v) of phentolamine mesylate;
(b) about 3% (w/v) to about 5% (w/v) of mannitol;
(c) about 2 mM to about 4 mM of a buffer comprising sodium acetate; and
(d) water;
wherein the solution has a pH in the range of 4.5 to 5.2 and does not contain any additional component that is a chelating agent.

In certain embodiments, the dosage is an aqueous ophthalmic solution containing:
(a) about 0.25% (w/v) to about 2% (w/v) of phentolamine mesylate;
(b) about 3% (w/v) to about 5% (w/v) of mannitol;
(c) about 2 mM to about 4 mM of sodium acetate; and
(d) water;
wherein the solution has a pH in the range of 4.5 to 5.2 and does not contain any additional component that is a chelating agent.

In certain embodiments, the dosage is an aqueous ophthalmic solution containing:
(a) about 0.5% (w/v) to about 2% (w/v) of phentolamine mesylate;
(b) about 3% (w/v) to about 5% (w/v) of mannitol;
(c) about 2 mM to about 4 mM of a buffer comprising sodium acetate; and
(d) water;
wherein the solution has a pH in the range of 4.6 to 5.2 and does not contain any additional component that is a chelating agent.

In certain embodiments, the dosage is an aqueous ophthalmic solution containing:
(a) about 0.5% (w/v) to about 1% (w/v) of phentolamine mesylate;
(b) about 4% mannitol;
(c) about 3 mM of a buffer comprising sodium acetate; and
(d) water;
wherein the solution has a pH in the range of 4.6 to 5.2 and does not contain any additional component that is a chelating agent.

In certain embodiments, the dosage is an aqueous ophthalmic solution comprising: (a) about 1% (w/v) of phentolamine mesylate; (b) about 4% (w/v) mannitol; (c) about 3 mM of a buffer comprising sodium acetate; and (d) water; wherein the solution has a pH in the range of 4.5 to 5.5 and does not contain any additional component that is a chelating agent.

In certain embodiments, the dosage is an aqueous ophthalmic solution free of a chelating agent comprising: (a) about 1% (w/v) of phentolamine mesylate; (b) about 4% (w/v) mannitol; (c) about 3 mM of a buffer comprising sodium acetate; and (d) water; wherein the solution has a pH in the range of 4.0 to 7.5 and does not contain a chelating agent.

Combination Therapy Dosing Considerations

In embodiments where more than one therapeutic agent is administered, the amount of each therapeutic agent and the relative timing of administration of each therapeutic agent may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously, and the like.

In certain embodiments, the therapeutic agents may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Patient Populations that May Derive Particular Benefits from the Therapeutic Methods The methods may be further characterized according to patient populations that may derive particular benefits from the therapeutic methods. For example, in certain embodiments, the patient is a human. In certain embodiments, the patient is an adult human. In certain embodiments, the patient is a geriatric human. In certain embodiments, the patient is a pediatric human.

Time of Administration

Various methods described above require administration of the dosage at or near the bedtime of the patient. Accordingly, in certain embodiments, the dosage is administered within 2 hours, 1.5 hours, 1 hour, 45 minutes, 30 minutes, or 15 minutes of the patient's bedtime. In certain embodiments, the dosage is administered within 1 hour of the patient's bedtime.

Administering an Agent that Reduces Eye Redness

The methods may be further characterized according to whether or not an agent that reduces eye redness is administered to the eye of the patient. In certain embodiments, the method further comprises administering to the eye of the patient an effective amount of an agent reduces eye redness. Exemplary agents that reduce eye redness are brimonidine, tetrahydrozoline, oxymetazoline, naphthazoline, or a pharmaceutically acceptable salt thereof. These agents are not expected to alter pupil diameter. In certain embodiments, the agent that reduces eye redness is brimonidine or a pharmaceutically acceptable salt thereof (e.g., brimonidine tartrate). Brimonidine tartrate is marketed as LUMIFY® (which is an ophthalmic solution containing brimonidine tartrate (0.025% w/w)). In certain embodiments, the agent that reduces eye redness is oxymetazoline or a pharmaceutically acceptable salt thereof. An ophthalmic solution containing oxymetazoline is commercially available as VISINE L.R.®. In certain embodiments, the agent that reduces eye redness is naphthazoline or a pharmaceutically acceptable salt thereof, such as naphthazoline hydrochloride, which is marketed commercially as CLEAR EYES®.

Improvement in Visual Performance

One benefit of the therapeutic methods is that the patient may experience an improvement in visual performance. Visual performance pertains to the patient's overall vision quality and includes a patient's ability to see clearly, as well as ability to distinguish between an object and its background.

One aspect of visual performance is visual acuity. Visual acuity is a measure of a patient's ability to see clearly. Visual acuity can be measured using, for example, a Snellen chart. Further, the visual acuity measurement can be taken under scotopic conditions, mesopic conditions, and/or photopic conditions.

Another aspect of visual performance is contrast sensitivity. Contrast sensitivity is a measure of the patient's ability to distinguish between an object and its background. Contrast sensitivity can be measured using, for example, a Holladay Automated Contrast Sensitivity System. The contrast sensitivity can be measured under various light conditions, including, for example, photopic conditions, mesopic conditions, and scotopic conditions, each either with or without glare. In certain embodiments, the contrast sensitivity is measured under mesopic conditions either with or without glare.

In certain embodiments, the improvement in visual performance provided by the method is improved visual acuity. In certain embodiments, the improvement in visual performance provided by the method is improved visual acuity under scotopic conditions. In certain embodiments, the improvement in visual performance provided by the method is improved visual acuity under mesopic conditions. In certain embodiments, the improvement in visual performance provided by the method is improved visual acuity under photopic conditions. In certain embodiments, the improvement in visual acuity is a three-line improvement in the patient's vision as measured using a vision chart. In certain embodiments, the improvement in visual acuity is a two-line improvement in the patient's vision as measured using a vision chart. In certain other embodiments, the improvement in visual acuity is a one-line improvement in the patient's vision as measured using a vision chart. In certain embodiments, the vision chart is a Snellen chart. In certain other embodiments, the vision chart is a Jaeger chart. In certain other embodiments, the vision chart is a Rosenbaum chart or a ETDRS chart. In certain embodiments, the improvement in visual acuity is measured at a near distance (e.g., about 1, 2, or 3 feet). In certain embodiments, the improvement in visual acuity is measured at a far distance (e.g., about 20, 25, or 30 feet). In certain embodiments, the improvement in visual acuity is an improvement in near-vision visual acuity. In certain embodiments, the improvement in visual acuity is an improvement in distance visual acuity. In certain embodiments, the improvement in visual acuity is (i) an improvement in near-vision visual acuity and (ii) an improvement in distance visual acuity.

In certain embodiments, the improvement in visual performance provided by the method is improved contrast sensitivity. The improvement in contrast sensitivity can be measured under various light conditions, such as photopic conditions, mesopic conditions, and scotopic conditions. In certain embodiments, the improvement in visual performance provided by the method is improved contrast sensitivity under photopic conditions. In certain embodiments, the improvement in visual performance provided by the method is improved contrast sensitivity under mesopic conditions. In certain embodiments, the improvement in visual performance provided by the method is improved contrast sensitivity under scotopic conditions. Further, contrast sensitivity can be measured in the presence of glare or the absence of glare. All combinations of light conditions and glare are contemplated.

Benefits provided by the therapeutic methods can be characterized according to the patient's improvement in contrast sensitivity. For example, in certain embodiments, the improvement in contrast sensitivity is at least a 10% (or 20%, 30%, 50%, 60%, or 70%) improvement measured under mesopic conditions using the Holladay Automated Contrast Sensitivity System. In certain embodiments, the improvement in contrast sensitivity is at least a 10% (or 20%, 30%, 50%, 60%, or 70%) improvement measured under photopic conditions using the Holladay Automated Contrast Sensitivity System. In certain other embodiments, the improvement in contrast sensitivity is at least a 10% (or 20%, 30%, 50%, 60%, or 70%) improvement measured under mesopic conditions or scotopic conditions using the Holladay Automated Contrast Sensitivity System. In certain other embodiments, the improvement in contrast sensitivity is measured using a Pelli-Robson Contrast Sensitivity Chart.

In certain other embodiments, the improvement in visual performance provided by the method is both (i) improved visual acuity (such as under scotopic conditions, mesopic conditions, and/or photopic conditions) and (ii) improved contrast sensitivity (such as under scotopic conditions, mesopic conditions, and/or photopic conditions).

In certain other embodiments, the improvement in visual performance is characterized according to one or more of the following:
  assessment of uncorrected near visual acuity (e.g., a binocular assessment of uncorrected near visual acuity);
  average change from Baseline in Uncorrected Near Visual Acuity (UNVA); or
  proportion of subjects with at least a 3 line (e.g., 15 letter) improvement in the study eye in the measurement of post-treatment monocular best-corrected distance visual acuity at 45 cm compared to baseline monocular best-corrected distance visual acuity at 45 cm post treatment.

In certain other embodiments, the improvement in visual performance is characterized according to one or more of the following:
  assessment of uncorrected near visual acuity (e.g., a binocular assessment of uncorrected near visual acuity);
  average change from Baseline in Uncorrected Near Visual Acuity (UNVA, binocular); or
  proportion of subjects with at least a 3 line (e.g., 15 letter) improvement in the study eye in the measurement of post-treatment monocular best-corrected distance visual acuity at 35 cm compared to baseline monocular best-corrected distance visual acuity at 35 cm post treatment.

Reduction in Pupil Diameter

One benefit of the therapeutic methods is that the patient may experience a reduction in pupil diameter. Reduction in pupil diameter can result in improvement in visual performance.

The reduction in pupil diameter may be characterized according to the percent reduction in pupil diameter due to administering the alpha-adrenergic antagonist, such as where the reduction in pupil diameter is at least 5%, 10%, 15%, 20%, 30%, or 40%. In certain embodiments, the reduction in pupil diameter is in the range of from about 10% to about 40% compared to the pupil diameter of the patient under the same conditions but not having received the therapy defined by the method. In certain embodiments, the reduction in pupil diameter is in the range of from about 20% to about 30% compared to the pupil diameter of the patient under the same conditions but not having received the therapy defined by the method. In certain embodiments, the reduction in pupil diameter is in the range of from about 20% to about 40% compared to the pupil diameter of the patient under the same conditions but not having received the therapy defined by the method. In certain embodiments, the reduction in pupil diameter is measured under photopic conditions.

In a more specific embodiment, the reduction in pupil diameter can be characterized according to, for example, the percent reduction in pupil diameter and size of the pupil measured under certain light conditions. Accordingly, in certain embodiments, the reduction in pupil diameter under mesopic conditions is at least 5% compared to the pupil diameter of the patient under the same mesopic conditions but not having received the therapy defined by the method. In certain other embodiments, the reduction in pupil diameter under mesopic conditions is at least 10% compared to the pupil diameter of the patient under the same mesopic conditions but not having received the therapy defined by the method. In certain other embodiments, the reduction in pupil diameter under mesopic conditions is at least 20% compared to the pupil diameter of the patient under the same mesopic conditions but not having received the therapy defined by the method. In certain other embodiments, the reduction in pupil diameter under mesopic conditions is at least 30% compared to the pupil diameter of the patient under the same mesopic conditions but not having received the therapy defined by the method. In certain other embodiments, the patient experiences a reduction in pupil diameter of at least 0.5 mm when measured under mesopic conditions relative to the diameter of the patient's pupil under the same mesopic conditions but not having received the therapy defined by the method. In certain other embodiments, the patient experiences a reduction in pupil diameter ranging from about 0.6 mm to about 3 mm, about 0.6 mm to about 2.5 mm, or about 0.6 mm to about 2 mm when measured under mesopic conditions relative to the diameter of the patient's pupil under the same mesopic conditions but not having received the therapy defined by the method. In certain other embodiments, the patient experiences a reduction in pupil diameter ranging from about 0.6 mm to about 1.2 mm when measured under mesopic conditions relative to the diameter of the patient's pupil under the same mesopic conditions but not having received the therapy defined by the method. In yet other embodiments, the patient's pupil is reduced to a diameter of about 3 mm to about 5 mm, about 3 mm to about 6 mm, about 4 mm to about 5 mm, about 4 mm to about 6 mm, or about 4 mm to about 7 mm under mesopic conditions due to the therapy defined by the method. In certain embodiments, the patient's pupil is reduced to a diameter of about 4 mm to about 6 mm under mesopic conditions due to the therapy defined by the method.

In certain embodiments, the reduction in pupil diameter under photopic conditions is at least 5% compared to the pupil diameter of the patient under the same photopic conditions but not having received the therapy defined by the method. In certain other embodiments, the reduction in pupil diameter under photopic conditions is at least 10% compared to the pupil diameter of the patient under the same photopic conditions but not having received the therapy defined by the method. In certain other embodiments, the reduction in pupil diameter under photopic conditions is at least 20% compared to the pupil diameter of the patient under the same photopic conditions but not having received the therapy defined by the method. In certain other embodiments, the reduction in pupil diameter under photopic conditions is at least 30% compared to the pupil diameter of the patient under the same photopic conditions but not having received the therapy defined by the method. In certain other embodiments, the patient experiences a reduction in pupil diameter of at least 0.5 mm when measured under photopic conditions relative to the diameter of the patient's pupil under the same photopic conditions but not having received the therapy defined by the method. In certain other embodiments, the patient experiences a reduction in pupil diameter ranging from about 0.6 mm to about 3 mm, about 0.6 mm to about 2.5 mm, or about 0.6 mm to about 2 mm when measured under photopic conditions relative to the diameter of the patient's pupil under the same photopic conditions but not having received the therapy defined by the method. In certain other embodiments, the patient experiences a reduction in pupil diameter ranging from about 0.6 mm to about 1.2 mm when measured under photopic conditions relative to the diameter of the patient's pupil under the same photopic conditions but not having received the therapy defined by the method. In yet other embodiments, the patient's pupil is reduced to a diameter of about 3 mm to about 5 mm, about 3 mm to about 6 mm, about 4 mm to about 5 mm, about 4 mm to about 6 mm, or about 4 mm to about 7 mm under photopic conditions due to the therapy defined by the method. In certain embodiments, the patient's pupil is reduced to a diameter of about 4 mm to about 6 mm under photopic conditions due to the therapy defined by the method.

Reduction in pupil diameter can be analyzed and characterized using procedures such as those described below in which a phentolamine mesylate solution was administered to patients' eyes and change in pupil diameter was measured and characterized. This was performed in the context of a clinical study using patients that were at least 18 years old and had a clinical history of pupil sizes of at least 7 mm in diameter under dim light conditions. The phentolamine mesylate solution contained either 0.2% (w/v) phentolamine mesylate, 0.4% (w/v) phentolamine mesylate, or 0.8% (w/v) phentolamine mesylate.

Part I—Experimental Procedures

Sixteen patients were randomized into four groups (of four subjects each). Each group was treated on three successive study visits separated by at least 4 days with one drop of ophthalmic oxymetazoline solution (Visine LR®) in each eye followed by one drop test article in each eye. The test article was a 0.2% (w/v) phentolamine mesylate solution, 0.4% (w/v) phentolamine mesylate solution, 0.8% (w/v) phentolamine mesylate solution, or placebo. Test articles contained the designed amount of phentolamine mesylate in a solution of Tears Naturale II® (from Alcon Labs). Placebo was just Tears Naturale II® (from Alcon Labs). Tears Naturale II® (from Alcon Labs) contains Dextran 70 (0.1% by weight), Hydroxypropyl Methylcellulose 2910 (0.3% by weight), Polyquaternium-1 (0.001% by weight), potassium chloride, water (purified), sodium borate, sodium chloride, and hydrochloric acid and/or sodium hydroxide as necessary to adjust the pH. The patients' pupil diameters were recorded at baseline (i.e., prior to treatment administration), and at 30 minutes, 1 hour, 2 hours, 4 hours, and 8 hours after administration of test articles. Total study duration was approximately nine hours. Treatment group randomization schedules are provided in Table 1 below.

TABLE 1

TREATMENT GROUP RANDOMIZATION SCHEDULES

| | Visit 1 Treatment | Visit 2 Treatment | Visit 3 Treatment |
| --- | --- | --- | --- |
| Group 1 (N = 4) | 0.2% (w/v) phentolamine mesylate solution | 0.4% (w/v) phentolamine mesylate solution | 0.8% (w/v) phentolamine mesylate solution |
| Group 2 (N = 4) | 0.2% (w/v) phentolamine mesylate solution | 0.4% (w/v) phentolamine mesylate solution | placebo |
| Group 3 (N = 4) | 0.2% (w/v) phentolamine mesylate solution | placebo | 0.8% (w/v) phentolamine mesylate solution |
| Group 4 (N = 4) | placebo | 0.4% (w/v) phentolamine mesylate solution | 0.8% (w/v) phentolamine mesylate solution |

Patients were eligible for enrollment if they were (a) at least 18 years of age, and (b) had a documented pupil size in dim light of greater than 7 mm. Patients were ineligible for enrollment in the study if they met any of the following criteria: (a) had moderate to severe hypertension, (b) had a history of heart rate abnormalities, (c) had been administered any investigational drug within 14 days of screening, (d) had a known local or systemic hypersensitivity to adrenergic antagonists, or (e) had central corneal pathology.

Pupil diameters were measured to within 0.1 mm for each eye at baseline and each subsequent time point using a NeurOptics™ pupilometer. Comparisons of changes in mean values within treatment groups were tested for significance using two-tailed paired two sample t-tests with a threshold for significance set at p<0.01 (Bonferroni Correction for multiple paired t-tests). Differences between treatment groups with respect to mean values for pupil size over the course of the study were tested for significance using repeated measure ANOVA (which discards data from subjects lacking any data points). Differences in means between treatment groups at individual time points were tested for significance using one-way ANOVA. If one-way ANOVA showed significance at a given time point, ad hoc Fisher's testing was performed to identify significant differences between individual group means.

Part II—Results

Fifteen of 16 patients completed the study. One patient randomized to Group 3 completed only two of three clinic visits, missing the 0.8% (w/v) phentolamine mesylate dose. The results of pupil measurements are described below.

One criterion for entrance into the study was historical documentation of a pupil size >7 mm when measured under dim light conditions. Table 2 provides the mean pupil diameters, standard deviation of pupil diameters, and the observed range of diameters recorded immediately prior to administration of each treatment.

TABLE 2

BASELINE PUPIL MEASURES

| Pupil Variable | Placebo | 0.2% (w/v) Phentolamine Mesylate | 0.4% (w/v) Phentolamine Mesylate | 0.8% (w/v) Phentolamine Mesylate |
|---|---|---|---|---|
| Sample Size[a] | 24 | 24 | 24 | 22[b] |
| Mean Diameter (mm) | 7.8 | 7.8 | 7.7 | 8.0 |
| Standard Deviation (mm) | 0.6 | 0.9 | 0.7 | 1.1 |
| Range (mm) | 6.5-8.7 | 5.2-8.8 | 5.8-8.6 | 4.6-9.3 |

[a] measurements from each pupil treated separately
[b] one subject missed the 0.8% phentolamine dosing visit Average baseline pupil diameters were comparable across all four treatment groups, with observed differences in means (Table 2) not statistically significant (P=0.766). Of the 94 baseline pupil diameters collected during the study, there were twelve instances (representing 3 subjects; Table 3) in which baseline pupil diameters were less than the inclusion criterion of 7 mm. Baseline pupil diameters less than 7 mm were evenly distributed between treatment groups (2, 3, 4, and 3 pupils in Placebo, 0.2%, 0.4%, and 0.8% (w/v) phentolamine mesylate treatment groups, respectively).

TABLE 3

SUBJECTS WITH BASELINE PUPIL DIAMETERS LESS THAN 7 MM

| | Subject 2 | | Subject 6 | | Subject 16 | |
|---|---|---|---|---|---|---|
| Study Visit | Right Pupil (mm) | Left Pupil (mm) | Right Pupil (mm) | Left Pupil (mm) | Right Pupil (mm) | Left Pupil (mm) |
| 1 | 6.7 | 7.1 | 7 | 7 | 5.8 | 5.7 |
| 2 | 6.7 | 6.5 | 6.8 | 6.3 | 6.3 | 5.8 |
| 3 | 7.9 | 8.2 | 7.4 | 6.7 | 5.5 | 4.6 |

For all study groups, mean pupil diameters were relatively unchanged at 30 minutes after treatment. By one hour post treatment, mean pupil diameters were lower (P=0.47) for phentolamine-treated subjects. Mean pupil diameters for subjects receiving placebo were relatively constant for the 8 hours of post-treatment observation.

TABLE 4

MEAN PUPIL DIAMETERS DURING THE STUDY

| Treatment Group[a] | Baseline | 30 min | 1 hour | 2 hours | 4 hours | 8 hours |
|---|---|---|---|---|---|---|
| Placebo | | | | | | |
| Mean Diameter (mm) | 7.83 | 7.87 | 7.80 | 7.93 | 7.87 | 8.08[b] |
| Standard Deviation | 0.61 | 0.81 | 0.79 | 0.60 | 0.58 | 0.75 |
| Minimum (mm) | 6.5 | 5.5 | 5.9 | 6.5 | 6.8 | 6.5 |
| Maximum (mm) | 8.7 | 9.0 | 9.2 | 9.0 | 9.0 | 9.3 |
| 0.2% (w/v) Phentolamine Mesylate | | | | | | |
| Mean Diameter (mm) | 7.78 | 7.74 | 7.54 | 7.01[c] | 7.30[d] | 7.18 |
| Standard Deviation | 0.88 | 1.02 | 1.02 | 0.82 | 0.51 | 0.90 |
| Minimum (mm) | 5.2 | 5.1 | 4.9 | 4.7 | 6.3 | 4.7 |
| Maximum (mm) | 8.8 | 9.2 | 8.9 | 8.4 | 8.0 | 8.5 |
| 0.4% (w/v) Phentolamine Mesylate | | | | | | |
| Mean Diameter (mm) | 7.71 | 7.72 | 7.41 | 7.05 | 7.01 | 7.01 |
| Standard Deviation | 0.71 | 0.81 | 0.77 | 0.84 | 0.92 | 0.97 |
| Minimum (mm) | 5.8 | 5.6 | 5.5 | 5.0 | 5.0 | 4.8 |
| Maximum (mm) | 8.6 | 8.8 | 8.3 | 8.4 | 8.1 | 8.6 |
| 0.8% (w/v) Phentolamine Mesylate[e] | | | | | | |
| Mean Diameter (mm) | 7.96 | 7.87 | 7.69 | 7.30 | 7.32 | 7.40 |
| Standard Deviation | 1.10 | 0.97 | 0.97 | 0.99 | 0.99 | 0.99 |
| Minimum (mm) | 4.6 | 5.2 | 5.1 | 4.7 | 5.5 | 4.7 |
| Maximum (mm) | 9.3 | 9.2 | 9.1 | 8.7 | 8.6 | 8.7 |

[a] 24 pupils per sample except where noted
[b] 20 pupils; 8 hour data for subjects 2 and 11, visit 2, were not recorded
[c] 22 pupils; 2 hour data from subject 7, visit 1 not recorded
[d] 22 pupils; 4 hour data from subject 16, visit 1 not recorded
[e] 22 pupils at each time point, subject 16 missed visit 3

Repeated measures ANOVA showed a significant (p<0.001) difference between treatment groups with respect to pupil diameter over the course of the study. Significant differences in mean pupil diameters between treatment were identified by one-way ANOVA at 2 hours (p=0.0006), 4 hours (p=0.0027) and 8 hours (p=0.0016) after treatment. Ad hoc Fisher's tests of significance between individual group means demonstrated significant differences in mean pupil diameters of subjects treated with any concentration of phentolamine mesylate when compared to placebo at 2, 4 and 8 hours (Table 5). In contrast, there were no statistically significant differences in mean pupil diameters observed between different doses of phentolamine at any time point.

TABLE 5

SIGNIFICANCE OF DIFFERENCES BETWEEN MEAN PUPIL DIAMETERS

| Treatment Comparison | 2 hours | 4 hours | 8 hours |
|---|---|---|---|
| Placebo vs. 0.2% (w/v) Phentolamine Mesylate | P = 0.0003 | P = 0.0147 | P = 0.0018 |
| Placebo vs. 0.4% (w/v) Phentolamine Mesylate | P = 0.0003 | P = 0.0002 | P = 0.0002 |
| Placebo vs. 0.8% (w/v) Phentolamine Mesylate | P = 0.0110 | P = 0.0200 | P = 0.0199 |

*-Fisher's Ad Hoc test of means for time points previously shown to be significant by One-Way ANOVA For all treatment groups, mean pupil diameters were relatively unchanged from baseline at 30 minutes after treatment (Table 6). By one hour post treatment, change from baseline in mean pupil diameters was significant (p<0.01) for subjects treated with 0.2% (w/v), 0.4% (w/v), and 0.8% (w/v) phentolamine mesylate. Mean pupil diameters did not significantly change from baseline for subjects receiving placebo over the 8 hours of post-treatment observation.

Differences in mean pupil diameters of treatment groups are expressed as mean changes in diameter from baseline in Table 6. When mean changes in pupil diameters from baseline are evaluated as a function of time, it is apparent that those subjects receiving phentolamine mesylate experienced significant reductions in pupil size over the course of the study.

TABLE 6

MEAN PUPIL DIAMETER CHANGES
FROM BASELINE OVER TIME

| Treatment Group | 30 min | 1 hour | 2 hours | 4 hours | 8 hours |
|---|---|---|---|---|---|
| Placebo | | | | | |
| Mean Change (mm) | 0.04 | −0.03 | 0.10 | 0.04 | 0.12 |
| Standard Deviation | 0.32 | 0.36 | 0.34 | 0.51 | 0.35 |
| Sample Size (pupils) | 24 | 24 | 24 | 24 | 20 |
| P-value[a] | 0.57 | 0.66 | 0.15 | 0.72 | 0.15 |
| 0.2% (w/v) Phentolamine Mesylate | | | | | |
| Mean Change (mm) | −0.04 | −0.24 | −0.75 | −0.69 | −0.59 |
| Standard Deviation | 0.33 | 0.37 | 0.51 | 0.49 | 0.62 |
| Sample Size (pupils) | 24 | 24 | 22 | 22 | 24 |
| P-value[a] | 0.58 | <0.005 | <0.001 | <0.001 | <0.001 |
| 0.4% (w/v) Phentolamine Mesylate | | | | | |
| Mean Change (mm) | 0.00 | −0.29 | −0.64 | −0.74 | −0.74 |
| Standard Deviation | 0.40 | 0.33 | 0.46 | 0.45 | 0.47 |
| Sample Size (pupils) | 22 | 22 | 22 | 22 | 22 |
| P-value[a] | 0.86 | <0.001 | <0.001 | <0.001 | <0.001 |
| 0.8% (w/v) Phentolamine Mesylate | | | | | |
| Mean Change (mm) | −0.10 | −0.27 | −0.66 | −0.64 | −0.56 |
| Standard Deviation | 0.31 | 0.43 | 0.44 | 0.61 | 0.43 |
| Sample Size (pupils) | 22 | 22 | 22 | 22 | 22 |
| P-value[a] | 0.16 | <0.007 | <0.001 | <0.001 | <0.001 |

[a]Two-sided paired two-sample t-test.
$P < 0.01$ is significant by Bonferroni correction Impact on Distance Vision Acuity in the Patient's Eye The methods may be further characterized according to whether there is an adverse impact on distance vision acuity in the patient's eye due to the method. In certain embodiments, distance vision acuity of the patient is not reduced.

Administer Dosage to One or Both of the Patient's Eyes

The methods may be further characterized according to whether the alpha-adrenergic antagonist is administered to one or both of the patient's eyes. In certain embodiments, the dosage is administered to only one eye in the patient. In certain embodiments, the dosage is administered to both eyes in the patient.

Reducing Aberrant Focus of Scattered Light Rays in a Patient's Eye

One benefit of the therapeutic methods is that the patient may experience a reduction in aberrant focus of scattered light rays in the patient's eye. This can provide improvement in visual performance for the patient. In certain embodiments, the therapeutic method provides a reduction in aberrant focus of scattered light rays in a patient's eye for at least twenty hours. In certain embodiments, the therapeutic method provides a reduction aberrant focus of scattered light rays in a patient's eye for at least twenty-four hours. In yet other embodiments, the therapeutic method provides a reduction aberrant focus of scattered light rays in a patient's eye for at least thirty-six hours, forty-eight hours, sixty hours, or seventy-two hours.

Implantable Ocular Device

Compositions described herein may be administered to the patient's eye via an implantable ocular device that dispenses the composition. The implantable ocular device may be configured to dispense the composition at a desired rate and/or frequency. In certain embodiments, the implantable ocular device is a slow release insert.

III. Ophthalmic Solutions

Therapeutically active agents are desirably administered to the eye of the patient in the form of an ophthalmic solution. Such an ophthalmic solution comprises one or more therapeutically active agents and a pharmaceutically acceptable carrier. Desirably, the ophthalmic solution exhibits good storage stability to permit distribution of the ophthalmic solution through normal distribution channels for pharmaceuticals. In certain embodiments, the pharmaceutically acceptable carrier is water. Additional components may be added to the ophthalmic solution in order to optimize performance properties of the ophthalmic solution. Exemplary additional components include, for example, a chelating agent (e.g., EDTA), polyol compound, poly($C_{2-4}$alkylene)glycol polymer, dextran, cellulose agent, buffer, tonicity modifier, preservative, antioxidant, viscosity modifying agent, corneal permeation enhancing agent, solubilizing agent, stabilizing agent, surfactant, demulcent polymer, wetting agent, and other materials.

Ophthalmic solutions may be further characterized according to the presence or absence of one or more of a chelating agent (e.g., EDTA), polyol compound, poly($C_{2-4}$alkylene)glycol polymer, dextran, cellulose agent, buffer, tonicity modifier, preservative, antioxidant, viscosity modifying agent, corneal permeation enhancing agent, solubilizing agent, stabilizing agent, surfactant, demulcent polymer, wetting agent, and other materials. In certain embodiments, the ophthalmic solution does not contain a chelating agent (e.g., EDTA). In certain embodiments, the ophthalmic solution does not contain a preservative. In certain embodiments, the ophthalmic solution does contain a preservative.

Various therapeutic methods above involve administering a dosage of phentolamine or a pharmaceutically acceptable salt thereof to the patient. The dosage of phentolamine or a pharmaceutically acceptable salt thereof is desirably in the form of an ophthalmic solution. The ophthalmic solution is formulated to be suitable for administration to the eye of a patient, and desirably provides immediate release of phentolamine, that is, the ophthalmic solution is not a sustained release formulation that delivers phentolamine over an extended duration, such as hours, days or weeks.

The ophthalmic solution desirably comprises an aqueous pharmaceutically acceptable carrier and phentolamine or a pharmaceutically acceptable salt thereof. The ophthalmic solution may contain excipients(s) that are suitable for administration to the eye. Various pharmaceutically acceptable salts are described in the literature. The preferred salt form of phentolamine is phentolamine mesylate. Accordingly, the methods may use an ophthalmic solution that comprises an aqueous pharmaceutically acceptable carrier and phentolamine mesylate.

Accordingly, in certain embodiments, the dosage utilized in the methods is an ophthalmic solution comprising an aqueous pharmaceutically acceptable carrier and phentolamine or a pharmaceutically acceptable salt thereof. In certain other embodiments, the dosage is an ophthalmic solution comprising an aqueous pharmaceutically acceptable carrier and phentolamine mesylate. In certain other embodiments, the dosage is an ophthalmic solution comprising water, a polyol, and phentolamine or a pharmaceutically acceptable salt thereof. In certain other embodiments, the dosage is an ophthalmic solution comprising water, mannitol, and phentolamine mesylate. In certain other embodiments, the dosage is an ophthalmic solution comprising water, a polyol, an alkali metal carboxylate, and phentolamine or a pharmaceutically acceptable salt thereof.

In certain other embodiments, the dosage is an ophthalmic solution comprising water, mannitol, sodium acetate, and phentolamine mesylate.

Other ophthalmic solutions that are contemplated for use in the present invention include, for example, (i) aqueous ophthalmic solutions free of a chelating agent, and (ii) polyvinylpyrrolidone artificial tears formulations, each of which are described in more detail below.

Ophthalmic solutions may be further characterized according to the viscosity of the solution. In certain embodiments, the ophthalmic solution at a temperature of about 25° C. has a viscosity in the range of 0.9 cP to about 1.1 cP. In certain embodiments, the ophthalmic solution at a temperature of about 25° C. has a viscosity of about 1 cP.

In certain embodiments, the ophthalmic solution comprises an alpha-adrenergic antagonist (e.g., phentolamine or a pharmaceutically acceptable salt thereof) and one or more additional agents (e.g., pilocarpine) described herein.

Aqueous Ophthalmic Solution Free of a Chelating Agent

In certain embodiments, the dosage utilized in the methods is an aqueous ophthalmic solution free of a chelating agent, wherein said solution comprises (a) phentolamine or a pharmaceutically acceptable salt thereof; (b) at least one polyol compound, such as a polyol compound having a molecular weight less than 250 g/mol; (c) at least one buffer; and (d) water; wherein the solution does not contain a chelating agent. The amount of ingredients in the aqueous ophthalmic solutions may be selected in order to achieve particular performance properties, such as stability to storage, minimize irritation to the eye of a patient, and enhance penetration of phentolamine into the eye of a patient.

One exemplary preferred solution is an aqueous ophthalmic solution free of a chelating agent comprising: (a) about 0.1% (w/v) to about 4% (w/v) of phentolamine or a pharmaceutically acceptable salt thereof; (b) about 1% (w/v) to about 6% (w/v) of at least one polyol compound having a molecular weight less than 250 g/mol; (c) about 0.1 mM to about 10 mM of at least one buffer; and (d) water; wherein the solution has a pH in the range of 4.0 to 7.5 and does not contain a chelating agent.

Exemplary components and features of the aqueous ophthalmic solutions are described in more detail below.

Phentolamine & Pharmaceutically Acceptable Salts

The aqueous ophthalmic solution comprises phentolamine or a pharmaceutically acceptable salt of phentolamine. Exemplary pharmaceutically acceptable salts include, for example, the hydrochloric acid salt and mesylate salt. Accordingly, in certain embodiments, the solution comprises phentolamine (i.e., as the free base). In certain other embodiments, the solution comprises phentolamine hydrochloride. In certain yet other embodiments, the solution comprises phentolamine mesylate.

The amount of phentolamine or a pharmaceutically acceptable salt thereof in the aqueous ophthalmic solution may be adjusted in order to achieve desired performance properties. For example, where is it desired to provide a larger amount of phentolamine (or pharmaceutically acceptable salt thereof) to the patient in a single administration of the aqueous ophthalmic solution, the concentration of phentolamine (or pharmaceutically acceptable salt thereof) is increased in the aqueous ophthalmic solution. Single administration of aqueous ophthalmic solutions having a higher concentration of phentolamine (or pharmaceutically acceptable salt thereof) may provide the patient with reduced intraocular pressure for a longer duration of time because more phentolamine (or pharmaceutically acceptable salt thereof) is administered to the patient.

Accordingly, in certain embodiments, the aqueous ophthalmic solution comprises from about 0.1% (w/v) to about 5% (w/v) of phentolamine or a pharmaceutically acceptable salt thereof. In certain embodiments, the aqueous ophthalmic solution comprises from about 0.1% (w/v) to about 1% (w/v) of phentolamine or a pharmaceutically acceptable salt thereof, about 1% (w/v) to about 2% (w/v) of phentolamine or a pharmaceutically acceptable salt thereof, about 2% (w/v) to about 3% (w/v) of phentolamine or a pharmaceutically acceptable salt thereof, about 3% (w/v) to about 4% (w/v) of phentolamine or a pharmaceutically acceptable salt thereof, about 4% (w/v) to about 5% (w/v) of phentolamine or a pharmaceutically acceptable salt thereof. In certain embodiments, the aqueous ophthalmic solution comprises from about 0.1% (w/v) to about 2% (w/v) of phentolamine or a pharmaceutically acceptable salt thereof. In certain embodiments, the aqueous ophthalmic solution comprises from about 0.25% (w/v) to about 2% (w/v) of phentolamine or a pharmaceutically acceptable salt thereof. In certain other embodiments, the aqueous ophthalmic solution comprises from about 0.5% (w/v) to about 2% (w/v) of phentolamine or a pharmaceutically acceptable salt thereof. In certain other embodiments, the aqueous ophthalmic solution comprises from about 0.25% (w/v) to about 1% (w/v) of phentolamine or a pharmaceutically acceptable salt thereof. In certain other embodiments, the aqueous ophthalmic solution comprises about 1% (w/v) of phentolamine or a pharmaceutically acceptable salt thereof. In certain other embodiments, the aqueous ophthalmic solution comprises from about 0.1% (w/v) to about 4% (w/v) of phentolamine mesylate. In certain other embodiments, the aqueous ophthalmic solution comprises from about 0.1% (w/v) to about 2% (w/v) of phentolamine mesylate. In certain other embodiments, the aqueous ophthalmic solution comprises from about 0.25% (w/v) to about 2% (w/v) of phentolamine mesylate. In certain other embodiments, the aqueous ophthalmic solution comprises from about 0.5% (w/v) to about 2% (w/v) of phentolamine mesylate. In certain other embodiments, the aqueous ophthalmic solution comprises from about 0.25% (w/v) to about 1% (w/v) of phentolamine mesylate. In certain other embodiments, the aqueous ophthalmic solution comprises about 1% (w/v) of phentolamine mesylate. In certain other embodiments, the aqueous ophthalmic solution comprises about 0.25% (w/v) or about 0.5% (w/v) of phentolamine mesylate.

Polyol Compounds

The aqueous ophthalmic solution comprises one or more polyol compounds. The polyol compound is an organic compound having at least two hydroxyl groups (e.g., from 2 to about 6 hydroxyl groups). The polyol compound is beneficial to the aqueous ophthalmic solution because, for example, it can increase the stability of the aqueous ophthalmic solution to storage and/or modify the tonicity of the aqueous ophthalmic solution. Exemplary polyol compounds include, for example, mannitol, glycerol, propylene glycol, ethylene glycol, sorbitol, and xylitol.

The aqueous ophthalmic solution may contain a single polyol compound or a mixture of one or more polyol compounds. In other words, the aqueous ophthalmic solution comprises at least one polyol compound. In certain embodiments, the aqueous ophthalmic solution comprises at least one polyol compound that is mannitol, glycerol, propylene glycol, ethylene glycol, sorbitol, or xylitol. In certain other embodiments, the at least one polyol compound is mannitol. In certain other embodiments, the at least one polyol compound is glycerol. In certain other embodiments, the at least one polyol compound is propylene glycol. In certain other embodiments, the at least one polyol compound is mannitol, and the solution further comprises glycerol. In certain other embodiments, the at least one polyol compound is mannitol, and the solution further comprises propylene glycol. In certain other embodiments, the at least one polyol compound is glycerol, and the solution further comprises propylene glycol. In certain other embodiments, the mannitol described in embodiments above is D-mannitol.

The amount of the at least one polyol compound in the aqueous ophthalmic solution may be selected in order to achieve desired performance properties for the solution. The polyol compound may, for example, increase the stability of the solution to storage and/or modify the tonicity of the solution to make it more suitable for administration to the eye of a patient. In certain embodiments, the aqueous ophthalmic solution comprises from about 2% (w/v) to about 5% (w/v) of the at least one polyol compound. In certain other embodiments, the aqueous ophthalmic solution comprises from about 3.5% (w/v) to about 4.5% (w/v) of the at least one polyol compound. In certain other embodiments, the aqueous ophthalmic solution comprises about 4% (w/v) of the at least one polyol compound. In certain other embodiments, the aqueous ophthalmic solution comprises from about 2% (w/v) to about 3% (w/v) mannitol, and about 0.5% (w/v) to about 1.5% (w/v) glycerin. In certain other embodiments, the mannitol described in embodiments above is D-mannitol.

In certain embodiments, the amount of polyol may be selected based on the amount of phentolamine (or pharmaceutically acceptable salt thereof), such that there is an inverse relationship between the amount of phentolamine (or pharmaceutically acceptable salt thereof) and the polyol in order to achieve isotonicity with the eye. For example, in embodiments where the aqueous ophthalmic solution contains about 2% (w/v) phentolamine, mannitol is present in the solution at a concentration of about 3% (w/v). In embodiments where the aqueous ophthalmic solution contains about 1% (w/v) phentolamine, mannitol is present in the solution at a concentration of about 4% (w/v). To further illustrate this principle, in embodiments where the aqueous ophthalmic solution contains about 0.5% (w/v) phentolamine, mannitol may be present in the solution at a concentration of about 4.5% (w/v). In certain embodiments, the mannitol described in embodiments above is D-mannitol.

It is appreciated that the aqueous ophthalmic solution can contain additional ingredients described herein, such as various polymer materials. One such embodiment is an aqueous ophthalmic solution comprising, for example, at least one polyol compound that is propylene glycol, and further comprising polypropylene glycol, such as polypropylene glycol having a weight average molecular weight in the range of about 5,000 g/mol to about 100,000 g/mol.

Poly($C_{2-4}$alkylene)glycol Polymer

The aqueous ophthalmic solution may optionally comprise a poly($C_{2-4}$alkylene)glycol polymer. An exemplary poly($C_{2-4}$alkylene)glycol polymer is polypropylene glycol, such as a polypropylene glycol having a weight average molecular weight in the range of about 5,000 g/mol to about 100,000 g/mol, about 10,000 g/mol to about 50,000 g/mol, or about 50,000 g/mol to about 100,000 g/mol.

Dextran

The aqueous ophthalmic solution may optionally comprise dextran. Dextran is a commercially available, branched polysaccharide comprising glucose molecules. The amount of dextran in the aqueous ophthalmic solution may be selected to achieve certain performance properties. In certain embodiments, the aqueous ophthalmic solution comprises from about 0.01% (w/v) to about 2% (w/v) dextran. In certain other embodiments, the aqueous ophthalmic solution comprises from about 0.01% (w/v) to about 1% (w/v) dextran.

The dextran may be further characterized according to its weight average molecular weight. In certain embodiments, the dextran has a weight average molecular weight in the range of about 65,000 g/mol to about 75,000 g/mol. In certain other embodiments, the dextran has a weight average molecular weight of about 70,000 g/mol. In yet other embodiments, the dextran has a weight average molecular weight in the range of about 5,000 g/mol to about 100,000 g/mol, about 10,000 g/mol to about 50,000 g/mol, or about 50,000 g/mol to about 100,000 g/mol.

Cellulose Agent

The aqueous ophthalmic solution may optionally comprise a cellulose agent. Exemplary cellulose agents include, for example, cellulose, carboxymethyl cellulose, hydroxyethylcellulose, hydroxpropylcellulose, and hydroxypropylmethyl cellulose. In certain embodiments, the cellulose agent is hydroxypropylmethyl cellulose. In certain other embodiments, the cellulose agent is cellulose, carboxymethyl cellulose, hydroxyethylcellulose, or hydroxypropylcellulose. The amount of cellulose agent in the aqueous ophthalmic solution may be selected in order to achieve desired performance properties. For example, in certain embodiments, the aqueous ophthalmic solution comprises from about 0.01% (w/v) to about 2% (w/v) cellulose agent.

The cellulose agent may be further characterized according to its weight average molecular weight. In certain embodiments, the cellulose agent has a weight average molecular weight in the range of about 5,000 g/mol to about 100,000 g/mol, about 10,000 g/mol to about 50,000 g/mol, or about 50,000 g/mol to about 100,000 g/mol.

Buffer

The aqueous ophthalmic solution comprises at least one buffer. The buffer imparts to the solution a buffering capacity, that is, the capacity to neutralize, within limits, either acids or bases (alkali) with relatively little or no change in the original pH. The buffer may be an acid, a base, or a combination of an acid and a base. The buffer may be organic, inorganic, or a combination of organic and inorganic components. It should be understood that the buffer at least partially dissociates in aqueous solution to form a mixture of, e.g., an acid and conjugate base or a base and conjugate acid. For example, the buffer may be a combination of a carboxylic acid and its carboxylate salt (e.g., a combination of acetic acid and sodium acetate). In another embodiment, the buffer may be a combination of an acid and a base, where the acid and the base are not conjugates. For example, the acid may be boric acid and the base may be tris(hydroxymethyl)aminomethane (TRIS).

Exemplary buffers include organic acids (e.g., acetic acid, sorbic acid, and oxalic acid), a borate salt, a hydrogen carbonate salt, a carbonate salt, a gluconate salt, a lactate salt, a phosphate salt, a propionate salt, a perborate salt, tris-(hydroxymethyl)aminomethane (TRIS), bis(2-hydroxyethyl)-imino-tris-(hydroxymethyl)aminoalcohol (bis-tris), N-[2-hydroxy-1,1-bis(hydroxymethyl)ethyl]glycine (tricene), N-[2-hydroxy-1,1-bis(hydroxymethyl)ethyl]glycine, 3-(N-morpholino)propanesulfonic acid, N-(carbamoylmethyl)taurine (ACES), an amino acid, salts thereof, and combinations thereof. It should be understood that the salt form of a buffer may comprise any suitable counterion. For example, the salt form of an acid may comprise an alkali or alkaline earth metal counterion.

The buffer can be characterized according to its strength, i.e., the buffering capacity. The buffering capacity can be tested, for example, by determining the millimoles (mM) of strong acid or base (or respectively, hydrogen or hydroxide ions) required to change the pH of a buffer solution by one unit when added to one liter (a standard unit) of the buffer solution. The buffering capacity generally depends on the type and concentration of the buffer components and can be greater in particular pH ranges. For example, a buffer may have an optimal buffering capacity in a pH range near the $pK_a$ of the buffer, e.g., within about 1 pH unit or within about 2 pH units of the $pK_a$ the buffer. In certain embodiments, the buffer is a weak buffer, such as an alkali metal carboxylate (e.g., sodium acetate).

In certain embodiments, the buffer is a weak acid buffer having one or more of the following characteristics: (a) a pKa of from about 4.0 to about 6.0; more preferably, from about 4.5 to about 5.5; and (b) a lipophilicity value Log P of from about −0.50 to about 1.5; more preferably, from about −0.25 to about 1.35.

The amount of buffer can be adjusted in order to achieve desired performance properties for the aqueous ophthalmic solution. For example, in certain embodiments, the buffer may be present at a concentration of less than about 10 mM, less than about 7 mM, less than about 5 mM, less than about 3 mM, or less than about 2 mM. In some embodiments, the buffer may be present at a concentration of from about 1 mM to about 10 mM, from about 1 mM to about 7 mM, from about 1 mM to about 5 mM, from about 1 mM to about 3 mM, from about 1 mM to about 2 mM, from about 2 mM to about 5 mM, or from about 2 mM to about 3 mM. In yet other embodiments, the buffer is present at a concentration of about 3 mM.

The amount and identity of the buffer may be selected in order to achieve certain performance properties for the aqueous ophthalmic solution. For example, the amount of buffer may impact the quantity of acid that may be neutralized before there is substantial change in the pH of the aqueous ophthalmic solution. Also, the amount of buffer may impact the tonicity of the aqueous ophthalmic solution. Desirably, the quantity and identity of the buffer should be selected in order to minimize any irritation that may be caused by administration of the aqueous ophthalmic solution to the eye of a patient. Accordingly, in certain embodiments, the buffer is present at a concentration in the range of about 2 mM to about 4 mM. In yet other embodiments, the buffer is present at a concentration of about 3 mM. In certain embodiments, the buffer comprises an alkali metal alkylcarboxylate. In certain other embodiments, the buffer comprises an alkali metal acetate. In yet other embodiments, the buffer comprises sodium acetate.

Solution pH

The aqueous ophthalmic solution may be characterized according to the pH of the solution. Desirably, the aqueous ophthalmic solution has a pH in the range of 4.0 to 7.5. In certain embodiments, the aqueous ophthalmic solution has a pH in the range of 4.5 to 7.5. In certain embodiments, the solution has a pH in the range of 4.5 to 6.0. In certain other embodiments, the solution has a pH in the range of 4.5 to 5.5. In yet other embodiments, the solution has a pH in the range of 4.7 to 5.1.

Additional Materials for Aqueous Ophthalmic Solutions

The aqueous ophthalmic solutions may contain additional materials in order to make the composition more suitable for administration to the eye of a patient. Exemplary additional materials are described below and include, for example, a tonicity modifier, preservative, antioxidant, viscosity modifying agent, stabilizing agent, corneal permeation enhancing agent, and surfactants.

A. Tonicity Modifier

The aqueous ophthalmic solution may optionally comprise one or more tonicity modifiers. The tonicity modifier may be ionic or non-ionic. In certain embodiments, the tonicity modifier may be a salt, a carbohydrate, or a polyol. Exemplary tonicity modifiers include alkali metal or alkaline earth metal halides (such as LiBr, LiCl, LiI, KBr, KCl, KI, NaBr, NaCl, NaI, $CaCl_2$, and $MgCl_2$), boric acid, dextran (e.g., Dextran 70), cyclodextrin, dextrose, mannitol, glycerin, urea, sorbitol, propylene glycol, or a combination thereof.

It is appreciated that the tonicity modifier may be added to the aqueous ophthalmic solution in an amount sufficient to provide a desired osmolality. In certain embodiments, the tonicity modifier is present in the aqueous ophthalmic solution in an amount sufficient so that the aqueous ophthalmic solution has an osmolality ranging from about 50 to about 1000 mOsm/kg, from about 100 to about 400 mOsm/kg, from about 200 to about 400 mOsm/kg, or from about 280 to about 380 mOsm/kg. In certain embodiments, a tonicity modifier may be present in an amount ranging from about 0.01% (w/v) to about 7% (w/v), about 0.01% (w/v) to about 5% (w/v), about 0.01% (w/v) to about 1% (w/v), about 0.1% (w/v) to about 1% (w/v), about 0.05% (w/v) to about 5% (w/v), about 0.05% (w/v) to about 0.5% (w/v), about 1% (w/v) to about 3% (w/v), or about 2% (w/v) to about 4% (w/v), of the aqueous ophthalmic solution.

B. Preservative

The aqueous ophthalmic solution may optionally comprise one or more preservatives in order to, for example, reduce or prevent microbial contamination. Exemplary preservatives include quaternary ammonium salts such as polyquaternium-1, cetrimide, benzalkonium chloride, or benzoxonium chloride; alkyl-mercury salts of thiosalicylic acid such as thiomersal, phenylmercuric nitrate, phenylmercuric acetate, or phenylmercuric borate; parabens such as methylparaben or propylparaben; alcohols such as chlorobutanol, benzyl alcohol, phenyl ethanol, cyclohexanol, 3-pentanol, or resorcinol; a peroxide; chlorine dioxide or PURITE; guanidine derivatives such as chlorohexidine gluconate or polyaminopropyl biguanide; and combinations thereof.

The amount of preservative can be adjusted in order to achieve desired performance properties for the aqueous ophthalmic solution. In certain embodiments, the preservative is present in an amount less than about 5% (w/v), 3% (w/v), 1% (w/v), or 0.1% (w/v) of the aqueous ophthalmic solution. In certain other embodiments, the preservative is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

C. Antioxidant

The aqueous ophthalmic solution may optionally comprise one or more antioxidants. Exemplary antioxidants for use in the aqueous ophthalmic solutions described herein include water soluble antioxidants such as ascorbic acid, cysteine hydrochloride, sodium bisulfate, sodium metabisulfite, sodium bisulfite, sodium sulfite, and the like; and oil-soluble antioxidants, such as ascorbyl palmitate, butylated hydroxyanisole (BHA), butylated hydroxytoluene (BHT), lecithin, propyl gallate, alpha-tocopherol, and the like.

The amount of antioxidant can be adjusted in order to achieve desired performance properties for the aqueous ophthalmic solution. In certain embodiments, the antioxidant is present in an amount less than about 5% (w/v), 3% (w/v), 1% (w/v), or 0.1% (w/v) of the aqueous ophthalmic solution. In certain other embodiments, the antioxidant is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

D. Viscosity Modifying Agent

The aqueous ophthalmic solution may optionally comprise one or more viscosity modifying agents. The viscosity modifying agent may be used, for example, to increase the absorption of an active agent or increase the retention time of the aqueous ophthalmic solution in the eye. Exemplary viscosity modifying agents include polyvinylpyrrolidone, methylcellulose, hydroxypropyl methylcellulose, hydroxyethylcellulose, hydroxypropylcellulose, carboxymethylcellulose (CMC) and salts thereof (e.g., CMC sodium salt), gelatin, cellulose glycolate, sorbitol, niacinamide, an alpha-cyclodextran, polyvinyl alcohol, polyethylene glycol, hyaluronic acid, a polysachcharaide, a monosaccharide, and combinations thereof.

The amount of viscosity modifying agent can be adjusted in order to achieve desired performance properties for the aqueous ophthalmic solution. In certain embodiments, the viscosity modifying agent is present in an amount less than about 10% (w/v), 5% (w/v), 3% (w/v), 1% (w/v), or 0.1% (w/v) of the aqueous ophthalmic solution. In certain other embodiments, the viscosity modifying agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution. In certain other embodiments, the viscosity modifying agent is present in an amount sufficient to provide an aqueous ophthalmic solution with a viscosity in the range of about 30 centipoise to about 100 centipoise.

The viscosity modifying agent may be a polymer that results in delayed release of one or more therapeutic agents in the solution. The identity of the polymer may be selected so as to achieve a desired time-release profile for the one or more therapeutic agents.

E. Corneal Permeation Enhancing Agent

The aqueous ophthalmic solution may optionally comprise one or more agents for enhancing corneal permeation of phentolamine (or a pharmaceutically acceptable salt thereof). Exemplary agents for enhancing corneal permeation include polymers, organic acids, esters of an organic acid (e.g., a monoglyceride of fatty acid having 8 to 12 carbon atoms), cyclodextrin, benzalkonium chloride (BAK), EDTA, caprylic acid, citric acid, boric acid, sorbic acid, polyoxyethylene-20-stearyl ether (PSE), polyethoxylated castor oil (PCO), deoxycholic acid sodium salt (DC), cetylpyridinium chloride (CPC), laurocapram, hexamethylenelauramide, hexamethyleneoctanamide, decylmethylsulfoxide, methyl sulfone, dimethyl sulfoxide, and combinations thereof.

The amount of corneal permeation enhancing agent can be adjusted in order to achieve desired performance properties for the aqueous ophthalmic solution. In certain embodiments, the corneal permeation enhancing agent is present in an amount less than about 10% (w/v), 5% (w/v), 1% (w/v), or 0.1% (w/v) of the aqueous ophthalmic solution. In certain other embodiments, the corneal permeation enhancing agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), about 0.05% (w/v) to about 0.5% (w/v), about 1% (w/v) to about 3% (w/v), or about 2% (w/v) to about 4% (w/v), of the aqueous ophthalmic solution.

F. Solubilizing Agent

The aqueous ophthalmic solution may optionally comprise one or more solubilizing agents to improve the solubility of phentolamine (or a pharmaceutically acceptable salt thereof) in the aqueous ophthalmic solution. Exemplary solubilizing agents include, for example, a fatty acid glycerol poly-lower alkylene (i.e., a $C_1$ to $C_7$, linear or branched) glycol ester, fatty acid poly-lower alkylene glycol ester, polyalkylene glycol (e.g., polyethylene glycol), glycerol ether of vitamin E, tocopherol polyethylene glycol 1000 succinate (TPGS), tyloxapol, polysorbate 20, polysorbate 40, polysorbate 60, polysorbate 80, polyoxyethylene/polyoxypropylene surfactants (e.g., Pluronic F-68, F-84 and P-103), cyclodextrin, modified cyclodextrins, and combinations thereof. In certain embodiments, the solubilizing agent is a modified cyclodextrin, such as those marketed under the brand name CAPTISOL®.

The amount of solubilizing agent can be adjusted in order to achieve desired performance properties for the aqueous ophthalmic solution. In certain embodiments, the solubilizing agent is present in an amount less than about 10% (w/v), 5% (w/v), 3% (w/v), 1% (w/v), or 0.1% (w/v) of the aqueous ophthalmic solution. In certain other embodiments, the solubilizing agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

G. Stabilizing Agent

The aqueous ophthalmic solution may optionally comprise one or more stabilizing agents in order to improve the stability of the aqueous ophthalmic solution to storage, etc. Stabilizing agents described in the pharmaceutical literature are contemplated to be amenable for use in the aqueous ophthalmic solutions described herein. Exemplary stabilizing agents include an alcohol (e.g., polyols, such as mannitol, glycerol, propylene glycol, sorbitol, and xylitol), polyalkylene glycols such as polyethylene glycol, polypropylene glycol, polyethylene glycol-nonphenol ether, polyethylene glycol sorbitan monolaurate, polyethylene glycol sorbitan monooleate, polyethylene glycol sorbitan monooleate, polyethylene glycol sterarate, polyethylene glycol polypropylene glycol ether, polyvinyl alcohol, polyvinyl pyrrolidine, ascorbic acid, vitamin E, N-acetylcarnosine (NAC), sorbic acid, and combinations thereof. In certain embodiments, the stabilizing agent is a polymer, such as one of the polymers mentioned above.

The amount of stabilizing agent can be adjusted in order to achieve desired performance properties for the aqueous ophthalmic solution. In certain embodiments, the stabilizing agent is present in an amount less than about 10% (w/v), 5% (w/v), or 1% (w/v) of the aqueous ophthalmic solution. In certain other embodiments, the stabilizing agent is present in an amount ranging from about 0.01% (w/v) to about 5% (w/v), about 0.01% (w/v) to about 1% (w/v), or about 0.01% (w/v) to about 0.1% (w/v) of the aqueous ophthalmic solution.

H. Surfactant

The aqueous ophthalmic solution may optionally comprise one or more surfactants. Exemplary surfactants include Polysorbate 20 (i.e., polyoxyethylene (20) sorbitan monolaurate), Polysorbate 40 (i.e., polyoxyethylene (20) sorbitan monopalmitate), Polysorbate 60 (i.e., polyoxyethylene (20) sorbitan monostearate), Polysorbate 80 (i.e., polyoxyethylene (20) sorbitan monooleate), glyceryl stearate, isopropyl stearate, polyoxyl stearate, propylene glycol stearate, sucrose stearate, polyethylene glycol, a polypropylene oxide, a polypropylene oxide copolymer, Pluronic F68, Pluronic F-84, Pluronic P-103, an alcohol ethoxylate, an alkylphenol ethoxylate, an alkyl glycoside, an alkyl polyglycoside, a fatty alcohol, hydroxypropylmethyl cellulose (HPMC), carboxymethyl cellulose (CMC), cyclodextrin, a polyacrylic acid, phosphatidyl choline, phosphatidyl serine, and combinations thereof.

The amount of surfactant can be adjusted in order to achieve desired performance properties for the aqueous ophthalmic solution. In certain embodiments, the surfactant is present in an amount less than about 10% (w/v), 5% (w/v), 3% (w/v), 1% (w/v), or 0.1% (w/v) of the aqueous ophthalmic solution. In certain other embodiments, the surfactant is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

I. Demulcent Polymers

The aqueous ophthalmic solution may optionally comprise one or more demulcent polymers. Because of their ability to hold large amounts of water, demulcent polymers are useful for coating and moisturizing the cornea of the eye. Exemplary demulcent polymers include cellulose derivatives, dextran 40, dextran 70, gelatin, and liquid polyols.

J. Wetting Agents

The aqueous ophthalmic solution may optionally comprise one or more wetting agents. Wetting agents can be used to wet the surface of the eye. Exemplary wetting agents include polysorbates, poloxamers, tyloxapol, and lecithin.

K. Additional Materials

The aqueous ophthalmic solutions may optionally comprise one or more additional materials, such as acetylcysteine, cysteine, sodium hydrogen sulfite, butyl-hydroxyanisole, butyl-hydroxytoluene, alpha-tocopherol acetate, thiourea, thiosorbitol, sodium dioctyl sulfosuccinate, monothioglycerol, lauric acid sorbitol ester, triethanol amine oleate, or palmitic acid esters.

Further, the aqueous ophthalmic solutions may comprise a carrier, such as one or more of the exemplary carriers are described in for example, Martin, Remington's Pharmaceutical Sciences, 15th Ed., Mack Publ. Co., Easton, PA [1975]). The carrier can be, for example, a mixture of water and a water-miscible solvent (e.g., an alcohol such as glycerin, a vegetable oil, or a mineral oil). Other exemplary carriers include a mixture of water and one or more of the following materials: hydroxyethylcellulose, carboxymethylcellulose, methylcellulose, an alkali metal salt of carboxymethylcellulose, hydroxymethylcellulose, methylhydroxypropylcellulose, hydroxypropylcellulose, ethyl oleate, polyvinylpyrrolidone, an acrylate polymer, a methacrylate polymer, a polyacrylamide, gelatin, an alginate, a pectin, tragacanth, karaya gum, xanthan gum, carrageenin, agar, acacia, a starch (such as starch acetate or hydroxypropyl starch), polyvinyl alcohol, polyvinyl methyl ether, polyethylene oxide, or a cross-linked polyacrylic acid.

Exemplary Aqueous Ophthalmic Solutions

The aqueous ophthalmic solutions having been generally described above will now be more specifically described by reference to the following more specific examples. The following more specific examples are only exemplary and are not intended to limit the scope of the invention in any way.

One such exemplary solution is an aqueous ophthalmic solution free of a chelating agent comprising: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.25% (w/v) to about 1% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4 to 6.

Another such exemplary solution is an aqueous ophthalmic solution free of a chelating agent comprising: (a) about 0.5% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the at least one polyol is mannitol. In certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about 2% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Another such exemplary solution is an aqueous ophthalmic solution free of a chelating agent comprising: (a) about 0.25% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain other embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about 1% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Further exemplary aqueous ophthalmic solutions are provided in Tables 1-3 below, where in each instance the solution has a pH in the range of 4.7 to 5.1.

TABLE 1

EXEMPLARY AQUEOUS OPHTHALMIC SOLUTIONS.

| Component | Formulation No. | | | | | | | |
|---|---|---|---|---|---|---|---|---|
| | A1 | B1 | C1 | D1 | E1 | F1 | G1 | H1 |
| Phentolamine mesylate (% w/v) | 1.5 | 1 | 0.5 | 1 | 1 | 1 | 1 | 1 |
| Mannitol (% w/v) | 4 | 4 | 4 | 3 | 3 | 2 | 2 | 4 |
| Sodium acetate (mM) | 3 | 3 | 3 | 3 | 3 | 3 | 3 | 3 |
| Glycerol (% w/v) | 0 | 0 | 0 | 0.5 | 0 | 1 | 0 | 0 |
| Propylene glycol (% w/v) | 0 | 0 | 0 | 0 | 0.5 | 0 | 1 | 0 |
| Dextran 70 (% w/v) | 0 | 0 | 0 | 0 | 0 | 0 | 0 | 0.1 |
| Water | q.s. | q.s. | q.s. | q.s. | q.s. | q.s. | q.s. | q.s. |

TABLE 2

EXEMPLARY AQUEOUS OPHTHALMIC SOLUTIONS.

| Component | Formulation No. | | | | | |
|---|---|---|---|---|---|---|
| | A2 | B2 | C2 | D2 | E2 | F2 |
| Phentolamine mesylate (% w/v) | 0.25 | 0.25 | 0.25 | 0.25 | 0.25 | 0.25 |
| Mannitol (% w/v) | 4 | 3 | 3 | 2 | 2 | 4 |
| Sodium acetate (mM) | 3 | 3 | 3 | 3 | 3 | 3 |
| Glycerol (% w/v) | 0 | 0.5 | 0 | 1 | 0 | 0 |
| Propylene glycol (% w/v) | 0 | 0 | 0.5 | 0 | 1 | 0 |
| Dextran 70 (% w/v) | 0 | 0 | 0 | 0 | 0 | 0.1 |
| Water | q.s. | q.s. | q.s. | q.s. | q.s. | q.s. |

TABLE 3

EXEMPLARY AQUEOUS OPHTHALMIC SOLUTIONS.

| Component | Formulation No. | | | | | | | |
|---|---|---|---|---|---|---|---|---|
| | A3 | B3 | C3 | D3 | E3 | F3 | G3 | H3 |
| Phentolamine mesylate (% w/v) | 1.5 | 1 | 0.5 | 0.25 | 1 | 1 | 1 | 1 |
| Mannitol (% w/v) | 4 | 4 | 4 | 4 | 3 | 2 | 2 | 4 |
| Sodium acetate (mM) | 3 | 3 | 3 | 3 | 3 | 3 | 2 | 3 |
| Water | q.s. | q.s. | q.s. | q.s. | q.s. | q.s. | q.s. | q.s. |

Another exemplary aqueous ophthalmic solution comprises phentolamine mesylate (e.g., at 1% w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 1% w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of 4 to 6. In certain other embodiments, the aqueous ophthalmic solution consists of phentolamine mesylate (e.g., at 1% w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of 4.5 to 5.1.

Another exemplary aqueous ophthalmic solution comprises phentolamine mesylate (e.g., at 1% w/v), mannitol (e.g., at 4% w/v), sodium acetate (e.g., at 3 mM), and water, wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 1% w/v), mannitol (e.g., at 4% w/v), sodium acetate (e.g., at 3 mM), and water, wherein the solution has a pH in the range of 4 to 6. In certain embodiments, the aqueous ophthalmic solution comprises phentolamine mesylate at 1% w/v, mannitol 4% w/v, sodium acetate at 3 mM, and water, wherein the solution has a pH in the range of 4.5 to 5.1. In certain other embodiments, the aqueous ophthalmic solution consists of phentolamine mesylate (e.g., at 1% w/v), mannitol (e.g., at 4% w/v), sodium acetate (e.g., at 3 mM), and water, wherein the solution has a pH in the range of 4.5 to 5.1. In certain embodiments, the aqueous ophthalmic solution consists essentially of phentolamine mesylate at 1% w/v, mannitol 4% w/v, sodium acetate at 3 mM, and water, wherein the solution has a pH in the range of 4.5 to 5.1.

Yet another exemplary solution is an aqueous ophthalmic solution free of a chelating agent that comprises: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

Yet another exemplary solution is an aqueous ophthalmic solution free of a chelating agent that comprises: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.1% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.5 to 5.2 and does not contain a chelating agent.

Yet another exemplary solution is an aqueous ophthalmic solution free of a chelating agent that comprises: (a) about 0.5% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.5% (w/v) to about 1% (w/v) of phentolamine mesylate; (b) about 3% (w/v) to about 5% (w/v) of mannitol; (c) about 1 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.1% (w/v) to about 1% (w/v) of phentolamine mesylate; (b) about 4% mannitol; (c) about 3 mM sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.5% (w/v) to about 1% (w/v) of phentolamine mesylate; (b) about 4% mannitol; (c) about 3 mM sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.25% (w/v) to about 2% (w/v) of phentolamine mesylate; (b) about 3% (w/v) to about 5% (w/v) of mannitol; (c) about 2 mM to about 4 mM of a buffer comprising sodium acetate; and (d) water; wherein the solution has a pH in the range of 4.5 to 5.2 and does not contain a chelating agent.

Yet another exemplary solution is an aqueous ophthalmic solution free of a chelating agent that comprises: (a) about 0.5% (w/v) to about 2% (w/v) of phentolamine mesylate; (b) about 3% (w/v) to about 5% (w/v) of mannitol; (c) about 2 mM to about 4 mM of a buffer comprising sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.5% (w/v) to about 1% (w/v) of phentolamine mesylate; (b) about 3% (w/v) to about 5% (w/v) of mannitol; (c) about 1 mM to about 4 mM of a buffer comprising sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.1% (w/v) to about 1% (w/v) of phentolamine mesylate; (b) about 4% mannitol; (c) about 3 mM of a buffer comprising sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.5% (w/v) to about 1% (w/v) of phentolamine mesylate; (b) about 4% mannitol; (c) about 3 mM of a buffer comprising sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.25% (w/v) to about 2% (w/v) of phentolamine mesylate; (b) about 3% (w/v) to about 5% (w/v) of mannitol; (c) about 2 mM to about 4 mM of a buffer comprising sodium acetate; (d) water; and (e) pilocarpine (e.g., from about 0.1% w/w to about 1% w/w pilocarpine); wherein the solution has a pH in the range of 4.5 to 6.0 and does not contain a chelating agent.

Yet another exemplary solution is an aqueous ophthalmic solution free of a chelating agent that comprises: (a) about 0.5% (w/v) to about 2% (w/v) of phentolamine mesylate; (b) about 3% (w/v) to about 5% (w/v) of mannitol; (c) about 2 mM to about 4 mM of a buffer comprising sodium acetate; (d) water; and (e) pilocarpine (e.g., from about 0.1% w/w to about 1% w/w pilocarpine); wherein the solution has a pH in the range of 4.6 to 6.0 and does not contain a chelating agent.

Yet another exemplary solution is an aqueous ophthalmic solution free of a chelating agent that comprises: (a) about 0.5% (w/v) to about 1% (w/v) of phentolamine mesylate; (b) about 3% (w/v) to about 5% (w/v) of mannitol; (c) about 1 mM to about 4 mM of a buffer comprising sodium acetate; (d) water; and (e) pilocarpine (e.g., from about 0.1% w/w to about 1% w/w pilocarpine); wherein the solution has a pH in the range of 4.6 to 6.0 and does not contain a chelating agent.

Yet another exemplary solution is an aqueous ophthalmic solution free of a chelating agent, comprising: (a) about 0.1% (w/v) to about 1% (w/v) of phentolamine mesylate; (b) about 4% mannitol; (c) about 3 mM of a buffer comprising sodium acetate; (d) water; and (e) pilocarpine (e.g., from about 0.1% w/w to about 1% w/w pilocarpine); wherein the solution has a pH in the range of 4.6 to 6.0 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.5% (w/v) to about 1% (w/v) of phentolamine mesylate; (b) about 4% mannitol; (c) about 3 mM of a buffer comprising sodium acetate; (d) water; and (e) pilocarpine (e.g., from about 0.1% w/w to about 1% w/w pilocarpine); wherein the solution has a pH in the range of 4.6 to 6.0 and does not contain a chelating agent.

Yet another exemplary solution is an aqueous ophthalmic solution, comprising: (a) about 0.25% (w/v) to about 2% (w/v) of phentolamine mesylate; (b) about 3% (w/v) to about 5% (w/v) of mannitol; (c) about 2 mM to about 4 mM of a buffer comprising sodium acetate; (d) water; and (e) pilocarpine (e.g., from about 0.1% w/w to about 1% w/w pilocarpine); wherein the solution has a pH in the range of 4.5 to 6.0.

Yet another exemplary solution is an aqueous ophthalmic solution, comprising: (a) about 0.5% (w/v) to about 2% (w/v) of phentolamine mesylate; (b) about 3% (w/v) to about 5% (w/v) of mannitol; (c) about 2 mM to about 4 mM of a buffer comprising sodium acetate; (d) water; and (e) pilocarpine (e.g., from about 0.1% w/w to about 1% w/w pilocarpine); wherein the solution has a pH in the range of 4.6 to 6.0.

Yet another exemplary solution is an aqueous ophthalmic solution, comprising: (a) about 0.5% (w/v) to about 1% (w/v) of phentolamine mesylate; (b) about 3% (w/v) to about 5% (w/v) of mannitol; (c) about 1 mM to about 4 mM of a buffer comprising sodium acetate; (d) water; (e) pilocarpine (e.g., from about 0.1% w/w to about 1% w/w pilocarpine); and (f) glycerol; wherein the solution has a pH in the range of 4.6 to 6.0.

Yet another exemplary solution is an aqueous ophthalmic solution, comprising: (a) about 0.1% (w/v) to about 1% (w/v) of phentolamine mesylate; (b) about 4% mannitol; (c) about 3 mM of a buffer comprising sodium acetate; (d) water; (e) pilocarpine (e.g., from about 0.1% w/w to about 1% w/w pilocarpine); and (f) glycerol; wherein the solution has a pH in the range of 4.6 to 6.0. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution, comprising: (a) about 0.5% (w/v) to about 1% (w/v) of phentolamine mesylate; (b) about 4% mannitol; (c) about 3 mM of a buffer comprising sodium acetate; (d) water; (e) pilocarpine (e.g., from about 0.1% w/w to about 1% w/w pilocarpine); and (f) glycerol; wherein the solution has a pH in the range of 4.6 to 6.0.

Stability Features of Aqueous Ophthalmic Solutions

The aqueous ophthalmic solutions described herein may be further characterized according to their stability features, such as the percentage of phentolamine (or pharmaceutically acceptable salt thereof) that is present in the aqueous ophthalmic solution after storage for a certain length of time. As explained above, one of the benefits of the present aqueous ophthalmic solutions is that they possess good stability over extended periods of time, even though they do not have a chelating agent.

Accordingly, in certain embodiments, the aqueous ophthalmic solution is characterized by less than 2% by weight of the phentolamine or pharmaceutically acceptable salt thereof degrades upon storage of the solution at 25° C. for 12 weeks. In certain other embodiments, the aqueous ophthalmic solution is characterized by less than 2% by weight of the phentolamine or pharmaceutically acceptable salt thereof degrades upon storage at 25° C. for 24 weeks (or 36 weeks or 48 weeks). In yet other embodiments, less than 7% by weight of the phentolamine or pharmaceutically acceptable salt thereof degrades upon storage at 40° C. for 12 weeks (or 24, 36, or 48 weeks). In yet other embodiments, the aqueous ophthalmic solution is characterized by less than 10% by weight of the phentolamine or pharmaceutically acceptable salt thereof degrades upon storage at 25° C. for 18 months, 24 months, or 36 months. In yet other embodiments, the aqueous ophthalmic solution is characterized by less than 10% by weight of the phentolamine or pharmaceutically acceptable salt thereof degrades upon storage at temperature in the range of 2-8° C. for 18 months, 24 months, or 36 months. In yet other embodiments, the aqueous ophthalmic solution is characterized by less than 4% by weight (or preferably less than 3% by weight) of the phentolamine or pharmaceutically acceptable salt thereof degrades upon storage at 25° C. for 18 months, 24 months, or 36 months. In yet other embodiments, less than 10% by weight of the phentolamine or pharmaceutically acceptable salt thereof degrades upon storage at 40° C. for 4, 5, or 6 months.

Polyvinylpyrrolidone Artificial Tears Formulation

Another ophthalmic solution contemplated for use in the present invention is an ophthalmic solution comprising a therapeutic agent (e.g., an alpha-adrenergic antagonist, such as phentolamine or a pharmaceutically acceptable salt thereof) and a polyvinylpyrrolidone artificial tears composition. Exemplary polyvinylpyrrolidone artificial tears compositions are described in, for example, U.S. Pat. Nos. 5,895,654; 5,627,611; and 5,591,426; and U.S. Patent Application Publication No. 2002/0082288, all of which are hereby incorporated by reference. Artificial tears compositions are understood to promote wettability and spread, have good retention and stability on the eye, and desirably do not cause any significant discomfort to the user. Accordingly, an exemplary polyvinylpyrrolidone artificial tear composition comprises: (1) polyvinylpyrrolidone, preferably in the amount of about 0.1-5% by weight of the solution; (2) benzalkonium chloride, preferably in an amount of about 0.01-0.10% by weight of the solution; (3) hydroxypropyl methylcellulose, preferably in an amount of about 0.2-1.5% by weight of the solution; (4) glycerin, preferably in an amount of about 0.2-1.0% by weight of the solution, and (5) water, wherein the composition is an aqueous solution having isotonic properties.

Sustained Release Delivery Systems

When it is desirable to have sustained release of one or more therapeutic agents to the patient, the therapeutic agent(s) may be administered to the patient in the form of a sustained release delivery system. Sustained release delivery systems are described in the published literature. Exemplary sustained release delivery systems include intracanalicular inserts, a slow release contact lens, a bio-erodible IVT insert, and an intracameral insert. Inserts may be biodegradable or non-biodegradable. Exemplary materials described in the literature for use in sustained release delivery systems include a mixture of EVA and PVA polymers, a mixture of silicone and PVA polymer, a mixture of polyimide and PVA polymer, a mixture of PMMA and EVA polymers, PLGA polymer, and liposomes. In certain embodiments, an ophthalmic solution may contain an oil, such as an oil with viscosity high enough to impede removal of the active ingredient from the surface of the eye when an aliquot of the ophthalmic solution is applied to the surface of the eye.

IV. Medical Kits

Another aspect of the invention provides a medical kit comprising, for example, (i) a therapeutic agent described herein, and (ii) instructions for treating presbyopia, mydriasis, and/or other ocular disorders according to methods described herein.

EXAMPLES

The invention now being generally described, will be more readily understood by reference to the following examples, which are included merely for purposes of illustrating certain aspects and embodiments of the present invention, and are not intended to limit the invention.

Example 1—Treatment of Presbyopia by Phentolamine Mesylate in Human Subjects

Ability of phentolamine mesylate to treat a human subject suffering from presbyopia may be evaluated according to a clinical study in which an aqueous ophthalmic solution containing phentolamine mesylate is administered to the eye of a patient, and then the patient is evaluated for improvement in visual performance, including near-visual visual performance. Experimental procedures and results are described below Part I—Experimental Procedures Human subjects are screened for potential enrollment and, if qualified, enrolled in the study. Exemplary inclusion criteria and exclusion criteria for the study are set forth below. If a subject does not meet the inclusion/exclusion criteria but the investigator believes the subject should be in the study, a deviation may be allowed following a discussion between the Principal Investigator and Sponsor of the study.

Inclusion Criteria 45 to 55 years of age.
 Distance Corrected Near Visual Acuity worse than 20/40.
 Best Corrected Distance Visual Acuity of 20/20 or better in each eye.
 Able and willing to give informed consent and comply with all protocol mandated procedures.

Exclusion Criteria

Certain pupillary conditions.
 Significant astigmatism, glaucoma, diabetes, cataracts, eye surgery, ocular trauma or accommodative issues.
 Contact lens wear within 3 days prior to and for duration of study.
 Use of a prohibited medication.
 Participation in any investigational study within the past 30 days.

Human subjects enrolled in the study shall randomized into two (or more) Treatment Groups with a 1:1 randomization. The Treatment Groups will receive single doses of either:

Placebo Ophthalmic Solution,
 1% w/w Phentolamine Mesylate Ophthalmic Solution, or
 2% w/w Phentolamine Mesylate Ophthalmic Solution.

Description of the study medications is provided in Table 1.

TABLE 1

Study Medication

| Study Medication | Composition of Study Medication |
| --- | --- |
| Placebo Ophthalmic Solution | 4% w/w mannitol<br>3 mM sodium acetate<br>water<br>pH in the range 4.8 to 5.0 |
| 1% w/w Phentolamine Mesylate Ophthalmic Solution | 1% w/w phentolamine mesylate<br>4% w/w mannitol<br>3 mM sodium acetate<br>water<br>pH in the range 4.8 to 5.0 |
| 2% w/w Phentolamine Mesylate Ophthalmic Solution | 2% w/w phentolamine mesylate<br>4% w/w mannitol<br>3 mM sodium acetate<br>water<br>pH in the range 4.8 to 5.0 |

Doses of study medication are given once daily for one or more weeks. Visual performance will be evaluated, which may include analysis of near-vision visual acuity, Best Corrected Distance Visual Acuity (BCDVA), Distance Corrected Near Vision Acuity (DCNVA), and/or Vision questionnaire.

Example 2—Treatment of Presbyopia by Phentolamine Mesylate in Human Subjects

Ability of phentolamine mesylate to treat a human subject suffering from presbyopia may be evaluated according to a clinical study in which an aqueous ophthalmic solution containing phentolamine mesylate is administered to the eye of a patient, and then the patient is evaluated for improvement in visual performance, including near-visual visual performance. Experimental procedures and results are described below.

Part I—Experimental Procedures

Human subjects are screened for potential enrollment and, if qualified, enrolled in the study. Exemplary inclusion criteria and exclusion criteria for the study are set forth below. If a subject does not meet the inclusion/exclusion criteria but the investigator believes the subject should be in the study, a deviation may be allowed following a discussion between the Principal Investigator and Sponsor of the study.

Inclusion Criteria

Be able and willing to provide written informed consent and sign Health Information Portability and Accountability Act (HIPAA) form prior to any study procedure being performed.
 Be able and willing to follow all instructions and attend study visits.
 Be 48-64 years of age of either sex and any race or ethnicity at visit 1.
 Be an early to moderate presbyope determined by screening monocular best-corrected distance visual acuity (VA) at 45 cm.
 Be able and willing to avoid all disallowed medications for the appropriate washout period and during the study without significant risk to the subject.

Exclusion Criteria

Be a female of childbearing potential who is currently pregnant, nursing or planning a pregnancy.
 Have known contraindications or sensitivity to the use of any of the study medications(s) or their components.
 Have an active ocular infection at visit 1 (bacterial, viral or fungal), positive history of an ocular herpetic infection, preauricular lymphadenopathy, or ongoing, active ocular inflammation (e.g., moderate to severe blepharitis, allergic conjunctivitis, peripheral ulcerative keratitis, scleritis, uveitis) in either eye.
 Have moderate or severe dry eye.
 Have clinically significant abnormal lens findings (e.g., cataract) including early lens changes and/or any evidence of a media opacity in either eye.
 Have dark-adapted pupillometry measurements of <4.0 mm in either eye.
 Have intraocular pressure (IOP) that is less than 5 millimeters of mercury (mmHg) or greater than 22 mmHg in either eye documented at visit 1, or have a prior diagnosis of ocular hypertension or glaucoma or currently being treated with any type of topical IOP lowering (glaucoma) medication at visit 1.
 Have abnormal findings on dilated fundus exam in either eye documented within 3 months of visit 1 or a known history of retinal detachment or clinically significant retinal disease in either eye.
 Have a known history or diagnosis in the past of: iritis, scleritis or uveitis, whether active or inactive.
 Have had surgical intervention (ocular or systemic) within 6 months prior to visit 1, or planned surgical intervention within 30 days after visit 4.
 Have undergone refractive eye surgery (incisional keratotomy, photorefractive keratectomy [PRK], laser in situ keratomileusis [LASIK], laser-assisted sub-epithelial keratectomy [LASEK]), corneal inlay procedures, cataract extraction, or intraocular lens placement.

Use artificial tears or lubricant eye ointment on a daily basis.

Have an inability or refuse to discontinue soft contact lens wear 7 days prior to study visit 1 and rigid gas permeable (RGP) contact lens wear 14 days prior to visit 1 and during the study.

Use any of the following disallowed medications during the 2 weeks (14 days) prior to visit 1 and during the study: (1) narcotic (opiate class) pain medication (e.g., codeine, OxyContin®, Vicodin®, Tramadol®); (2) bladder medication (e.g., Urecholine®, bethanechol); (3) antipsychotics; (4) antidepressants; (5) attention-deficit/hyperactivity disorder (ADHD) medications; (6) alpha-blockers (e.g., tamsulosin, Flomax®, Jayln®, Uroxatral®, Rapaflo®); (7) anticholinergics (e.g., atropine, belladonna, benztropine, dicyclomine, donepezil, hyoscyamine, propantheline, scopolamine, trihexphenidyl); (8) muscarinic receptor agonists or cholinergic agonists (e.g., Salagen®, Evoxac®); (9) over-the-counter (OTC) or prescription antihistamines or decongestants; (10) any prescribed topical ophthalmic medications; or (11) recreational drug use (e.g., marijuana, methadone, heroin, cocaine).

Have a diagnosis of diabetes mellitus or a history of elevated blood sugar.

Have a condition or a situation, which in the Investigator's opinion, may put the subject at increased risk, confound study data, or interfere significantly with the subject's study participation, including but not limited to unstable: cardiovascular, hepatic, renal, respiratory, gastrointestinal, endocrine, immunologic, dermatologic, hematologic, neurologic, or psychiatric disease.

Human subjects enrolled in the study shall randomized into two (or more) Treatment Groups with a 1:1 randomization. The Treatment Groups will receive single doses of either:

Placebo Ophthalmic Solution,
1% w/w Phentolamine Mesylate Ophthalmic Solution, or
2% w/w Phentolamine Mesylate Ophthalmic Solution.

Description of the study medications is provided in Table 1.

TABLE 1

Study Medication

| Study Medication | Composition of Study Medication |
| --- | --- |
| Placebo Ophthalmic Solution | 4% w/w mannitol<br>3 mM sodium acetate<br>water<br>pH in the range 4.8 to 5.0 |
| 1% w/w Phentolamine Mesylate Ophthalmic Solution | 1% w/w phentolamine mesylate<br>4% w/w mannitol<br>3 mM sodium acetate<br>water<br>pH in the range 4.8 to 5.0 |
| 2% w/w Phentolamine Mesylate Ophthalmic Solution | 2% w/w phentolamine mesylate<br>4% w/w mannitol<br>3 mM sodium acetate<br>water<br>pH in the range 4.8 to 5.0 |

Doses of study medication are given once daily for one or more weeks. Visual performance will be evaluated, which may include analysis of near-vision visual acuity, Best Corrected Distance Visual Acuity (BCDVA), Distance Corrected Near Vision Acuity (DCNVA), and/or Vision questionnaire.

One measure of performance is the proportion of subjects with at least a 3 line (15 letter) improvement in the study eye in the measurement of post-treatment monocular best-corrected distance visual acuity at 45 cm compared to baseline monocular best-corrected distance visual acuity at 45 cm up to 7 hours post-treatment.

Another measure of performance is the proportion of subjects with at least a 3 line (15 letter) improvement in the study eye in the measurement of post-treatment near vision acuity compared to baseline, such as at up to 7 hours post-treatment.

Example 3—Reversal of Mydriasis in Human Subjects Using Phentolamine Mesylate

Ability of phentolamine mesylate to reverse pharmacologically induced mydriasis in the eye of normal, healthy human subjects was evaluated according to a randomized, crossover, double-masked, placebo-controlled clinical study. Approximately 32 subjects were enrolled and randomized 1:1 into one of two treatment sequences. All subjects were first administered a mydriatic agent (phenylephrine (2.5% w/w) or tropicamide (1% w/w)) by delivery of an eye drop containing the mydriatic agent to the subject's eyes. Then, approximately one hour after receiving the mydriatic agent, the subject was administered study medication according to Treatment Protocol 1 or Treatment Protocol 2.

In Treatment Protocol 1, the subject received placebo on the first treatment day (Visit 1/Day 1) and received 1% w/w Phentolamine Mesylate Ophthalmic Solution on the second treatment day (Visit 2/Day 8+2 days). In Treatment Protocol 2, the subject received 1% w/w Phentolamine Mesylate Ophthalmic Solution on the first treatment day (Visit 1/Day 1) and received placebo on the second treatment day (Visit 2/Day 8+2 days). The study eye was defined as the eye with the larger pupil diameter at maximum (1 hour after instillation of the mydriatic agent) at Visit 1. If both eyes had the same pupil diameter at maximum, then the study eye was the right eye. This was the study eye for both Visit 1 and Visit 2 assessments.

All treatments were administered to both eyes in the subject. At each visit, pupil diameter, accommodation, near and distance visual acuity (VA) and redness in each eye was measured before (−1 hour/baseline) and 1 hour after (0 minutes/maximum) the mydriatic agent instillation in each eye (i.e., right before the study treatment was administered), and at 30 minutes, 1 hour, 2 hours, 4 hours and 6 hours after treatment dosing. Efficacy and safety were evaluated, which included analysis of reduction in pupil diameter. Further aspects of the experimental procedures and results are described below.

Part I—Experimental Procedures

Human subjects were screened for potential enrollment and, if qualified, enrolled in the study. Inclusion criteria and exclusion criteria for the study are set forth below. Subjects enrolled in the study were randomized in a 1:1 ratio to one of two treatment sequences (the first treatment sequence entailed subjects receiving placebo on the first treatment day and receiving 1% w/w Phentolamine Mesylate Ophthalmic Solution on the second treatment day; the second treatment sequence entailed subjects receiving 1% w/w Phentolamine Mesylate Ophthalmic Solution on the first treatment day and receiving placebo on the second treatment day). Randomization was stratified by mydriatic agent (phenylephrine or tropicamide), with randomization into each stratum capped at approximately 16 subjects (approximately half of the randomized subjects received phenylephrine, half received tropicamide). Subjects received their mydriatic agent 1 hour before treatment. Treatment Visit 1 was on Day 1, when the subject received the first treatment in his/her treatment sequence. Treatment Visit 2 was on Day 8+2 days, when the subject received the second treatment in his/her treatment sequence. Each subject received the same mydriatic agent throughout the study. Efficacy and safety were evaluated as described below. Study medication is listed in Table 1.

TABLE 1

Study Medication

| Study Medication | Composition of Study Medication |
|---|---|
| 1% w/w Phentolamine Mesylate Ophthalmic Solution | 1% w/w phentolamine mesylate<br>4% w/w mannitol<br>3 mM buffer comprising sodium acetate and acetic acid<br>water<br>pH in the range 4.8 to 5.0 |
| Placebo | 4% w/w mannitol<br>3 mM buffer comprising sodium acetate and acetic acid<br>water<br>pH in the range 4.8 to 5.0 |

Inclusion Criteria
 1. Males or females ≥18 and ≤45 years of age with brown irides only.
 2. Otherwise healthy and well-controlled subjects.
 3. Ability to comply with all protocol mandated procedures and to attend all scheduled office visits.
 4. Willing to give written informed consent to participate in this study.

Exclusion Criteria
 1. Clinically significant ocular disease as deemed by the Investigator (e.g., cataract, glaucoma, corneal edema, uveitis, severe keratoconjunctivitis sicca) that might interfere with the study.
 2. Unwilling or unable to discontinue use of contact lenses during treatment visits.
 3. Ocular trauma, ocular surgery or non-refractive laser treatment within the 6 months prior to screening.
 4. Ocular medication of any kind within 30 days of screening, with the exception of a) lid scrubs (which may have been used prior to, but not after screening) or b) lubricating drops for dry eye (preservative-free artificial tears), which were allowed to be used in between the study treatment days.
 5. Recent or current evidence at Screening of ocular infection or inflammation. Current evidence of clinically significant blepharitis, conjunctivitis, or a history of herpes simplex or herpes zoster keratitis at Screening.
 6. History of diabetic retinopathy.
 7. Closed or very narrow angles that in the Investigator's opinion were potentially occludable if the subject's pupil was dilated.
 8. History of any traumatic (surgical or nonsurgical) or non-traumatic condition affecting the pupil or iris (e.g., irregularly-shaped pupil, neurogenic pupil disorder, iris atrophy, iridotomy).
 9. Known allergy or contraindication to any component of the mydriatic agents or the vehicle formulation.
 10. Known hypersensitivity or contra-indication to α- and/or β-adrenoceptor antagonists (e.g. chronic obstructive pulmonary disease or bronchial asthma; abnormally low blood pressure (BP) or heart rate (HR); second or third-degree heart block or congestive heart failure (CHF); severe diabetes).
 11. Clinically significant systemic disease (e.g., uncontrolled diabetes, myasthenia gravis, cancer, hepatic, renal, endocrine or cardiovascular disorders) that might have interfered with the study.
 12. Initiation of treatment with, or any changes to the current dosage, drug or regimen of any topical or systemic adrenergic or cholinergic drugs up to 7 days prior to Screening, or during the study.
 13. Participation in any investigational study within 30 days prior to screening.
 14. Women of childbearing potential who were pregnant, nursing, planning a pregnancy, or not using a medically acceptable form of birth control. Acceptable methods include the use of at least one of the following: intrauterine device (IUD), hormonal (oral, injection, patch, implant, ring), barrier with spermicide (condom, diaphragm), or abstinence. An adult woman was considered to be of childbearing potential unless she was 1 year postmenopausal or 3 months post-surgical sterilization. All females of childbearing potential must have had a negative urine pregnancy test result at Visit 1 Screening and Visit 2 examinations and must have intended to not become pregnant during the study.
 15. Resting HR outside the normal range (50-110 beats per minute) at the Screening Visit. HR was allowed to be repeated only once if outside the normal range following at least a 5-minute rest period in the sitting position.
 16. Hypertension with resting diastolic BP>105 mmHg or systolic BP>160 mmHg at the Screening Visit. BP was allowed to be repeated only once if outside the specified range following at least a 5-minute rest period in the sitting position.

As noted in the exclusion criteria, the following were prohibited during the study:

Use of ocular medication within 30 days of the Screening Visit, or anticipated use during the study, with the exception of lubricating drops for dry eye (preservative-free artificial tears), which were allowed to be used throughout the study.

Initiation of treatment with, or any changes to the dosage, drug, or regimen of any topical or systemic adrenergic or cholinergic drugs up to 7 days prior to Screening, or during the study. A large number of drugs, both prescription and over-the-counter (OTC), contain active ingredients that can affect pupil diameter. This includes many eye drops, such as Visine, that would be used to reduce redness, most cough or cold preparations, antihistamines and bronchodilators, most nose-drops, most blood-pressure medications, many drugs used for migraines, and many other products.

Intermittent use of OTC lubricating drops for dry eye (preservative free artificial tears) was acceptable between treatment visits. However, no other ocular medications (OTC or prescription) were allowed within 30 days of the Screening Visit, or during the study.

Analysis of Efficacy

The primary efficacy endpoint was the change in pharmacologically induced mydriatic (max) pupil diameter (0 minutes) at 2 hours post-treatment in the study eye. The study eye was defined as the eye with the larger pupil diameter at maximum (1 hour after instillation of the mydriatic agent) at Visit 1. If both eyes had the same pupil diameter at maximum, then the study eye was the right eye. This was the study eye for both Visit 1 and Visit 2 assessments.

Secondary efficacy endpoints (for the study eye; for the non-study eye; and for both eyes) included:
 Change (in mm) from max pupil diameter (0 minutes) at each remaining timepoint (30 min, 1 hour, 4 hours, 6 hours).
 Percentage of subjects who achieved a pre-specified reduction of ≥2 mm, ≥3 mm, and ≥4 mm from max pupil diameter at each timepoint (30 min, 1 hour, 2 hours, 4 hours, 6 hours).
 Percentage of subjects who achieved pupil diameter of no more than 0.5 mm above baseline (−1 hour) at each timepoint (0 min, 30 min, 1 hour, 2 hours, 4 hours, 6 hours).
 Change from baseline (−1 hour) in accommodation at each timepoint (0 min, 30 min, 1 hour, 2 hours, 4 hours, 6 hours).
 Percent of subjects with unchanged accommodation from baseline (−1 hour) at each timepoint (0 min, 30 min, 1 hour, 2 hours, 4 hours, 6 hours).
 Change from baseline (−1 hour) in BCDVA at each timepoint (0 min, 30 min, 1 hour, 2 hours, 4 hours, 6 hours).
 Percent of subjects who returned to baseline (−1 hour) BCDVA at each timepoint (0 min, 30 min, 1 hour, 2 hours, 4 hours, 6 hours).
 Change from baseline (−1 hour) in DCNVA at each timepoint (0 min, 30 min, 1 hour, 2 hours, 4 hours, 6 hours).
 Percent of subjects who returned to baseline (−1 hour) DCNVA at each timepoint (0 min, 30 min, 1 hour, 2 hours, 4 hours, 6 hours).
 Change from baseline (−1 hour) in conjunctival hyperemia at each timepoint (30 min, 1 hour, 2 hours, 4 hours, 6 hours), for study eye and non-study eye; in all subjects, in subjects taking LUMIFY® (which is an ophthalmic solution containing brimonidine tartrate (0.025% w/w) marketed by Bausch & Lomb, Inc.), and in subjects not taking LUMIFY®.
 Each efficacy endpoint was analyzed overall and by mydriatic agent.

Assessing, Recording, and Analyzing of Efficacy Parameters

Pupil diameter, accommodation, near and distance visual acuity was measured at the Screening Visit (which was also the same day as Treatment Visit 1) and Treatment Visit 2.
 Pupil diameter was measured with the Neuroptics pupillometer (mm).
 Accommodation was measured by the Near Point Rule (Diopters). Worsening of accommodation was defined as an amplitude decrease of greater than 1 diopter compared to baseline. Unchanged also included improvement in accommodation.
 DCNVA Reading/Near was measured by standard reading card (Original Series Sloan Letter Early Treatment Diabetic Retinopathy Study (ETDRS) card, Log MAR units).
 BCDVA Distance was measured by Standard ETDRS chart (Letters).
 Redness was assessed visually with the CCLRU bulbar redness scale (0-3).

All assessments were conducted under photopic conditions. The photopic lighting conditions were to be kept the same during the 2 treatment visits. Every effort was made to have the same person perform the measurements at all timepoints and at all visits.

Screening/Day 1

Individuals who were potential subjects were contacted by the study center to schedule the Screening visit. This visit occurred the same day as Treatment Visit 1, when the first dose of study treatment was given.

Once subjects arrived at the study center, a member of the study center staff interviewed the individual as to their qualifications for participation in the study, and if the subject wished to continue, the Informed Consent form was signed, and a Screening number was assigned. Screening included an explanation of the study, a medical and ophthalmic history, HR and BP, and a review of prior/concomitant medications. The second step in screening included procedures such as a urine pregnancy test (for females of childbearing potential), IOP assessment and an ophthalmic examination that included biomicroscopy and direct or indirect ophthalmoscopy without dilation.

Treatment Visit 1/Day 1

Treatment Visit 1 was the same day as Screening. Once the subject completed the Screening assessments part of the visit and it was confirmed that he/she met all of the inclusion criteria but none of the exclusion criteria, the visit then transitioned to the Treatment Visit 1 assessments. As part of the Treatment Visit 1, the subject:
 Was randomized to one of two treatment sequences, with randomization stratified by mydriatic agent.
 Received one of two approved mydriatic agents (1% w/w tropicamide or 2.5% w/w phenylephrine) at −1 hour/baseline. The mydriatic agent was administered as a single drop to each eye. If the drop was missed, the Investigator was to give the drop again.
 Received the first of the two study treatments, based on his/her randomized treatment sequence at 0±5 minutes/maximum.
 Was assessed for ocular tolerability at 0±5 minutes/maximum following instillation of study medication.
 Was assessed at −1 hour/baseline, 0±5 minutes/maximum, 30±5 minutes, 1 hour±5 mins, 2 hours±10 mins, 4 hours±15 mins and 6 hours±15 mins relative to study treatment for the following: pupil diameter; BCDVA; DCNVA; accommodation; and conjunctival redness as well as any adverse event (AE).
 Had an IOP assessment at 6 hours±15 mins.
 Was assessed at screening, −1 hour/baseline, 2 hours±10 mins, and 6 hours±15 mins relative to study treatment for HR and BP.

The study eye was defined as the eye with the larger pupil diameter at maximum (1 hour after instillation of the mydriatic agent) at Visit 1. If both eyes had the same pupil diameter at maximum, then the study eye was the right eye. This was the study eye for both Visit 1 and Visit 2 assessments.

As needed, two hours post treatment, subjects were allowed to request the administration of LUMIFY® (which is an ophthalmic solution containing brimonidine tartrate (0.025% w/w) marketed by Bausch & Lomb, Inc.) in the non-study eye (and the site was to record such usage).

Treatment Visit 2/Day 8+2 Days

On Study Day 8+2 Days, the subject returned to the clinic for Treatment Visit 2. As part of the Treatment Visit 2, the subject:
 Underwent a review of concomitant medications and females of childbearing potential received a urine pregnancy test.
 Received the same approved mydriatic agent that he/she received at Treatment Visit 1 (1% tropicamide or 2.5% phenylephrine) at −1 hour/baseline. The mydriatic agent was administered as a single drop to each eye. If the drop was missed, the Investigator was to give the drop again.

Received the second of the two study treatments based on his/her randomized treatment sequence at 0±5 minutes/maximum.

Was assessed for ocular tolerability at 0±5 minutes/maximum following instillation of study medication.

Was assessed at—1 hour/baseline, 0±5 mins minutes/maximum, 30 minutes±5 mins, 1 hour±5 mins, 2 hours±10 mins, 4 hours±15 mins and 6 hours±15 mins relative to study treatment for the following: pupil diameter; BDCVA; DCNVA; accommodation; and conjunctival redness as well as any AEs.

Had an IOP assessment at 6 hours±15 mins.

Was assessed at −1 hour/baseline, 2 hours±10 mins and 6 hours±15 mins relative to study treatment for HR and BP.

As needed, two hours post treatment, subjects were allowed to request the administration of LUMIFY® (which is an ophthalmic solution containing brimonidine tartrate (0.025% w/w) marketed by Bausch & Lomb, Inc.) in the non-study eye and such usage would be recorded.

Unscheduled Visits

An Unscheduled Visit was any visit to the Investigator other than the specific visits requested in the protocol, as possibly required for the subject's ophthalmic condition. The Investigator was to perform all procedures necessary to evaluate the study participant at these visits and record any AEs in the case report form (CRF).

Visit Variation

Visits on Day 8 may be up to 2 days late.

Efficacy Determination

Efficacy was assessed using the full analysis set (FAS) with subjects included in the treatment sequence in which they were randomized, regardless of the treatment sequence they actually received. For the analysis of the primary efficacy endpoint, observed case data was used (no imputation was performed for missing data) for the primary analysis. Confirmatory analyses could have been performed using the all randomized population (ARP), with imputation performed for missing data. For the analysis of the secondary efficacy endpoints, only observed case data was used. If warranted, confirmatory analyses using the ARP with imputation for missing data was also performed for the secondary efficacy endpoints.

For all efficacy endpoints, Baseline for a specific day (Visit 1, Visit 2) was defined as −1 hour prior to treatment. Max timepoint was defined as time 0 minutes, during which maximum pupil diameter was expected.

All efficacy data was summarized by treatment group, study day, and timepoint (−1 hour, 0 minutes, 30 minutes, 1 hour, 2 hours, 4 hours, 6 hours; at Visit 1 and at Visit 2), as appropriate.

The primary efficacy endpoint was the change in pharmacologically induced mydriatic (max) pupil diameter (0 minutes) at 2 hours post-treatment in the study eye. The primary efficacy endpoint was analyzed using analysis of covariance (ANCOVA) with change from max pupil diameter (0 minutes) to 2 hours in mean pupil diameter (mm) as the dependent variable; treatment sequence, subject within treatment sequence, period, treatment and mydriatic agent as factors; and max pupil diameter (0 minutes) as the covariate. The ANCOVA was performed using the FAS, with subjects included in their randomized treatment sequence regardless of the treatment they actually received. Observed case data only was used; that is, missing values were not imputed. The least-squares mean (LSM) and standard error (SE) were provided for both treatment groups, along with the placebo-corrected LSM, its 95% confidence interval (CI) and associated p-value. A confirmatory analysis of the primary efficacy endpoint may have been performed, using the ARP with missing values imputed. In addition, the primary efficacy endpoint was analyzed by mydriatic agent using the same model as above but without mydriatic agent as a factor.

For each of the continuous secondary efficacy endpoints, the same ANCOVA for the primary efficacy endpoint was used, with the respective baseline (−1 hour) value included as the covariate [note that all of the secondary efficacy endpoints were in relation to baseline (−1 hour), whereas the primary efficacy endpoint was in relation to max (0 minute)]. Each ANCOVA was performed using the FAS with subjects included in their randomized treatment sequence regardless of the treatment sequence they actually received. Only observed case data was used; that is, missing values for post-randomization assessments was not imputed. The output from each ANCOVA included the LSM and SE for both treatment groups, along with the placebo-corrected LSM, its 95% CI and associated p-value.

For each of the secondary endpoints related to percent of subjects achieving certain criteria, the analysis was performed using PROC GENMOD with a logit link (generalized linear model), in order to account for the crossover design. The analysis included treatment sequence, subject within treatment sequence, period, treatment, mydriatic agent and the respective baseline, as with the ANCOVA for the continuous endpoints. For each analysis, the percentage of subjects in each treatment group meeting the criteria, the odds ratio (OR) with 95% CI and p-value was provided. For these endpoints, the FAS was used with subjects included in their randomized treatment sequence regardless of the treatment sequence they actually received.

In addition, each secondary efficacy endpoint was analyzed by mydriatic agent using the same model indicated above but without mydriatic agent as a factor.

Analysis of Safety

Assessment of safety was evaluated by:

Conjunctival hyperemia measured with a CCLRU card 4-point scale.

None (0)=Normal Appeared white with a small number of conjunctival blood vessel easily observed.

Mild (+1)=Prominent, pinkish-red color of both the bulbar and palpebral conjunctiva.

Moderate (+2)=Bright, scarlet red color of the bulbar and palpebral conjunctiva.

Severe (+3)=Beefy red with petechiae, dark red bulbar and palpebral conjunctiva with evidence of subconjunctival hemorrhage.

Subjective ocular tolerability measured on a 4-point scale.
0—No discomfort
1—Mild discomfort
2—Moderate discomfort
3—Severe discomfort Intraocular pressure (IOP).

Heart Rate (HR) and blood pressure (BP).

Adverse events.

An adverse event (AE) was any untoward medical occurrence in a patient or clinical study subject administered a study medication (pharmacological/biological product) that did not necessarily have a causal relationship to this medication. An AE could therefore have been any unfavorable and unintended sign (including abnormal laboratory findings), symptom, or disease temporarily associated with the use of the study medication, whether or not related to the study medication. Study medication included the investigational drug under evaluation and the comparator product or vehicle placebo that was given or administered during any phase of the study.

Medical conditions/diseases present before starting the investigational treatment were only considered AEs if they worsened after starting the investigational treatment. Abnormal test results constituted AEs only if they induced clinical signs or symptoms, were considered clinically significant, or required therapy.

Severity of an AE was defined as a qualitative assessment of the level of discomfort of an AE as determined by the Investigator or reported to him/her by the subject. The assessment of severity was made irrespective of study medication relationship or seriousness of the event and was to have been evaluated according to the following scale:

1=Mild: present, but not distressing, and no disruption of normal daily activity.

2=Moderate: discomfort sufficient to reduce or affect normal daily activity.

3=Severe: incapacitating, with inability to work or perform normal daily activity.

A change in severity for a reported AE required an end date for the previous severity and a new start and end date for the new severity. For example, a change in severity could go from mild to severe or from severe to moderate. In either case the start or end dates were to have been recorded.

Part II—Results

Data on the observed reduction in pupil diameter is provided in Tables 1A-1F, 2A-2L, and 3A-3C below. Data characterizing subjects according to change in accommodation is provided in Tables 4A and 4B. Analysis was performed for all subjects and subjects receiving tropicamide (where decreased accommodation was considered likely), but not for phenylephrine (where decreased accommodation was considered unlikely). Data characterizing observed eye redness (conjunctival hyperemia) is provided in Tables 5A through 5E. No subjects in this study requested administration of LUMIFY® (ophthalmic solution containing brimonidine tartrate (0.025% w/w) marketed by Bausch & Lomb, Inc.).

TABLE 1A

Pupil Diameter by Time Point (Full Analysis Set)

| Eye Visit Statistic | 1% w/w Phentolamine Ophthalmic Mesylate Solution (N = 31) | Placebo (N = 31) | 1% w/w Phentolamine Mesylate Ophthalmic Solution vs. Placebo [1] LS Mean Difference (95% CI) | p-value |
|---|---|---|---|---|
| Study Eye Baseline (−1 hour) | | | | |
| n | 31 | 31 | | |
| Mean (SD) | 4.54 (0.785) | 4.45 (0.722) | | |
| Median | 4.48 | 4.33 | | |
| Min, Max | 2.8, 6.5 | 2.9, 6.4 | | |
| Max Time Point (0 Minutes) | | | | |
| n | 31 | 31 | | |
| Mean (SD) | 7.20 (1.128) | 6.97 (1.304) | | |
| Median | 7.41 | 7.42 | | |
| Min, Max | 4.3, 8.8 | 4.5, 8.7 | | |
| 30 Minutes | | | | |
| n | 31 | 31 | | |
| Mean (SD) | 7.13 (1.075) | 6.85 (1.265) | | |
| Median | 7.26 | 7.25 | | |
| Min, Max | 4.3, 8.9 | 4.4, 8.7 | | |

Min = Minimum,

Max = Maximum,

SD = Standard deviation,

LS = Least-squares,

CI = Confidence interval,

SE = Standard error,

LOCF = Least observation carried forward.

[1] From a mixed model with change from max pupil diameter (0 minute) as the dependent variable, treatment sequence, period, treatment and mydriatic agent as fixed effects, subject within treatment sequence as a random effect, and max pupil diameter (0 minutes) as the covariate.

[2] From a test comparing the individual treatment change from baseline LS mean to zero.

[3] The pooled data from the Study Eye and Non-study Eye.

TABLE 1B

Pupil Diameter by Time Point (Full Analysis Set)

| Eye Visit Statistic | 1% w/w Phentolamine Ophthalmic Mesylate Solution (N = 31) | Placebo (N = 31) | 1% w/w Phentolamine Mesylate Ophthalmic Solution vs. Placebo [1] LS Mean Difference (95% CI) | p-value |
|---|---|---|---|---|
| Study Eye 30 Minutes Change from Maximum (0 Minutes) | | | | |
| n | 31 | 31 | | |
| Mean (SD) | −0.07 (0.236) | −0.12 (0.221) | | |
| Median | −0.11 | −0.11 | | |
| Min, Max | −0.5, 0.6 | −0.5, 0.5 | | |
| 30 Minutes Change from Maximum (0 Minutes) Mixed Model [1] | | | 0.06 (−0.05, 0.18) | 0.2705 |
| Least-squares mean (SE) | −0.06 (0.039) | −0.13 (0.039) | | |
| p-value [2] | 0.1169 | 0.0034 | | |

TABLE 1B-continued

Pupil Diameter by Time Point (Full Analysis Set)

| Eye<br>Visit<br>Statistic | 1% w/w<br>Phentolamine<br>Ophthalmic<br>Mesylate<br>Solution<br>(N = 31) | Placebo<br>(N = 31) | 1% w/w<br>Phentolamine<br>Mesylate<br>Ophthalmic<br>Solution vs.<br>Placebo [1]<br>LS Mean<br>Difference<br>(95% CI) | p-value |
|---|---|---|---|---|
| 1 hour | | | | |
| n | 31 | 31 | | |
| Mean (SD) | 6.43 (1.413) | 6.69 (1.358) | | |
| Median | 6.95 | 7.23 | | |
| Min, Max | 3.4, 8.5 | 4.1, 8.5 | | |

Min = Minimum,
Max = Maximum,
SD = Standard deviation,
LS = Least-squares,
CI = Confidence interval,
SE = Standard error,
LOCF = Least observation carried forward.

[1] From a mixed model with change from max pupil diameter (0 minute) as the dependent variable, treatment sequence, period, treatment and mydriatic agent as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 1C

Pupil Diameter by Time Point (Full Analysis Set)

| Eye<br>Visit<br>Statistic | 1% w/w<br>Phentolamine<br>Ophthalmic<br>Mesylate<br>Solution<br>(N = 31) | Placebo<br>(N = 31) | 1% w/w<br>Phentolamine<br>Mesylate<br>Ophthalmic<br>Solution vs.<br>Placebo [1]<br>LS Mean<br>Difference<br>(95% CI) | p-value |
|---|---|---|---|---|
| Study Eye<br>1 hour Change<br>from Maximum<br>(0 Minutes) | | | | |
| n | 31 | 31 | | |
| Mean (SD) | −0.77 (0.530) | −0.28 (0.261) | | |
| Median | −0.65 | −0.24 | | |
| Min, Max | −2.1, −0.1 | −1.0, 0.2 | | |
| 1 hour Change<br>from Maximum<br>(0 Minutes)<br>Mixed Model [1] | | | −0.49<br>(−0.70, −0.28) | <0.0001 |
| Least-squares<br>mean (SE) | −0.77 (0.072) | −0.29 (0.072) | | |
| p-value [2] | <0.0001 | 0.0005 | | |
| 2 hours | | | | |
| n | 31 | 31 | | |
| Mean (SD) | 5.50 (1.497) | 6.31 (1.274) | | |
| Median | 6.03 | 6.84 | | |
| Min, Max | 2.6, 7.6 | 3.6, 8.3 | | |

Min = Minimum,
Max = Maximum,
SD = Standard deviation,
LS = Least-squares,
CI = Confidence interval,
SE = Standard error,
LOCF = Least observation carried forward.

[1] From a mixed model with change from max pupil diameter (0 minute) as the dependent variable, treatment sequence, period, treatment and mydriatic agent as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 1D

Pupil Diameter by Time Point (Full Analysis Set)

| Eye<br>Visit<br>Statistic | 1% w/w<br>Phentolamine<br>Ophthalmic<br>Mesylate<br>Solution<br>(N = 31) | Placebo<br>(N = 31) | 1% w/w<br>Phentolamine<br>Mesylate<br>Ophthalmic<br>Solution vs.<br>Placebo [1]<br>LS Mean<br>Difference<br>(95% CI) | p-value |
|---|---|---|---|---|
| Study Eye<br>2 hours Change<br>from Maximum<br>(0 Minutes) | | | | |
| n | 31 | 31 | | |
| Mean (SD) | −1.70 (0.867) | −0.66 (0.418) | | |
| Median | −1.62 | −0.59 | | |
| Min, Max | −4.0, −0.6 | −1.6, 0.2 | | |
| 2 hours Change<br>from Maximum<br>(0 Minutes)<br>Mixed Model [1] | | | −1.00<br>(−1.31, −0.68) | <0.0001 |
| Least-squares<br>mean (SE) | −1.69 (0.117) | −0.69 (0.117) | | |
| p-value [2] | <0.0001 | <0.0001 | | |

TABLE 1D-continued

Pupil Diameter by Time Point (Full Analysis Set)

| Eye<br>Visit<br>Statistic | 1% w/w<br>Phentolamine<br>Ophthalmic<br>Mesylate<br>Solution<br>(N = 31) | Placebo<br>(N = 31) | 1% w/w<br>Phentolamine<br>Mesylate<br>Ophthalmic<br>Solution vs.<br>Placebo [1]<br>LS Mean<br>Difference<br>(95% CI) | p-value |
|---|---|---|---|---|
| 4 hours | | | | |
| n | 31 | 31 | | |
| Mean (SD) | 4.32 (0.994) | 5.34 (1.069) | | |
| Median | 4.27 | 5.25 | | |
| Min, Max | 2.2, 6.0 | 3.1, 7.6 | | |

Min = Minimum,
Max = Maximum,
SD = Standard deviation,
LS = Least-squares,
CI = Confidence interval,
SE = Standard error,
LOCF = Least observation carried forward.

[1] From a mixed model with change from max pupil diameter (0 minute) as the dependent variable, treatment sequence, period, treatment and mydriatic agent as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 1E

Pupil Diameter by Time Point (Full Analysis Set)

| Eye<br>Visit<br>Statistic | 1% w/w<br>Phentolamine<br>Ophthalmic<br>Mesylate<br>Solution<br>(N = 31) | Placebo<br>(N = 31) | 1% w/w<br>Phentolamine<br>Mesylate<br>Ophthalmic<br>Solution vs.<br>Placebo [1]<br>LS Mean<br>Difference<br>(95% CI) | p-value |
|---|---|---|---|---|
| Study Eye<br>4 hours Change<br>from Maximum<br>(0 Minutes) | | | | |
| n | 31 | 31 | | |
| Mean (SD) | −2.88 (0.999) | −1.63 (0.924) | | |
| Median | −2.87 | −1.65 | | |
| Min, Max | −4.9, −0.9 | −3.4, 0.6 | | |
| 4 hours Change<br>from Maximum<br>(0 Minutes)<br>Mixed Model [1] | | | −1.13<br>(−1.40, −0.87) | <0.0001 |
| Least-squares<br>mean (SE) | −2.83 (0.145) | −1.69 (0.146) | | |
| p-value [2] | <0.0001 | <0.0001 | | |
| 6 hours | | | | |
| n | 31 | 31 | | |
| Mean (SD) | 3.86 (0.748) | 4.52 (0.761) | | |
| Median | 4.01 | 4.36 | | |
| Min, Max | 2.3, 5.6 | 2.9, 6.4 | | |

Min = Minimum,
Max = Maximum,
SD = Standard deviation,
LS = Least-squares,
CI = Confidence interval,
SE = Standard error,
LOCF = Least observation carried forward.

[1] From a mixed model with change from max pupil diameter (0 minute) as the dependent variable, treatment sequence, period, treatment and mydriatic agent as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 1F

Pupil Diameter by Time Point (Full Analysis Set)

| Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Study Eye<br>6 hours Change from<br>Maximum (0 Minutes) | | | | |
| n | 31 | 31 | | |
| Mean (SD) | −3.34 (1.155) | −2.45 (1.216) | | |
| Median | −3.55 | −2.67 | | |
| Min, Max | −5.4, −1.1 | −4.5, 0.2 | | |
| 6 hours Change from<br>Maximum (0 Minutes)<br>Mixed Model [1] | | | −0.70 (−0.95, −0.45) | <0.0001 |
| Least-squares mean (SE) | −3.24 (0.132) | −2.54 (0.133) | | |
| p-value [2] | <0.0001 | <0.0001 | | |

Min = Minimum, Max = Maximum, SD = Standard deviation, LS = Least-squares, CI = Confidence interval, SE = Standard error, LOCF = Least observation carried forward.
[1] From a mixed model with change from max pupil diameter (0 minute) as the dependent variable, treatment sequence, period, treatment and mydriatic agent as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2A

Pupil Diameter by Time Point and Mydriatic Agent (Full Analysis Set)

| Mydratic Agent<br>Eye<br>Visit<br>Statistic | 1% w/w Phentolamine Mesylate Ophthalmic Solution<br>(N = 31) | Placebo<br>(N = 31) | 1% w/w Phentolamine Mesylate Ophthalmic Solution vs. Placebo [1]<br>LS Mean Difference (95% CI) | p-value |
|---|---|---|---|---|
| Phenylephrine | | | | |
| Study Eye | | | | |
| Baseline (−1 hour) | | | | |
| n | 15 | 15 | | |
| Mean (SD) | 4.56 (0.847) | 4.32 (0.642) | | |
| Median | 4.50 | 4.32 | | |
| Min, Max | 3.3, 6.5 | 3.3, 5.4 | | |
| Max Time Point (0 Minutes) | | | | |
| n | 15 | 15 | | |
| Mean (SD) | 6.44 (1.097) | 6.06 (1.288) | | |
| Median | 6.21 | 5.56 | | |
| Min, Max | 4.3, 8.8 | 4.5, 8.7 | | |
| 30 Minutes | | | | |
| n | 15 | 15 | | |
| Mean (SD) | 6.46 (1.029) | 6.00 (1.288) | | |
| Median | 6.40 | 5.53 | | |
| Min, Max | 4.3, 8.6 | 4.4, 8.7 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2B

Pupil Diameter by Time Point and Mydriatic Agent (Full Analysis Set)

| Mydratic Agent<br>Eye<br>Visit<br>Statistic | 1% w/w Phentolamine Mesylate Ophthalmic Solution<br>(N = 31) | Placebo<br>(N = 31) | 1% w/w Phentolamine Mesylate Ophthalmic Solution vs. Placebo [1]<br>LS Mean Difference (95% CI) | p-value |
|---|---|---|---|---|
| Phenylephrine | | | | |
| Study Eye | | | | |
| 30 Minutes Change from Maximum (0 Minutes) | | | | |
| n | 15 | 15 | | |
| Mean (SD) | 0.01 (0.278) | −0.06 (0.261) | | |
| Median | −0.09 | −0.08 | | |
| Min, Max | −0.4, 0.6 | −0.5, 0.5 | | |
| 30 Minutes Change from Maximum (0 Minutes) Mixed Model [1] | | | 0.09 (−0.13, 0.30) | 0.3837 |
| Least-squares mean (SE) | 0.02 (0.069) | −0.07 (0.069) | | |
| p-value [2] | 0.8028 | 0.3228 | | |
| 1 hour | | | | |
| n | 15 | 15 | | |
| Mean (SD) | 5.40 (1.257) | 5.74 (1.339) | | |
| Median | 5.49 | 5.56 | | |
| Min, Max | 3.4, 7.7 | 4.1, 8.5 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2C

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Phenylephrine<br>Study Eye<br>1 hour Change from<br>Maximum (0 Minutes) | | | | |
| n | 15 | 15 | | |
| Mean (SD) | −1.04 (0.602) | −0.32 (0.326) | | |
| Median | −1.00 | −0.24 | | |
| Min, Max | −2.1, −0.2 | −1.0, 0.2 | | |
| 1 hour Change from<br>Maximum (0 Minutes)<br>Mixed Model [1] | | | −0.72 (−1.12, −0.32) | 0.0021 |
| Least-squares mean (SE) | −1.04 (0.130) | −0.32 (0.130) | | |
| p-value [2] | <0.0001 | 0.0278 | | |
| 2 hours | | | | |
| n | 15 | 15 | | |
| Mean (SD) | 4.35 (1.296) | 5.40 (1.264) | | |
| Median | 3.85 | 5.21 | | |
| Min, Max | 2.6, 6.8 | 3.6, 8.3 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2D

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Phenylephrine<br>Study Eye<br>2 hours Change from<br>Maximum (0 Minutes) | | | | |
| n | 15 | 15 | | |
| Mean (SD) | −2.09 (0.972) | −0.65 (0.502) | | |
| Median | −1.86 | −0.49 | | |
| Min, Max | −4.0, −0.7 | −1.6, 0.2 | | |
| 2 hours Change from<br>Maximum (0 Minutes)<br>Mixed Model [1] | | | −1.38 (−1.96, −0.81) | 0.0002 |
| Least-squares mean (SE) | −2.07 (0.202) | −0.69 (0.202) | | |
| p-value [2] | <0.0001 | 0.0053 | | |
| 4 hours | | | | |
| n | 15 | 15 | | |
| Mean (SD) | 3.84 (1.004) | 4.85 (1.154) | | |
| Median | 3.54 | 4.93 | | |
| Min, Max | 2.2, 5.8 | 3.1, 7.6 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2E

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Phenylephrine | | | | |
| Study Eye | | | | |
| 4 hours Change from | | | | |
| Maximum (0 Minutes) | | | | |
| n | 15 | 15 | | |
| Mean (SD) | −2.61 (1.138) | −1.20 (0.961) | | |
| Median | −2.31 | −1.07 | | |
| Min, Max | −4.9, −0.9 | −3.4, 0.6 | | |
| 4 hours Change from | | | −1.18 (−1.57, −0.80) | <0.0001 |
| Maximum (0 Minutes) | | | | |
| Mixed Model [1] | | | | |
| Least-squares mean (SE) | −2.50 (0.238) | −1.32 (0.237) | | |
| p-value [2] | <0.0001 | 0.0001 | | |
| 6 hours | | | | |
| n | 15 | 15 | | |
| Mean (SD) | 3.78 (0.868) | 4.34 (0.687) | | |
| Median | 3.31 | 4.29 | | |
| Min, Max | 2.3, 5.6 | 3.3, 5.8 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2F

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Phenylephrine | | | | |
| Study Eye | | | | |
| 6 hours Change from | | | | |
| Maximum (0 Minutes) | | | | |
| n | 15 | 15 | | |
| Mean (SD) | −2.66 (1.168) | −1.71 (1.229) | | |
| Median | −2.46 | −1.45 | | |
| Min, Max | −4.9, −1.1 | −4.3, 0.2 | | |
| 6 hours Change from | | | −0.62 (−1.02, −0.21) | 0.0059 |
| Maximum (0 Minutes) | | | | |
| Mixed Model [1] | | | | |
| Least-squares mean (SE) | −2.50 (0.206) | −1.88 (0.206) | | |
| p-value [2] | <0.0001 | <0.0001 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2G

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Tropicamide | | | | |
| Study Eye | | | | |
| Baseline (−1 hour) | | | | |
| n | 16 | 16 | | |
| Mean (SD) | 4.51 (0.750) | 4.57 (0.790) | | |
| Median | 4.44 | 4.49 | | |
| Min, Max | 2.8, 6.0 | 2.9, 6.4 | | |
| Max Time Point (0 Minutes) | | | | |
| n | 16 | 16 | | |
| Mean (SD) | 7.91 (0.563) | 7.83 (0.486) | | |
| Median | 7.82 | 7.80 | | |
| Min, Max | 6.8, 8.8 | 7.2, 8.7 | | |
| 30 Minutes | | | | |
| n | 16 | 16 | | |
| Mean (SD) | 7.76 (0.664) | 7.64 (0.504) | | |
| Median | 7.71 | 7.46 | | |
| Min, Max | 6.3, 8.9 | 7.0, 8.5 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2H

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Tropicamide | | | | |
| Study Eye | | | | |
| 30 Minutes Change from | | | | |
| Maximum (0 Minutes) | | | | |
| n | 16 | 16 | | |
| Mean (SD) | −0.14 (0.163) | −0.18 (0.160) | | |
| Median | −0.14 | −0.11 | | |
| Min, Max | −0.5, 0.2 | −0.5, 0.0 | | |
| 30 Minutes Change from | | | | |
| Maximum (0 Minutes) | | | | |
| Mixed Model [1] | | | 0.03 (−0.06, 0.13) | 0.4461 |
| Least-squares mean (SE) | −0.14 (0.041) | −0.18 (0.041) | | |
| p-value [2] | 0.0037 | 0.0007 | | |
| 1 hour | | | | |
| n | 16 | 16 | | |
| Mean (SD) | 7.39 (0.690) | 7.58 (0.505) | | |
| Median | 7.32 | 7.39 | | |
| Min, Max | 5.6, 8.5 | 7.0, 8.4 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero
[3] The pooled data from the Study Eye and Non-study Eye.

TABLE 2I

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Tropicamide | | | | |
| Study Eye | | | | |
| 1 hour Change from | | | | |
| Maximum (0 Minutes) | | | | |
| n | 16 | 16 | | |
| Mean (SD) | −0.51 (0.284) | −0.24 (0.185) | | |
| Median | −0.53 | −0.23 | | |
| Min, Max | −1.2, −0.1 | −0.7, 0.0 | | |
| 1 hour Change from | | | −0.27 (−0.46, −0.08) | 0.0080 |
| Maximum (0 Minutes) | | | | |
| Mixed Model [1] | | | | |
| Least-squares mean (SE) | −0.52 (0.062) | −0.24 (0.062) | | |
| p-value [2] | <0.0001 | 0.0018 | | |
| 2 hours | | | | |
| n | 16 | 16 | | |
| Mean (SD) | 6.57 (0.601) | 7.17 (0.392) | | |
| Median | 6.62 | 7.10 | | |
| Min, Max | 5.4, 7.6 | 6.6, 8.1 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2J

Pupil Diameter by Time Point and Mydriatic Agent (Full Analysis Set)

| Mydriatic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Tropicamide | | | | |
| Study Eye | | | | |
| 2 hours Change from | | | | |
| Maximum (0 Minutes) | | | | |
| n | 16 | 16 | | |
| Mean (SD) | −1.33 (0.569) | −0.66 (0.338) | | |
| Median | −1.01 | −0.66 | | |
| Min, Max | −2.3, −0.6 | −1.3, −0.2 | | |
| 2 hours Change from | | | −0.64 (−0.91, −0.37) | 0.0002 |
| Maximum (0 Minutes) | | | | |
| Mixed Model [1] | | | | |
| Least-squares mean (SE) | −1.32 (0.107) | −0.68 (0.107) | | |
| p-value [2] | <0.0001 | <0.0001 | | |
| 4 hours | | | | |
| n | 16 | 16 | | |
| Mean (SD) | 4.77 (0.763) | 5.81 (0.756) | | |
| Median | 4.74 | 5.73 | | |
| Min, Max | 3.8, 6.0 | 4.2, 6.8 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2K

Pupil Diameter by Time Point and Mydriatic Agent (Full Analysis Set)

| Mydratic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Tropicamide | | | | |
| Study Eye | | | | |
| 4 hours Change from | | | | |
| Maximum (0 Minutes) | | | | |
| n | 16 | 16 | | |
| Mean (SD) | −3.14 (0.801) | −2.02 (0.710) | | |
| Median | −3.01 | −2.12 | | |
| Min, Max | −4.7, −1.8 | −3.2, −0.6 | | |
| 4 hours Change from<br>Maximum (0 Minutes)<br>Mixed Model [1] | | | −1.08 (−1.48, −0.69) | <0.0001 |
| Least-squares mean (SE) | −3.12 (0.183) | −2.03 (0.183) | | |
| p-value [2] | <0.0001 | <0.0001 | | |
| 6 hours | | | | |
| n | 16 | 16 | | |
| Mean (SD) | 3.94 (0.635) | 4.68 (0.812) | | |
| Median | 4.04 | 4.45 | | |
| Min, Max | 2.9, 5.3 | 2.9, 6.4 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 2L

Pupil Diameter by Time Point and Mydriatic Agent (Full Analysis Set)

| Mydratic Agent<br>Eye<br>Visit<br>Statistic | 1% w/w Phentolamine<br>Mesylate Ophthalmic<br>Solution<br>(N = 31) | Placebo<br>(N = 31) | 1% w/w Phentolamine<br>Mesylate Ophthalmic<br>Solution vs. Placebo [1]<br>LS Mean Difference<br>(95% CI) | p-value |
|---|---|---|---|---|
| Tropicamide | | | | |
| Study Eye | | | | |
| 6 hours Change from | | | | |
| Maximum (0 Minutes) | | | | |
| n | 16 | 16 | | |
| Mean (SD) | −3.97 (0.714) | −3.15 (0.699) | | |
| Median | −3.78 | −3.14 | | |
| Min, Max | −5.4, −2.8 | −4.5, −1.9 | | |
| 6 hours Change from<br>Maximum (0 Minutes)<br>Mixed Model [1] | | | −0.79 (−1.14, −0.43) | 0.0004 |
| Least-squares mean (SE) | −3.95 (0.175) | −3.16 (0.175) | | |
| p-value [2] | <0.0001 | <0.0001 | | |

Min = Minimum, Max = Maximum, SD = Standard deviation, LS = Least-squares, CI = Confidence interval, SE = Standard error.
[1] From a mixed model with change from max pupil diameter (0 minute) as the dependent variable, treatment sequence, period, and treatment as fixed effects, subject within treatment sequence as a random effect, and max pupil diameter (0 minutes) as the covariate.
[2] From a test comparing the individual treatment change from baseline LS mean to zero.
[3] The pooled data from the Study Eye and Non-study Eye.

TABLE 3A

Percent of Subjects Achieving Pupil Diameter No More Than 0.5 mm Above Baseline by Time Point (Full Analysis Set)

| Eye Visit Category | 1% w/w Phentolamine Mesylate Ophthalmic Solution (N = 31) n (%) | Placebo (N = 31) n (%) | 1% w/w Phentolamine Mesylate Ophthalmic Solution vs. Placebo [1] Odds Ratio (95% CI) | p-value |
|---|---|---|---|---|
| Both Eyes [2] 4 hours | | | | |
| n | 31 | 31 | | |
| <=0.5 mm above Baseline (−1 hour) | 28 (90.3) | 14 (45.2) | 18.28 (6.92, 48.26) | <0.0001 |

CI = Confidence interval. A reduction was determined using the change from baseline (−1 hour) in pupil diameter. Percentages are the number of subjects with no more than 0.5 mm above Baseline (−1 hour), divided by the number of subjects with an assessment at the time point.
[1] From a generalized estimating equations model with a logit link, with reduction achievement (yes/no) as the dependent variable, treatment sequence, period, treatment, and mydriatic agent as fixed effects, subject within treatment sequence as a random effect, and baseline pupil diameter (−1 hour) as the covariate.
[2] The pooled data from the Study Eye and Non-study Eye.

TABLE 3B

Percent of Subjects Achieving Pupil Diameter No More Than 0.5 mm Above Baseline by Time Point and Mydriatic Agent (Full Analysis Set)

| Mydratic Agent Eye Visit Category | 1% w/w Phentolamine Mesylate Ophthalmic Solution (N = 31) n (%) | Placebo (N = 31) n (%) | 1% w/w Phentolamine Mesylate Ophthalmic Solution vs. Placebo [1] Odds Ratio (95% CI) | p-value |
|---|---|---|---|---|
| Phenylephrine Both Eyes [2] 2 hours | '" | | | |
| n | 15 | 15 | | |
| <=0.5 mm above Baseline (−1 hour) | 12 (80.0) | 7 (46.7) | 5.32 (1.26, 22.52) | 0.0231 |

CI = Confidence interval. A reduction was determined using the change from baseline (−1 hour) in pupil diameter.
Percentages are the number of subjects with no more than 0.5mm above Baseline (−1 hour), divided by the number of subjects with an assessment at the time point.
[1] From a generalized estimating equations model with a logit link, with reduction achievement (yes/no) as the dependent variable, treatment sequence, period, and treatment as fixed effects, subject within treatment sequence as a random effect, and baseline pupil diameter (−1 hour) as the covariate.
[2] The pooled data from the Study Eye and Non-study Eye.

TABLE 3C

Percent of Subjects Achieving Pupil Diameter No More Than 0.5 mm Above Baseline by Time Point and Mydriatic Agent (Full Analysis Set)

| Mydratic Agent Eye Visit Category | 1% w/w Phentolamine Mesylate Ophthalmic Solution (N = 31) n (%) | Placebo (N = 31) n (%) | 1% w/w Phentolamine Ophthalmic Mesylate Solution vs. Placebo [1] Odds Ratio (95% CI) | p-value |
|---|---|---|---|---|
| Tropicamide Both Eyes [2] 4 hours | | | | |
| n | 16 | 16 | | |
| <=0.5 mm above Baseline (−1 hour) | 13 (81.3) | 3 (18.8) | 40.33 (9.23, 176.16) | <0.0001 |

CI = Confidence interval. A reduction was determined using the change from baseline (−1 hour) in pupil diameter.

Percentages are the number of subjects with no more than 0.5 mm above Baseline (−1 hour), divided by the number of subjects with an assessment at the time point.

[1] From a generalized estimating equations model with a logit link, with reduction achievement (yes/no) as the dependent variable, treatment sequence, period, and treatment as fixed effects, subject within treatment sequence as a random effect, and baseline pupil diameter (−1 hour) as the covariate.
[2] The pooled data from the Study Eye and Non-study Eye.

TABLE 4A

Percent of Subjects With Unchanged Accommodation from Baseline by Time Point (Full Analysis Set)

| Eye<br>Visit<br>Category | 1% w/w Phentolamine<br>Mesylate Ophthalmic<br>Solution (N = 31)<br>n (%) | Placebo<br>(N = 31)<br>n (%) | 1% w/w Phentolamine<br>Mesylate Ophthalmic<br>Solution vs. Placebo [1]<br>Odds Ratio (95% CI) | p-value |
|---|---|---|---|---|
| Both Eyes [2] | | | | |
| 2 hours | | | | |
| n | 31 | 31 | | |
| Unchanged from Baseline (−1 hour) | 22 (71.0) | 21 (67.7) | 2.31 (1.13, 4.73) | 0.0223 |

Unchanged accommodation from Baseline (−1 hour) is defined as a change from baseline value >= −1, as measured in diopters.
CI = Confidence interval.
Percentages are the number of subjects with unchanged accommodation divided by the number of subjects with an assessment at the time point.
[1] From a generalized estimating equations model with a logit link, with unchanged accommodation (yes/no) as the dependent variable, treatment sequence, period, treatment, and mydriatic agent as fixed effects, subject within treatment sequence as a random effect, and baseline accommodation (−1 hour) as the covariate.
[2] The pooled data from the Study Eye and Non-study Eye.

TABLE 4B

Percent of Subjects With Unchanged Accommodation from Baseline by Time Point and Mydriatic Agent (Full Analysis Set)

| Mydratic Agent<br>Eye<br>Visit<br>Category | 1% w/w Phentolamine<br>Mesylate Ophthalmic<br>Solution (N = 31)<br>n (%) | Placebo<br>(N = 31)<br>n (%) | 1% w/w Phentolamine<br>Ophthalmic Mesylate<br>Solution vs. Placebo [1]<br>Odds Ratio (95% CI) | p-value |
|---|---|---|---|---|
| Tropicamide | | | | |
| Both Eyes [2] | | | | |
| 2 hours | | | | |
| n | 16 | 16 | | |
| Unchanged from Baseline (−1 hour) | 10 (62.5) | 6 (37.5) | 3.63 (1.39, 9.47) | 0.0084 |

Unchanged accommodation from Baseline (−1 hour) is defined as a change from baseline value >= −1, as measured in diopters.
CI = Confidence interval.
Percentages are the number of subjects with unchanged accommodation divided by the number of subjects with an assessment at the time point.
[1] From a generalized estimating equations model with a logit link, with unchanged accommodation (yes/no) as the dependent variable, treatment sequence, period, and treatment as fixed effects, subject within treatment sequence as a random effect, and baseline accommodation (−1 hour) as thecovariate.
[2] The pooled data from the Study Eye and Non-study Eye.

TABLE 5A

Conjunctival Hyperemia (Safety)

| Eye<br>Timepoint<br>Category | 1% w/w Phentolamine<br>Mesylate Ophthalmic<br>Solution (N = 31)<br>n (%) | Placebo<br>(N = 32)<br>n (%) | Total<br>(N = 32)<br>n (%) |
|---|---|---|---|
| Study Eye | | | |
| Baseline (−1 hour) | | | |
| n | 31 | 32 | 64 |
| None | 18 (58.1) | 21 (65.6) | 40 (62.5) |
| Mild | 12 (38.7) | 11 (34.4) | 23 (35.9) |
| Moderate | 1 (3.2) | 0 | 1 (1.6) |
| Severe | 0 | 0 | 0 |
| Numeric Scale [1] | | | |
| n | 31 | 32 | 64 |
| Mean (SD) | 0.5 (0.57) | 0.3 (0.48) | 0.4 (0.52) |
| Median | 0.0 | 0.0 | 0.0 |
| Min, Max | 0, 2 | 0, 1 | 0, 2 |
| 0 Minutes | | | |
| n | 31 | 32 | 63 |
| None | 25 (80.6) | 23 (71.9) | 48 (76.2) |
| Mild | 5 (16.1) | 9 (28.1) | 14 (22.2) |
| Moderate | 1 (3.2) | 0 | 1 (1.6) |
| Severe | 0 | 0 | 0 |

Percentages are the number of subjects in each category divided by the number of subjects with an examination at the Time Point.
[1] Conjunctival redness is graded on a 4-point scale: 0 = none; 1 = mild; 2 = moderate; 3 = severe

TABLE 5B

Conjunctival Hyperemia (Safety)

| Eye Timepoint Category | 1% w/w Phentolamine Mesylate Ophthalmic Solution (N = 31) n (%) | Placebo (N = 32) n (%) | Total (N = 32) n (%) |
|---|---|---|---|
| Study Eye Numeric Scale [1] | | | |
| n | 31 | 32 | 63 |
| Mean (SD) | 0.2 (0.50) | 0.3 (0.46) | 0.3 (0.47) |
| Median | 0.0 | 0.0 | 0.0 |
| Min, Max | 0, 2 | 0, 1 | 0, 2 |
| 30 Minutes | | | |
| n | 31 | 32 | 63 |
| None | 3 (9.7) | 19 (59.4) | 22 (34.9) |
| Mild | 9 (29.0) | 13 (40.6) | 22 (34.9) |
| Moderate | 19 (61.3) | 0 | 19 (30.2) |
| Severe | 0 | 0 | 0 |
| Numeric Scale [1] | | | |
| n | 31 | 32 | 63 |
| Mean (SD) | 1.5 (0.68) | 0.4 (0.50) | 1.0 (0.81) |
| Median | 2.0 | 0.0 | 1.0 |
| Min, Max | 0, 2 | 0, 1 | 0, 2 |

Percentages are the number of subjects in each category divided by the number of subjects with an examination at the Time Point.
[1] Conjunctival redness is graded on a 4-point scale: 0 = none; 1 = mild; 2 = moderate; 3 = severe

TABLE 5C

Conjunctival Hyperemia (Safety)

| Eye Timepoint Category | 1% w/w Phentolamine Mesylate Ophthalmic Solution (N = 31) n (%) | Placebo (N = 32) n (%) | Total (N = 32) n (%) |
|---|---|---|---|
| Study Eye 1 Hour | | | |
| n | 31 | 32 | 63 |
| None | 2 (6.5) | 19 (59.4) | 21 (33.3) |
| Mild | 11 (35.5) | 12 (37.5) | 23 (36.5) |
| Moderate | 17 (54.8) | 1 (3.1) | 18 (28.6) |
| Severe | 1 (3.2) | 0 | 1 (1.6) |
| Numeric Scale [1] | | | |
| n | 31 | 32 | 63 |
| Mean (SD) | 1.5 (0.68) | 0.4 (0.56) | 1.0 (0.83) |
| Median | 2.0 | 0.0 | 1.0 |
| Min, Max | 0, 3 | 0, 2 | 0, 3 |
| 2 Hour | | | |
| n | 31 | 32 | 63 |
| None | 2 (6.5) | 19 (59.4) | 21 (33.3) |
| Mild | 14 (45.2) | 12 (37.5) | 26 (41.3) |
| Moderate | 15 (48.4) | 1 (3.1) | 16 (25.4) |
| Severe | 0 | 0 | 0 |

Percentages are the number of subjects in each category divided by the number of subjects with an examination at the Time Point.
[1] Conjunctival redness is graded on a 4-point scale: 0 = none; 1 = mild; 2 = moderate; 3 = severe

TABLE 5D

Conjunctival Hyperemia (Safety)

| Eye Timepoint Category | 1% w/w Phentolamine Mesylate Ophthalmic Solution (N = 31) n (%) | Placebo (N = 32) n (%) | Total (N = 32) n (%) |
|---|---|---|---|
| Study Eye Numeric Scale [1] | | | |
| n | 31 | 32 | 63 |
| Mean (SD) | 1.4 (0.62) | 0.4 (0.56) | 0.9 (0.77) |
| Median | 1.0 | 0.0 | 1.0 |
| Min, Max | 0, 2 | 0, 2 | 0, 2 |
| 4 Hour | | | |
| n | 31 | 32 | 63 |
| None | 3 (9.7) | 20 (62.5) | 23 (36.5) |
| Mild | 22 (71.0) | 11 (34.4) | 33 (52.4) |
| Moderate | 6 (19.4) | 1 (3.1) | 7 (11.1) |
| Severe | 0 | 0 | 0 |
| Numeric Scale [1] | | | |
| n | 31 | 32 | 63 |
| Mean (SD) | 1.1 (0.54) | 0.4 (0.56) | 0.7 (0.65) |
| Median | 1.0 | 0.0 | 1.0 |
| Min, Max | 0, 2 | 0, 2 | 0, 2 |

Percentages are the number of subjects in each category divided by the number of subjects with an examination at the Time Point.
[1] Conjunctival redness is graded on a 4-point scale: 0 = none; 1 = mild; 2 = moderate; 3 = severe

TABLE 5E

Conjunctival Hyperemia (Safety)

| Eye Timepoint Category | 1% w/w Phentolamine Mesylate Ophthalmic Solution (N = 31) n (%) | Placebo (N = 32) n (%) | Total (N = 32) n (%) |
|---|---|---|---|
| Study Eye 6 Hour | | | |
| n | 31 | 32 | 63 |
| None | 10 (32.3) | 21 (65.6) | 31 (49.2) |
| Mild | 17 (54.8) | 11 (34.4) | 28 (44.4) |
| Moderate | 4 (12.9) | 0 | 4 (6.3) |
| Severe | 0 | 0 | 0 |
| Numeric Scale [1] | | | |
| n | 31 | 32 | 63 |
| Mean (SD) | 0.8 (0.65) | 0.3 (0.48) | 0.6 (0.61) |
| Median | 1.0 | 0.0 | 1.0 |
| Min, Max | 0, 2 | 0, 1 | 0, 2 |

Percentages are the number of subjects in each category divided by the number of subjects with an examination at the Time Point.
[1] Conjunctival redness is graded on a 4-point scale: 0 = none; 1 = mild; 2 = moderate; 3 = severe Observed experimental results from the IOP measurements are provided in Tables 6 and 7 below.

TABLE 6

| Patient Characteristics* | | 1% w/w Phentolamine Mesylate Ophthalmic Solution | | | |
|---|---|---|---|---|---|
| IOP Baseline (mmHg)** | Average Baseline Diurnal IOP (mmHg) | n (number of eyes) | Average Change in IOP from Baseline (mmHg) | Min | Max |
| <22 | 15.2 | 62 | −1.35 | −10 | 3 |
| <20 | 15.1 | 60 | −1.28 | −10 | 3 |

TABLE 6-continued

| | 1% w/w Phentolamine Mesylate Ophthalmic Solution | | | | |
|---|---|---|---|---|---|
| Patient Characteristics* | | | Average Change in IOP | | |
| IOP Baseline (mmHg)** | Average Baseline Diurnal IOP (mmHg) | n (number of eyes) | from Baseline (mmHg) | Min | Max |
| <19 | 14.8 | 55 | −1.09 | −7 | 3 |
| <18 | 14.2 | 48 | −1.06 | −7 | 3 |
| <17 | 13.5 | 38 | −1.00 | −6 | 2 |
| <16 | 13   | 32 | −0.75 | −4 | 2 |
| <15 | 12.3 | 24 | −1.13 | −4 | 2 |
| <14 | 11.5 | 16 | −1.44 | −4 | 2 |
| <13 | 11.2 | 13 | −1.54 | −4 | 2 |
| <12 | 10.8 | 9  | −1.67 | −4 | 2 |

*Per protocol.
**As measured at Week 1 Baseline; changes measured at 6-8 hours post dose.

TABLE 7

| | Placebo | | | | | |
|---|---|---|---|---|---|---|
| Patient Characteristics* | | | Average | | | |
| IOP Baseline (mmHg)** | Average Baseline Diurnal IOP (mmHg) | n (number of eyes) | Change in IOP Baseline (mmHg) | Min | Max | p value |
| <22 | 15.2 | 62 | −0.65 | −6 | 3 | 0.0803 |
| <20 | 15.1 | 60 | −0.50 | −5 | 3 | 0.047 |
| <19 | 14.8 | 55 | −0.40 | −5 | 3 | 0.0767 |
| <18 | 14.2 | 48 | −0.25 | −5 | 3 | 0.0471 |
| <17 | 13.5 | 38 | −0.18 | −5 | 3 | 0.0734 |
| <16 | 13   | 32 | 0.00  | −5 | 3 | 0.1276 |
| <15 | 12.3 | 24 | −0.13 | −5 | 3 | 0.1078 |
| <14 | 11.5 | 16 | 0.06  | −4 | 3 | 0.0446 |
| <13 | 11.2 | 13 | 0.38  | −4 | 3 | 0.0094 |
| <12 | 10.8 | 9  | 0.56  | −1 | 3 | 0.0119 |

*Per protocol.
**As measured at Week 1 Baseline; changes measured at 6-8 hours post dose.

Example 4-Improvement in Near Vision Acuity Using Phentolamine Mesylate in Human Subjects with Open-Angle Glaucoma or Ocular Hypertension Ability of phentolamine mesylate to improve near vision acuity in human subjects with bilateral open-angle glaucoma (OAG) or ocular hypertension (OHT) was evaluated according to a clinical study in which an aqueous ophthalmic solution containing phentolamine mesylate was administered to the eye of a patient, and then the patient was evaluated for improvement in near vision acuity in the eye that received the aqueous ophthalmic solution containing phentolamine mesylate. Approximately 40 subjects with either OAG or OHT were randomized, for a target of 36 completed subjects. Subjects were randomized in a 1:1 ratio to receive 1% w/w Phentolamine Mesylate Ophthalmic Solution or placebo once daily for 14 days beginning at 8 PM to 10 PM on Day 1 and continuing through Day 14. Evaluations of near vision acuity took place at the Baseline and the Treatment-study Visit days (Day 8±1 Day and Day 15±1 Day) at 8 AM, 10 AM, and 4 PM. There were Follow-up Visits on Day 16 at 8 AM±15 minutes and by phone on Day 22 (7 days after the last Treatment-study Visit). Further experimental procedures and results are described below.

Part I—Experimental Procedures

The total length of subject participation was approximately 7 to 8 weeks with six clinic visits and one telephone call follow up, as summarized below:
  Screening Visit (1 day).
  Washout Visit/period (as necessary) (4-5 weeks with safety check visit at 2 weeks).
  Qualification/Baseline Visit (1 day).
  Treatment-study Visit Day 8 (1 week).
  Treatment-study Visit Day 15 (1 week).
  Follow-up clinic Visit on Day 16 (1 day).
  Follow-up telephone call at Day 22 (1 week).

Human subjects were screened for potential enrollment and, if qualified, enrolled in the study. Inclusion criteria and exclusion criteria for the study are set forth below. Human subjects could qualify in either eye.

Inclusion Criteria
  18 years of age or greater.
  Diagnosis of OAG or OHT. The diagnosis of OHT must have been in both eyes. For OAG, the diagnosis could have been in either eye with OHT in the fellow eye. A reported history of untreated OHT with IOP≥22 mmHg and ≤30 mmHg was preferred.
  Untreated or treated OAG/OHT with 2 or fewer ocular hypotensive medications.
  Untreated (post-washout) mean IOP≥22 mmHg and ≤30 mmHg in the study eye at the Qualification Visit (8 AM).
  Corrected visual acuity in each eye+1.0 log MAR or better by Early Treatment Diabetic Retinopathy Study (ETDRS) in each eye (equivalent to 20/200 or better) at the Screening Visit and Qualification Visit.
  Otherwise healthy and well-controlled subjects.
  Able and willing to give signed informed consent and follow study instructions.
  Able to self-administer study medication or to have study medication administered by a caregiver throughout the study period.

Exclusion Criteria
  Closed or very narrow angles (Grade 0-1, Shaffer) or angles that the investigator judges as occludable and/or with evidence of peripheral anterior synechiae (PAS)≥180 degrees by gonioscopy within 6 months prior to Screening Visit in either eye.
  Glaucoma: pseudo-exfoliation or pigment dispersion component, history of angle closure or narrow angles. Note: Previous laser peripheral iridotomy was not allowed.
  Known hypersensitivity to any α-adrenoceptor antagonists.
  Previous laser and/or non-laser glaucoma surgery or procedure in either eye.
  Refractive surgery in either eye (e.g., radial keratotomy, photorefractive keratectomy (PRK), laser-assisted in situ keratomileusis (LASIK), or corneal cross linking).
  Ocular trauma in either eye within the 6 months prior to Screening, or ocular surgery or non-refractive laser treatment within the 3 months prior to Screening.

Recent or current evidence of ocular infection or inflammation in either eye. Current evidence of clinically significant blepharitis, conjunctivitis, or a history of herpes simplex or herpes zoster keratitis at Screening in either eye.

Ocular medication in either eye of any kind within 30 days of Screening, with the exception of a) ocular hypotensive medications (which had to be washed out), b) lid scrubs (which could be used prior to Screening but could not be used after Screening) or c) lubricating drops for dry eye (preservative-free artificial tears), which could be used throughout the study.

Clinically significant ocular disease in either eye as deemed by the investigator (e.g., corneal edema, uveitis, or severe keratoconjunctivitis sicca) that might interfere with the study, including glaucomatous damage so severe that washout of ocular hypotensive medications for 1 month was not judged safe (i.e., cup-to-disc ratio >0.8, severe visual field defect).

History of diabetic retinopathy.

Contact lens wear within 3 days prior to and for the duration of the study.

Central corneal thickness in either eye >600 μm at Screening.

Any abnormality in either eye preventing reliable applanation tonometry (e.g., central corneal scarring).

Known hypersensitivity or contraindication to α- and/or β-adrenoceptor antagonists (e.g., chronic obstructive pulmonary disease or bronchial asthma; abnormally low blood pressure or heart rate; second or third degree heart block or congestive heart failure; or severe diabetes).

Clinically significant systemic disease (e.g., uncontrolled diabetes, myasthenia gravis, cancer, hepatic, renal, endocrine or cardiovascular disorders) that might interfere with the study.

Participation in any investigational study within 30 days prior to Screening.

Use of any topical or systemic adrenergic or cholinergic drugs up to 30 days prior to Screening, or during the study unless the drug, dose and regimen had been consistent for the 30 days prior to Screening.

Changes in systemic medication that could have an effect on IOP within 30 days prior to Screening or anticipated during the study.

Women of childbearing potential who were pregnant, nursing, planning a pregnancy, or not using a medically acceptable form of birth control. An adult woman was considered to be of childbearing potential unless she was 1 year postmenopausal or 3 months post-surgical sterilization. All females of childbearing potential must have had a negative urine pregnancy test result at the Screening and Qualification examinations and must have intended to not become pregnant during the study.

Resting heart rate (HR) outside the normal range (50-110 beats per minute) at the Screening or Qualification Visit. HR could be repeated only once if outside the normal range, following at least a 5 minute rest period in the sitting position.

Hypertension with resting diastolic blood pressure (BP)>105 mmHg or systolic BP>160 mmHg at the Screening or Qualification Visit. BP could be repeated only once if outside the specified range, following at least a 5 minute rest period in the sitting position.

Subjects with an ophthalmic history of increased IOP (≥22 mmHg and ≤30 mmHg) were selected for study participation and were screened for study eligibility.

After Screening, eligible subjects, if being treated at the time with glaucoma medications, were required to washout and refrain from administration of any glaucoma drugs for at least 28 days and no more than 35 days prior to the Qualification Visit. The washout subjects were brought back at approximately two weeks after starting the washout period for an IOP safety check. In the judgement of the investigator, if there was any risk to the eye(s) of the subject, or if the mean IOP in either eye during washout was >30 mmHg, then an appropriate rescue or prior medication was administered, and the subject was considered a screen failure. Adverse events occurring during the washout period were also assessed at this visit. After the washout, where applicable, a Qualification Visit occurred before dosing on Day 1.

Subjects not previously treated with any glaucoma drugs did not require a washout period and could return the following day, or up to 35 days later, for their Qualification/Baseline Visit.

At the Qualification/Baseline Visit:

Females of childbearing potential took a urine pregnancy test at 8 AM.

Review of concomitant medications was conducted at 8 AM.

Pupil diameter, using a Neuroptics pupillometer, near visual acuity using a standard chart held at 14 inches, and distance visual acuity with ETDRS were measured at 8 AM.

Eye redness (conjunctival hyperemia) was visually checked at 8 AM, 10 AM and 4 PM using the CCLRU bulbar redness scale.

Adverse events were reviewed at each timepoint.

The first dose of study medication was taken at 8 PM to 10 PM on the Baseline Visit (Day 1). Site personnel demonstrated the proper installation technique to the subject at the Qualification/Baseline Visit (Day 1) and the subject self-administered a dose of artificial tears at the study site, instilling 1 drop in each eye from the unit-dose bottle (Note: If a drop was not instilled into the eye, the subject was instructed to wait approximately 10-15 seconds and administer a second drop). The subject received the following instructions regarding proper instillation technique:

The subject should be in a seated position and should tilt his or her head backward for administration of the study medication. The bottle of study medication should be held at an almost vertical position above the eye while the lower eyelid is pulled down gently, and 1 drop is placed into the conjunctival cul-de-sac. The tip of the bottle should not touch the eye. After a drop is instilled in each eye, the subject should keep the eyes gently closed for approximately 30 seconds. After successful instillation of the drop in each eye, the subject should carefully empty any remaining contents as directed.

The subject was given their study medication dropper bottles, instructions when to administer the eye drop (8 PM to 10 PM), and when to return to the clinic.

The subject was instructed to administer one drop to each eye from a new single unit-dose bottle, each evening of dosing, and close the eyes gently for 30 seconds, then empty the remaining bottle contents (and store the opened bottle in the baggie provided and place it in the medication box for return to the study site at the Day 8 Visit). The subject was instructed to follow the same procedures each subsequent evening of dosing (approximately 24 hours between doses). At the Day 8 visit, the medication box, complete with opened bottles and any unopened study medication was to be returned to the study site where the baggies of opened medication were removed, and the study medication box was re-dispensed with the unopened medication. During the second week of treatment, subjects were instructed to continue to administer one drop of study medication to each eye every night using a new bottle for each dose, then emptying the remaining contents of that bottle (and storing the opened bottles in the baggies and placing them back in the box to return to the study site at the Day 15 Visit). The Day 15 visit was the last day of study treatment; no further study medication was dispensed at that visit.

The subject was instructed to contact the investigator should adverse events of concern occur (e.g., shortness of breath, fainting, etc.), or to go to the emergency room if the event was life-threatening.

Treatment-study visits occurred twice—on Day 8±1 Day and Day 15±1 Day. On Study Day 8, the following was performed:

Review of concomitant medications was conducted at 8 AM.

Near and distance visual acuity were measured.

Eye redness (conjunctival hyperemia) was visually checked using the CCLRU bulbar redness scale.

On Study Day 15, the following was performed:

Subjects were to bring their used dropper bottles and any unused medications with them for purposes of drug accountability.

Subjects were asked if they had any problems with their eyes from the last visit, and if there have been any changes in their medical condition, or concomitant medications, since their last visit. Any changes in the condition of the subject were recorded as an adverse event.

Near and distance visual acuity distance visual acuity was measured.

Eye redness (conjunctival hyperemia) was visually checked at each time point using the CCLRU bulbar redness scale.

Adverse events were reviewed at each time point.

Distance and near visual acuity, pupil diameter, and a complete ophthalmic examination, including biomicroscopy were also performed at 4 PM.

Subjects completing their Day 15 Visit were instructed not to resume their original glaucoma medication(s) until after completion of the Day 22 Follow-up phone call.

A Follow-up Visit occurred at 8 AM±15 minutes on Day 16. Assessments performed at this visit included an IOP measurement at 8 AM±15 minutes, visual acuity, pupil diameter, and safety measures. More specifically, the following were performed:

Subjects were asked if they had any problems with their eyes from the last visit, and if there have been any changes in their medical condition, or concomitant medications, since their last visit. Any changes in the condition of the subject were recorded as an adverse event.

Review of concomitant medications was conducted at 8 AM.

IOP was measured twice in the study eye at 8 AM±15 minutes, and the two values were averaged. If the difference in the two IOP measurements was >5 mmHg, a third measurement was obtained, and the three values were averaged.

Pupil diameter, near and distance visual acuity distance visual acuity, resting HR and BP were measured at 8 AM. Blood pressure, using the same arm, same cuff size appropriate for arm circumference throughout the study, and heart rate were measured after at least 3 minutes rest in the sitting position. If HR or BP were outside the normal range (HR<50 or >110 beats per minute, resting diastolic blood pressure (BP)>105 mmHg or systolic BP>160 mmHg), they could be repeated only once following at least a 5 minute rest period in the sitting position.

Eye redness (conjunctival hyperemia) was visually checked at each timepoint using the CCLRU bulbar redness scale.

Adverse events were reviewed at 8 AM.

Subjects completing their Day 16 Visit were reminded not to resume their original glaucoma medication(s) until after completion of the Day 22 Follow-up phone call.

A Follow-up Visit phone call occurred on Day 22, seven days after the last dose. Any concomitant medications, subject-reported conjunctiva redness and adverse events (AEs) were collected.

Visits on Day 8 and 15 were allowed to be 1 day early or late. If the visit was late, the subject was advised to take an additional dose from one of the 2 spare dropper bottles provided in the study medication box the night before the visit. The subject was instructed to then empty the remaining contents and store the opened bottle in the baggie provided and place it in the medication box for return to the study site at their next visit. If the Day 15 Visit occurred one day early or late, the Day 16 Visit and the Day 22 telephone call were adjusted accordingly.

Any subject was permitted to voluntarily withdraw from the study at any time without prejudice. A non-completing subject was defined as one who exited the study by their own volition or at the discretion of the Investigator and/or the Medical Monitor prior to completing all of the study procedures required in the protocol.

Study subjects received study medication as set forth in Table 1 according to the Treatment Group to which the subject was assigned. Study medication is listed in Table 2.

TABLE 1

| Treatment Groups | |
| --- | --- |
| Treatment Group | Study Medication and Administration Protocol |
| 1 | One drop of 1% w/w Phentolamine Mesylate Ophthalmic Solution in each eye daily at 8 PM to 10 PM for 14 days, from Day 1 through Day 14 for subjects randomized to active treatment. |
| 2 | One drop of Placebo Ophthalmic Solution in each eye daily at 8 PM to 10 PM for 14 days, from Day 1 through Day 14 for subjects randomized to placebo. |

TABLE 2

| Study Medication | |
| --- | --- |
| Study Medication | Composition of Study Medication |
| 1% w/w Phentolamine Mesylate Ophthalmic Solution | 1% w/w phentolamine mesylate<br>4% w/w mannitol<br>3 mM buffer comprising sodium acetate and acetic acid<br>water<br>pH in the range 4.8 to 5.0 |
| Placebo Ophthalmic Solution | 4% w/w mannitol<br>3 mM buffer comprising sodium acetate and acetic acid<br>water<br>pH in the range 4.8 to 5.0 |

Part II—Results

Baseline visual acuity data collected on subjects prior to administration of phentolamine mesylate at the beginning of the study is provide in Tables 1-4. Observed improvement in near vision acuity data is provided in Tables 5 and 6. Results of observations for conjunctival hyperemia is reported in Tables 7 and 8. The data in Tables 7 and 8 show that there was no statistically significant difference in observed conjunctival hyperemia between patients that received placebo and patients that received 1% w/w Phentolamine Mesylate Ophthalmic Solution. Observed changes in pupil diameter are provided in Tables 9A, 9B, 10A, 10B, 11A, and 11R.

TABLE 1

| Baseline Characteristics (Distance-corrected Near Vision Acuity) | | | |
| --- | --- | --- | --- |
| Demographics and Baseline Characteristics | 1% w/w Phentolamine Mesylate Ophthalmic Solution (N = 19) | Placebo (N = 20) | Total (N = 39) |
| Baseline DCNVA, photopic (OD) | | | |
| n | 19 | 20 | 39 |
| Mean (SD) | 0.29 (0.253) | 0.25 (0.196) | 0.27 (0.224) |
| Median | 0.20 | 0.25 | 0.20 |
| Min, Max | −0.1, 0.8 | 0, 0.6 | −0.1, 0.8 |

Note:
Min = Minimum,
Max = Maximum,
SD = Standard deviation,
OD = Right eye;
OS = Left eye,
BCDVA = Best corrected distance visual acuity,
DCNVA = Distance corrected near visual acuity.
Percentages are the number of subjects in the category divided by the number of subjects randomized in the group.
[1] Subjects are categorized as <25 mmHg if their study eye Baseline IOP readings at all timepoints (8 AM, 10 AM, and 4 PM) are <25 mmHg.
[2] The pooled data from the Study Eye and Fellow Eye.

TABLE 2

| Demographics and Baseline Characteristics | 1% w/w Phentolamine Mesylate Ophthalmic Solution (N = 19) | Placebo (N = 20) | Total (N = 39) |
| --- | --- | --- | --- |
| Baseline DCNVA, photopic (OS) | | | |
| n | 19 | 20 | 39 |
| Mean (SD) | 0.29 (0.271) | 0.21 (0.168) | 0.25 (0.225) |
| Median | 0.20 | 0.20 | 0.20 |
| Min, Max | −0.2, 0.8 | 0, 0.6 | −0.2, 0.8 |
| Baseline DCNVA, photopic (Study Eye) | | | |
| n | 19 | 20 | 39 |
| Mean (SD) | 0.28 (0.257) | 0.22 (0.179) | 0.25 (0.220) |
| Median | 0.20 | 0.20 | 0.20 |
| Min, Max | −0.1, 0.7 | 0, 0.6 | −0.1, 0.7 |

TABLE 2-continued

| Demographics and Baseline Characteristics | 1% w/w Phentolamine Mesylate Ophthalmic Solution (N = 19) | Placebo (N = 20) | Total (N = 39) |
|---|---|---|---|
| Baseline DCNVA, photopic (Fellow Eye) | | | |
| n | 19 | 20 | 39 |
| Mean (SD) | 0.30 (0.267) | 0.24 (0.187) | 0.27 (0.229) |
| Median | 0.30 | 0.20 | 0.20 |
| Min, Max | −0.2, 0.8 | 0, 0.6 | −0.2, 0.8 |

Note:
Min = Minimum,
Max = Maximum,
SD = Standard deviation,
OD = Right eye;
OS = Left eye,
BCDVA = Best corrected distance visual acuity,
DCNVA = Distance corrected near visual acuity. Percentages are the number of subjects in the category divided by the number of subjects randomized in the group.
[1] Subjects are categorized as <25 mmHg if their study eye Baseline IOP readings at all timepoints (8 AM, 10 AM, and 4 PM) are <25 mmHg.
[2] The pooled data from the Study Eye and Fellow Eye.

TABLE 3

| Demographics and Baseline Characteristics | 1% w/w Phentolamine Mesylate Ophthalmic Solution (N = 19) | Placebo (N = 20) | Total (N = 39) |
|---|---|---|---|
| Baseline DCNVA, photopic (All Eyes [2]) | | | |
| n | 38 | 40 | 78 |
| Mean (SD) | 0.29 (0.258) | 0.23 (0.181) | 0.26 (0.223) |
| Median | 0.20 | 0.20 | 0.20 |
| Min, Max | −0.2, 0.8 | 0, 0.6 | −0.2, 0.8 |
| Baseline DCNVA, mesopic (OD) | | | |
| n | 19 | 20 | 39 |
| Mean (SD) | 0.37 (0.279) | 0.39 (0.211) | 0.38 (0.243) |
| Median | 0.40 | 0.40 | 0.40 |
| Min, Max | −0.1, 0.9 | 0, 0.8 | −0.1, 0.9 |
| Baseline DCNVA, mesopic (OS) | | | |
| n | 19 | 20 | 39 |
| Mean (SD) | 0.38 (0.289) | 0.34 (0.211) | 0.36 (0.250) |
| Median | 0.30 | 0.35 | 0.30 |
| Min, Max | 0, 0.9 | 0, 0.8 | 0, 0.9 |

Note:
Min = Minimum,
Max = Maximum,
SD = Standard deviation,
OD = Right eye;
OS = Left eye,
BCDVA = Best corrected distance visual acuity,
DCNVA = Distance corrected near visual acuity.

Percentages are the number of subjects in the category divided by the number of subjects randomized in the group.
[1] Subjects are categorized as <25 mmHg if their study eye Baseline IOP readings at all timepoints (8 AM, 10 AM, and 4 PM) are <25 mmHg.
[2] The pooled data from the Study Eye and Fellow Eye.

TABLE 4

| Demographics and Baseline Characteristics | 1% w/w Phentolamine Mesylate Ophthalmic Solution (N = 19) | Placebo (N = 20) | Total (N = 39) |
|---|---|---|---|
| Baseline DCNVA, mesopic (Study Eye) | | | |
| n | 19 | 20 | 39 |
| Mean (SD) | 0.38 (0.286) | 0.36 (0.211) | 0.37 (0.247) |
| Median | 0.30 | 0.40 | 0.40 |
| Min, Max | 0, 0.9 | 0, 0.8 | 0, 0.9 |
| Baseline DCNVA, mesopic (Fellow Eye) | | | |
| n | 19 | 20 | 39 |
| Mean (SD) | 0.38 (0.282) | 0.37 (0.213) | 0.37 (0.246) |
| Median | 0.40 | 0.40 | 0.40 |
| Min, Max | −0.1, 0.9 | 0, 0.8 | −0.1, 0.9 |
| Baseline DCNVA, mesopic (All Eyes [2]) | | | |
| n | 38 | 40 | 78 |
| Mean (SD) | 0.38 (0.280) | 0.36 (0.210) | 0.37 (0.245) |
| Median | 0.35 | 0.40 | 0.40 |
| Min, Max | −0.1, 0.9 | 0, 0.8 | −0.1, 0.9 |

Note:
Min = Minimum,
Max = Maximum,
SD = Standard deviation,
OD = Right eye;
OS = Left eye,
BCDVA = Best corrected distance visual acuity,
DCNVA = Distance corrected near visual acuity.
Percentages are the number of subjects in the category divided by the number of subjects randomized in the group.
[1] Subjects are categorized as <25 mmHg if their study eye Baseline IOP readings at all timepoints (8 AM, 10 AM, and 4 PM) are <25 mmHg.
[2] The pooled data from the Study Eye and Fellow Eye.

TABLE 5

Observed Change in Near Vision Acuity

| Eye Light Condition Visit Category [1] | 1% w/w Phentolamine Mesylate Ophthalmic Solution (N = 19) n (%) | Placebo (N = 20) n (%) | 1% w/w Phentolamine Mesylate Ophthalmic Solution vs. Placebo [2] Odds Ratio (95% CI) | p-value |
|---|---|---|---|---|
| All Eyes [3] Photopic Day 8, 8 AM | | | | |
| n | 19 | 20 | | |
| >=1 line | 12 (63.2) | 5 (25.0) | 6.17 (1.81, 24.91) | 0.0018 |
| >=2 lines | 4 (21.1) | 3 (15.0) | 2.03 (0.37, 14.10) | 0.5678 |
| >=3 lines | 2 (10.5) | 1 (5.0) | 1.44 (0.05, 112.24) | 1.0000 |
| Day 15, 8 AM | | | | |
| n | 19 | 20 | | |
| >=1 line | 13 (68.4) | 8 (40.0) | 4.13 (1.41, 12.88) | 0.0072 |
| >=2 lines | 4 (21.1) | 1 (5.0) | 4.73 (0.44, 245.09) | 0.3054 |
| >=3 lines | 2 (10.5) | 0 | 0.76 (0.04, >999.99) | 1.0000 |
| Day 16, 8 AM | | | | |
| n | 19 | 20 | | |
| >=1 line | 14 (73.7) | 9 (45.0) | 3.72 (1.24, 11.91) | 0.0163 |
| >=2 lines | 8 (42.1) | 2 (10.0) | 6.92 (1.23, 73.03) | 0.0232 |
| >=3 lines | 4 (21.1) | 1 (5.0) | 2.51 (0.15, 150.96) | 0.8354 |

CI = Confidence interval.
Percentages are the number of subjects achieving the improvement divided by the number of subjects with an assessment at the timepoint.
[1] 1 line = 1.3 LogMAR; 2 lines = 1.2 LogMAR; 3 lines = 1.1 LogMAR, etc.
[2] From the logistic regression with treatment as a factor; and Baseline DCNVA as the covariate.
[3] The pooled data from the Study Eye and Fellow Eye. Subjects are counted in a category if they meet the reduction criterion for at least one eye.

TABLE 6

Observed Change in Near Vision Acuity

| Eye Light Condition Visit Category [1] | 1% w/w Phentolamine Mesylate Ophthalmic Solution (N = 19) n (%) | Placebo (N = 20) n (%) | 1% w/w Phentolamine Mesylate Ophthalmic Solution vs. Placebo [2] Odds Ratio (95% CI) | p-value |
|---|---|---|---|---|
| All Eyes [3] Mesopic Day 8, 8 AM | | | | |
| n | 19 | 20 | | |
| >=1 line | 9 (47.4) | 7 (35.0) | 1.71 (0.58, 5.14) | 0.3967 |
| >=2 lines | 3 (15.8) | 1 (5.0) | 2.92 (0.20, 165.98) | 0.6911 |
| >=3 lines | 0 | 0 | | |
| Day 15, 8 AM | | | | |
| n | 19 | 20 | | |
| >=1 line | 13 (68.4) | 7 (35.0) | 4.21 (1.43, 13.34) | 0.0064 |
| >=2 lines | 5 (26.3) | 4 (20.0) | 1.57 (0.38, 6.92) | 0.6820 |
| >=3 lines | 0 | 0 | | |
| Day 16, 8 AM | | | | |
| n | 19 | 20 | | |
| >=1 line | 12 (63.2) | 9 (45.0) | 2.60 (0.92, 7.73) | 0.0752 |
| >=2 lines | 8 (42.1) | 2 (10.0) | 4.11 (0.89, 26.28) | 0.0750 |
| >=3 lines | 3 (15.8) | 0 | 4.92 (0.77, >999.99) | 0.1627 |

CI = Confidence interval.
Percentages are the number of subjects achieving the improvement divided by the number of subjects with an assessment at the timepoint.
[1] 1 line = 1.3 LogMAR; 2 lines = 1.2 LogMAR; 3 lines = 1.1 LogMAR, etc.
[2] From the logistic regression with treatment as a factor; and Baseline DCNVA as the covariate.
[3] The pooled data from the Study Eye and Fellow Eye. Subjects are counted in a category if they meet the reduction criterion for at least one eye.

TABLE 7

Conjunctival Hyperemia Data for the Study Eye

| | 1% w/w Phentolamine Mesylate Ophthalmic Solution (N = 19) | Placebo (N = 20) | p-value from Fisher's exact test |
|---|---|---|---|
| Day 8, 8 am n (%) | | | 0.3899 |
| None | 4 (21.1) | 7 (35.0) | |
| Mild | 11 (57.9) | 9 (45.0) | |
| Moderate | 2 (10.5) | 4 (20.0) | |
| Severe | 2 (10.5) | 0 (0.0) | |
| Day 8, 10 am n (%) | | | 0.2651 |
| None | 4 (21.1) | 6 (30.0) | |
| Mild | 12 (63.2) | 10 (50.0) | |
| Moderate | 1 (5.3) | 4 (20.0) | |
| Severe | 2 (10.5) | 0 (0.0) | |
| Day 8, 4 pm n (%) | | | 0.2651 |
| None | 4 (21.1) | 6 (30.0) | |
| Mild | 12 (63.2) | 10 (50.0) | |
| Moderate | 1 (5.3) | 4 (20.0) | |
| Severe | 2 (10.5) | 0 (0.0) | |
| Day 15, 8 am n (%) | | | 0.3476 |
| None | 4 (21.1) | 8 (40.0) | |
| Mild | 10 (52.6) | 8 (40.0) | |
| Moderate | 3 (15.8) | 4 (20.0) | |
| Severe | 2 (10.5) | 0 (0.0) | |
| Day 15, 10 am n (%) | | | 0.3995 |
| None | 5 (26.3) | 8 (40.0) | |
| Mild | 10 (52.6) | 8 (40.0) | |
| Moderate | 2 (10.5) | 4 (20.0) | |
| Severe | 2 (10.5) | 0 (0.0) | |
| Day 15, 4 pm n (%) | | | 1.0000 |
| None | 7 (36.8) | 8 (40.0) | |
| Mild | 9 (47.4) | 9 (45.0) | |
| Moderate | 3 (15.8) | 3 (15.0) | |
| Severe | 0 (0.0) | 0 (0.0) | |
| Day 16, 8 am n (%) | | | 1.0000 |
| None | 9 (47.4) | 8 (40.0) | |
| Mild | 8 (42.1) | 9 (45.0) | |
| Moderate | 1 (5.3) | 2 (10.0) | |
| Severe | 1 (5.3) | 1 (5.0) | |

TABLE 8

Conjunctival Hyperemia Data for the Fellow Eye

| | 1% w/w Phentolamine Mesylate Ophthalmic Solution (N = 19) | Placebo (N = 20) | p-value from Fisher's exact test |
|---|---|---|---|
| Day 8, 8 am n (%) | | | 0.2401 |
| None | 4 (21.1) | 7 (35.0) | |
| Mild | 11 (57.9) | 8 (40.0) | |
| Moderate | 2 (10.5) | 5 (25.0) | |
| Severe | 2 (10.5) | 0 (0.0) | |
| Day 8, 10 am n (%) | | | 0.1552 |
| None | 4 (21.1) | 6 (30.0) | |
| Mild | 12 (63.2) | 9 (45.0) | |
| Moderate | 1 (5.3) | 5 (25.0) | |
| Severe | 2 (10.5) | 0 (0.0) | |
| Day 8, 4 pm n (%) | | | 0.1552 |
| None | 4 (21.1) | 6 (30.0) | |
| Mild | 12 (63.2) | 9 (45.0) | |
| Moderate | 1 (5.3) | 5 (25.0) | |
| Severe | 2 (10.5) | 0 (0.0) | |
| Day 15, 8 am n (%) | | | 0.4029 |
| None | 6 (31.6) | 9 (45.0) | |
| Mild | 9 (47.4) | 7 (35.0) | |
| Moderate | 2 (10.5) | 4 (20.0) | |
| Severe | 2 (10.5) | 0 (0.0) | |
| Day 15, 10 am n (%) | | | 0.5049 |
| None | 6 (31.6) | 8 (40.0) | |
| Mild | 9 (47.4) | 8 (40.0) | |
| Moderate | 2 (10.5) | 4 (20.0) | |
| Severe | 2 (10.5) | 0 (0.0) | |
| Day 15, 4 pm n (%) | | | 1.0000 |
| None | 7 (36.8) | 8 (40.0) | |
| Mild | 9 (47.4) | 9 (45.0) | |
| Moderate | 3 (15.8) | 3 (15.0) | |
| Severe | 0 (0.0) | 0 (0.0) | |
| Day 16, 8 am n (%) | | | 0.7468 |
| None | 10 (52.6) | 8 (40.0) | |
| Mild | 7 (36.8) | 9 (45.0) | |
| Moderate | 2 (10.5) | 3 (15.0) | |
| Severe | 0 (0.0) | 0 (0.0) | |

TABLE 9A

Observed Change in Pupil Diameter Under Photopic Conditions

| Eye<br>Light Condition<br>Visit<br>Statistic | 1% w/w<br>Phentolamine<br>Mesylate<br>Ophthalmic Solution<br>(N = 19) | Placebo<br>(N = 20) | 1% w/w Phentolamine<br>Mesylate Ophthalmic<br>Solution vs. Placebo [1]<br>LS Mean Difference<br>(95% CI) | p-value |
|---|---|---|---|---|
| All Eyes [3]<br>Photopic<br>Day 15, 8 AM | | | | |
| n | 38 | 40 | | |
| Mean (SD) | 2.84 (0.485) | 3.54 (0.809) | | |
| Median | 2.77 | 3.45 | | |
| Min, Max | 2.2, 4.4 | 2.5, 6.0 | | |
| Day 15, 8 AM Change<br>from Baseline | | | | |
| n | 38 | 40 | | |
| Mean (SD) | −0.72 (0.578) | −0.08 (0.544) | | |
| Median | −0.64 | −0.12 | | |
| Min, Max | −2.0, 0.5 | −1.2, 1.4 | | |
| Day 15, 8 AM Change from<br>Baseline ANCOVA [1] | | | −0.66 (−0.87, −0.45) | <0.0001 |
| Least-squares mean (SE) | −0.73 (0.076) | −0.07 (0.074) | | |
| p-value [2] | <0.0001 | 0.3515 | | |

Min = Minimum,
Max = Maximum,
SD = Standard deviation,
LS = Least-squares,
CI = Confidence interval,
SE = Standard error

[1] From an analysis of covariance (ANCOVA) with (percent) change from Baseline in Pupil Diameter as the dependent variable, treatment as a factor; and Baseline Pupil Diameter as the covariate.
[2] From a test comparing the individual treatment change from baseline LS mean to zero.
[3] The pooled data from the Study Eye and Fellow Eye.

TABLE 9B

Observed Change in Pupil Diameter Under Photopic Conditions

| Eye<br>Light Condition<br>Visit<br>Statistic | 1% w/w<br>Phentolamine<br>Mesylate<br>Ophthalmic Solution<br>(N = 19) | Placebo<br>(N = 20) | 1% w/w Phentolamine<br>Mesylate Ophthalmic<br>Solution vs. Placebo [1]<br>LS Mean Difference<br>(95% CI) | p-value |
|---|---|---|---|---|
| All Eyes [3]<br>Photopic<br>Day 15, 8 AM Percent<br>Change from Baseline | | | | |
| n | 38 | 40 | | |
| Mean (SD) | −18.79 (13.168) | −0.56 (17.645) | | |
| Median | −19.55 | −3.93 | | |
| Min, Max | −40.4, 17.9 | −25.9, 70.1 | | |
| Day 15, 8 AM Percent<br>Change from Baseline<br>ANCOVA [1] | | | −18.90 (−25.20, −12.60) | <0.0001 |
| Least-squares mean (SE) | −19.13 (2.262) | −0.23 (2.205) | | |
| p-value [2] | <0.0001 | 0.9157 | | |
| Day 16, 8 AM | | | | |
| n | 38 | 40 | | |

TABLE 9B-continued

Observed Change in Pupil Diameter Under Photopic Conditions

| Eye<br>Light Condition<br>Visit<br>Statistic | 1% w/w<br>Phentolamine<br>Mesylate<br>Ophthalmic Solution<br>(N = 19) | Placebo<br>(N = 20) | 1% w/w Phentolamine<br>Mesylate Ophthalmic<br>Solution vs. Placebo [1]<br>LS Mean Difference<br>(95% CI) | p-value |
|---|---|---|---|---|
| Mean (SD) | 2.85 (0.497) | 3.70 (0.865) | | |
| Median | 2.84 | 3.49 | | |
| Min, Max | 2.0, 4.3 | 2.4, 6.5 | | |

Min = Minimum,
Max = Maximum,
SD = Standard deviation,
LS = Least-squares,
CI = Confidence interval,
SE = Standard error

[1] From an analysis of covariance (ANCOVA) with (percent) change from Baseline in Pupil Diameter as the dependent variable, treatment as a factor; and Baseline Pupil Diameter as the covariate.
[2] From a test comparing the individual treatment change from baseline LS mean to zero.
[3] The pooled data from the Study Eye and Fellow Eye.

TABLE 10A

Observed Change in Pupil Diameter Under Photopic Conditions

| Eye<br>Light Condition<br>Visit<br>Statistic | 1% w/w<br>Phentolamine<br>Mesylate<br>Ophthalmic Solution<br>(N = 19) | Placebo<br>(N = 20) | 1% w/w Phentolamine<br>Mesylate Ophthalmic<br>Solution vs. Placebo [1]<br>LS Mean Difference<br>(95% CI) | p-value |
|---|---|---|---|---|
| All Eyes [3]<br>Photopic<br>Day 16, 8 AM Change<br>from Baseline | | | | |
| n | 38 | 40 | | |
| Mean (SD) | −0.70 (0.532) | 0.08 (0.537) | | |
| Median | −0.55 | 0.01 | | |
| Min, Max | −1.9, 0.3 | −1.2, 1.4 | | |
| Day 16, 8 AM Change from<br>Baseline ANCOVA [1] | | | −0.80 (−1.01, −0.58) | <0.0001 |
| Least-squares mean (SE) | −0.71 (0.076) | 0.09 (0.074) | | |
| p-value [2] | <0.0001 | 0.2421 | | |
| Day 16, 8 AM Percent<br>Change from Baseline | | | | |
| n | 38 | 40 | | |
| Mean (SD) | −18.47 (12.457) | 3.71 (18.135) | | |
| Median | −17.13 | 0.12 | | |
| Min, Max | −38.8, 12.1 | −26.1, 66.7 | | |

Min = Minimum,
Max = Maximum,
SD = Standard deviation,
LS = Least-squares,
CI = Confidence interval,
SE = Standard error

[1] From an analysis of covariance (ANCOVA) with (percent) change from Baseline in Pupil Diameter as the dependent variable, treatment as a factor; and Baseline Pupil Diameter as the covariate.
[2] From a test comparing the individual treatment change from baseline LS mean to zero.
[3] The pooled data from the Study Eye and Fellow Eye.

TABLE 10B

Observed Change in Pupil Diameter Under Photopic Conditions

| Eye<br>Light Condition<br>Visit<br>Statistic | 1% w/w<br>Phentolamine<br>Mesylate<br>Ophthalmic Solution<br>(N = 19) | Placebo<br>(N = 20) | 1% w/w Phentolamine<br>Mesylate Ophthalmic<br>Solution vs. Placebo [1]<br>LS Mean Difference<br>(95% CI) | p-value |
|---|---|---|---|---|
| All Eyes [3]<br>Photopic<br>Day 16, 8 AM Percent Change<br>from Baseline ANCOVA [1] | | | −22.79 (−29.25, −16.32) | <0.0001 |
| Least-squares mean (SE)<br>p-value [2] | −18.78 (2.323)<br><0.0001 | 4.01 (2.264)<br>0.0807 | | |

Min = Minimum,
Max = Maximum,
SD = Standard deviation,
LS = Least-squares,
CI = Confidence interval,
SE = Standard error
[1] From an analysis of covariance (ANCOVA) with (percent) change from Baseline in Pupil Diameter as the dependent variable, treatment as a factor; and Baseline Pupil Diameter as the covariate.
[2] From a test comparing the individual treatment change from baseline LS mean to zero.

TABLE 11A

Observed Change in Pupil Diameter Under Mesopic Conditions

| Eye<br>Light Condition<br>Visit<br>Statistic | 1% w/w<br>Phentolamine<br>Mesylate<br>Ophthalmic Solution<br>(N = 19) | Placebo<br>(N = 20) | 1% w/w Phentolamine<br>Mesylate Ophthalmic<br>Solution vs. Placebo [1]<br>LS Mean Difference<br>(95% CI) | p-value |
|---|---|---|---|---|
| All Eyes [3]<br>Mesopic<br>Day 15, 8 AM Change from<br>Baseline ANCOVA [1] | | | −0.89 (−1.15, −0.63) | <0.0001 |
| Least-squares mean (SE)<br>p-value [2]<br>Day 15, 8 AM Percent<br>Change from Baseline | −1.02 (0.094)<br><0.0001 | −0.14 (0.092)<br>0.1424 | | |
| n<br>Mean (SD)<br>Median<br>Min, Max<br>Day 15, 8 AM Percent<br>Change from Baseline | 38<br>−21.65 (11.281)<br>−20.22<br>−38.6, 1.8 | 40<br>−2.03 (14.024)<br>−2.93<br>−22.5, 48.8 | −19.25 (−24.93, −13.57) | <0.0001 |
| ANCOVA [1]<br>Least-squares mean (SE)<br>p-value [2] | −21.46 (2.039)<br><0.0001 | −2.21 (1.988)<br>0.2707 | | |

Min = Minimum,
Max = Maximum,
SD = Standard deviation,
LS = Least-squares,
CI = Confidence interval,
SE = Standard error
[1] From an analysis of covariance (ANCOVA) with (percent) change from Baseline in Pupil Diameter as the dependent variable, treatment as a factor; and Baseline Pupil Diameter as the covariate.
[2] From a test comparing the individual treatment change from baseline LS mean to zero.
[3] The pooled data from the Study Eye and Fellow Eye.

TABLE 11B

| | | | | |
|---|---|---|---|---|
| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
| All Eyes [3] Mesopic Day 16, 8 AM Percent Change from Baseline | | | | |
| n | 38 | 40 | | |
| Mean (SD) | −19.09 (11.478) | −1.59 (13.521) | | |
| Median | −19.10 | −2.14 | | |
| Min, Max | −39.0, 1.0 | −24.9, 46.8 | | |
| Day 16, 8 AM Percent Change from Baseline ANCOVA [1] | | | −17.07 (−22.62, −11.53) | <0.0001 |
| Least-squares mean (SE) | −18.87 (1.991) | −1.79 (1.941) | | |
| p-value [2] | <0.0001 | 0.3581 | | |

Min = Minimum,
Max = Maximum,
SD = Standard deviation,
LS = Least-squares,
CI = Confidence interval,
SE = Standard error
[1] From an analysis of covariance (ANCOVA) with (percent) change from Baseline in Pupil Diameter as the dependent variable, treatment as a factor; and Baseline Pupil Diameter as the covariate.
[2] From a test comparing the individual treatment change from baseline LS mean to zero.
[3] The pooled data from the Study Eye and Fellow Eye.

Example 5—Evaluating Impact of Tetrahydrozoline on Pupil Reduction by Phentolamine Mesylate in Human Subjects A double-masked, randomized, 3-arm, parallel design, single dose study comparing the tolerability and effect of tetrahydrozoline, phentolamine mesylate, or tetrahydrozoline plus phentolamine mesylate on pupil size following topical administration of the agent(s) to the eye was conducted. A total of 45 human subjects were randomized into 3 groups (of 15 subjects each) and all subjects were treated sequentially with one drop per eye of two separate solutions.

Group 1 received one drop of ophthalmic tetrahydrozoline (VISINE®) in each eye followed by one drop of 0.2% (w/v) ophthalmic phentolamine mesylate in GENTEAL™ eye drop solution (i.e., the Tetrahydrozoline+Phentolamine Mesylate Group). GENTEAL™ eye drop solution is a sterile aqueous ophthalmic solution marketed commercially by Alcon.

Group 2 received one drop of placebo (GENTEAL® eye drop solution) in each eye followed by one drop of 0.2% (w/v) ophthalmic phentolamine mesylate in GENTEAL® eye drop solution (i.e., the Phentolamine Mesylate Group). Group 3 received one drop of ophthalmic tetrahydrozoline (VISINE®) in each eye followed by one drop of placebo (GENTEAL® eye drop solution) (i.e., the Tetrahydrozoline Group). Pupil size was measured. Additionally, eye redness was measured.

Figure 2:
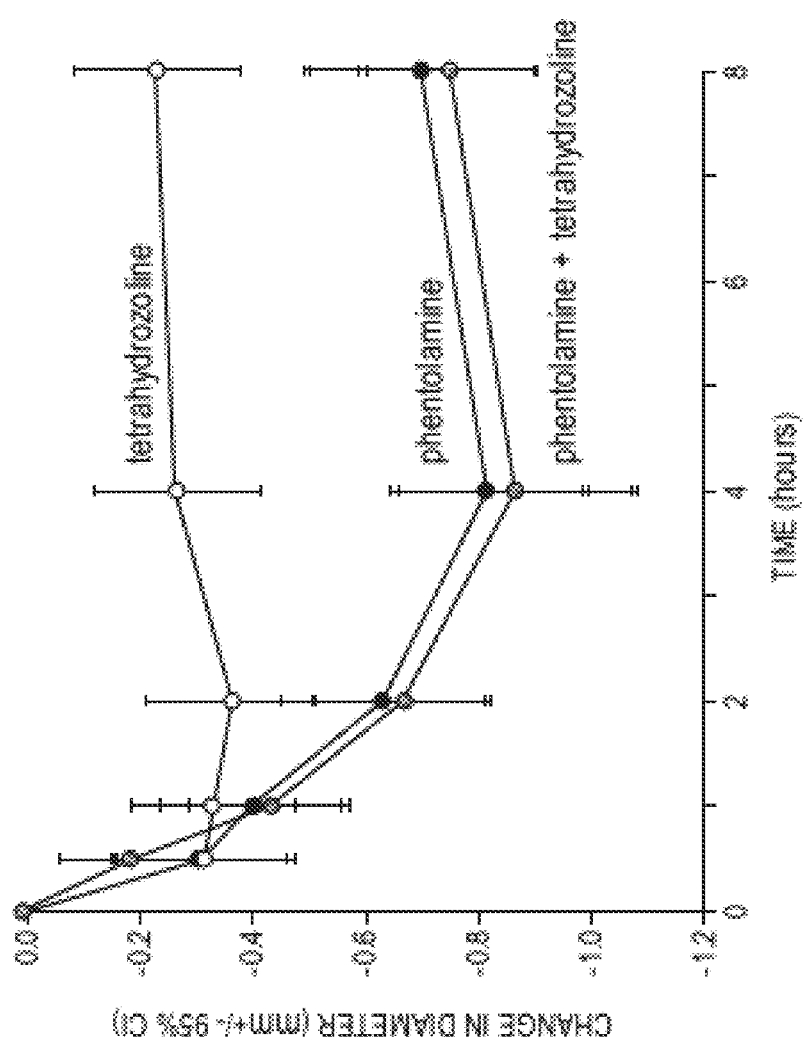
FIG. 2 is a graph showing observed change in pupil diameter observed in the clinical study described in Example 5.
Figure 3:
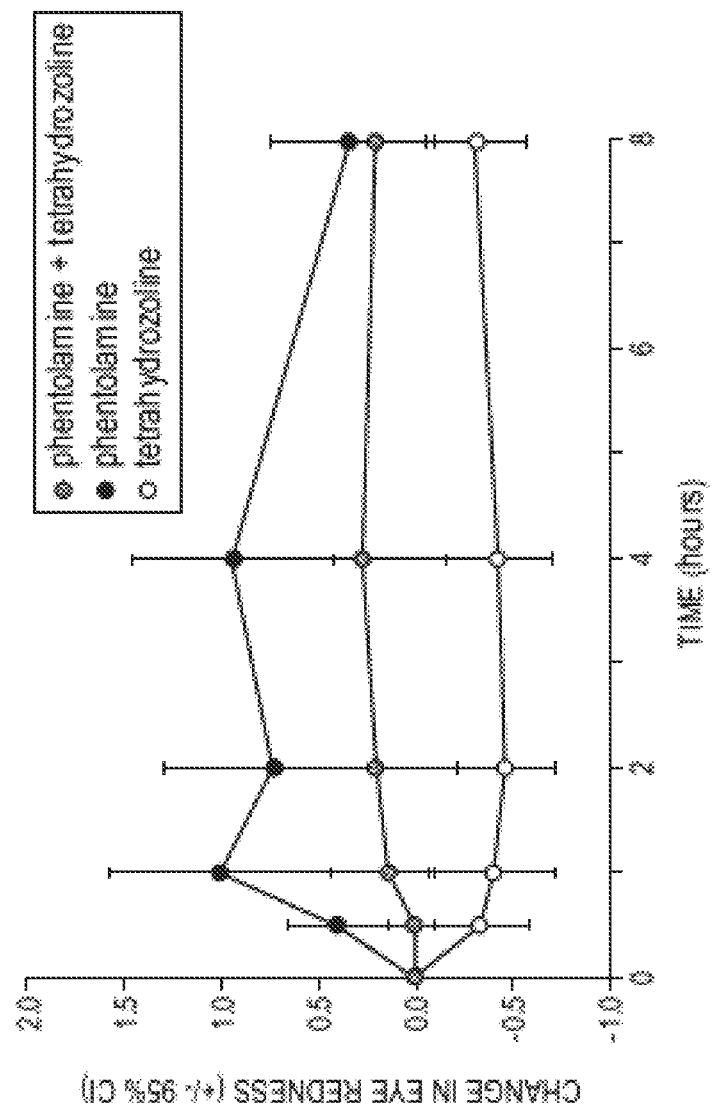
FIG. 3 is a graph showing observed eye redness observed in the clinical study described in Example 5.

Results observed from the study showed that administration of VISINE® (tetrahydrozoline ophthalmic solution) did not reduce the ability of 0.2% (w/v) ophthalmic phentolamine mesylate to reduce pupil diameter. Experimental results for pupil diameter are shown in FIG. 2. Results observed from the study also showed that (tetrahydrozoline ophthalmic solution) reduced eye redness caused by phentolamine mesylate. Experimental results for eye redness are shown in FIG. 3.

Example 6—Evaluating Phentolamine Mesylate for Causing Burning Sensation or Hyperemia Upon Administration to the Eye of Human Subjects One drop of 1% w/w Phentolamine Mesylate Ophthalmic Solution was administered to eye of human subjects. The subjects were asked to report any sensation of burning or hyperemia. The results observed are presented in Table 1 below for a study containing 32 patients that received 1% w/w Phentolamine Mesylate Ophthalmic Solution. The one drop of 1% w/w Phentolamine Mesylate Ophthalmic Solution resulted in less burning sensation and less hyperemia than that reported for REV-EYES® (0.5% w/w dapiprazole hydrochloride ophthalmic solution containing mannitol (2% w/w), sodium chloride, hydroxypropyl methylcellulose (0.4% w/w), edetate sodium (0.01% w/w), sodium phosphate dibasic, sodium phosphate monobasic, water for injection, and benzalkonium chloride (0.01% w/w) having a pH of approximately 6.6 and an osmolarity of approximately 415 mOsm)) in which two drops of REV-EYES® solution was administered to the eye of the patient and then after 5 minutes another two drops of REV-EYES® solution was administered to the eye of the patient.

TABLE 1

| Test Solution | Study No. | No. of Subjects | Percentage of Subjects Reporting Burning Sensation | Percentage of Subjects Reporting Hyperemia |
|---|---|---|---|---|
| REV-EYES ® | A | 40 | 40% | 100% |
| | B | 40 | 58% | 100% |
| | C | 38 | 82% | 62% |
| | D | 31 | 100% | 87% |

TABLE 1-continued

| Test Solution | Study No. | No. of Subjects | Percentage of Subjects Reporting Burning Sensation | Percentage of Subjects Reporting Hyperemia |
|---|---|---|---|---|
| 1% w/w Phentolamine Mesylate Ophthalmic Solution | 1 | 32 | 0% | 34% |

The composition of 1% w/w Phentolamine Mesylate Ophthalmic Solution is provided in the table below.

| Study Medication | Composition of Study Medication |
|---|---|
| 1% w/w Phentolamine Mesylate Ophthalmic Solution | 1% w/w phentol amine mesylate<br>4% w/w mannitol<br>3 mM buffer comprising sodium acetate and acetic acid<br>water<br>pH in the range 4.8 to 5.0 |

Example 7—Treatment of Presbyopia by Phentolamine Mesylate in a Human Subject Ability of phentolamine mesylate to treat a human subject suffering from presbyopia was evaluated according to the experimental procedure described below. Observed results are described below.

Part I—Experimental Procedures

Pupil diameter and visual acuity of the subject were determined at baseline (Time=−5 minutes), then 1% w/w Phentolamine Mesylate Ophthalmic Solution was administered to the subject (1 drop in each eye, Time=0 minutes). At Time=40 minutes, one drop of 1% pilocarpine HCl Ophthalmic Solution was administered only to the subject's left eye.

Pupil diameter and visual acuity were measured under photopic and mesopic conditions at Time=−5 minutes, 15 minutes, 30 minutes, 45 minutes, 60 minutes, 75 minutes, and 90 minutes. Pupil diameter was additionally measured at Time=14 hours. Pupil diameter was measured with an infrared pupilometer under scotopic conditions ("mesopic pupil diameter") and photopic conditions ("photopic pupil diameter"). Visual acuity was measured with an ETDRS chart held at 14 inches distance under mesopic conditions with a mesopic filter ("mesopic visual acuity") and under photopic conditions without a mesopic filter ("photopic visual acuity"). For reference, the lines on the ETDRS chart are: 20/125, 20/100, 20/80, 20/63, 20/50, 20/40, 20/32, 20/25, and 20/20.

The composition of 1% w/w Phentolamine Mesylate Ophthalmic Solution is provided in the table below.

| Study Medication | Composition of Study Medication |
|---|---|
| 1% w/w Phentolamine Mesylate Ophthalmic Solution | 1% w/w phentol amine mesylate<br>4% w/w mannitol<br>3 mM buffer comprising sodium acetate and acetic acid<br>water<br>pH in the range 4.8 to 5.0 |
| 1% w/w Pilocarpine Hydrochloride Ophthalmic Solution | 1% w/w pilocarpine hydrochloride<br>0.01% benzalkonium chloride<br>0.5% hypromellose 2910<br>boric acid<br>sodium chloride<br>sodium citrate<br>water<br>pH in the range 3.5 to 5.5 |

Part II—Results

Pupil diameter and near visual acuity data obtained from the study are presented in Table 1, below. In each eye, versus baseline, pupil diameter was reduced and near visual acuity was reduced by 1, 2, 3, or 4 lines.

TABLE 1

Pupil Diameter and Visual Acuity by Time Point and Lighting Conditions

| | | Right Eye | | Left Eye | | Both Eyes |
|---|---|---|---|---|---|---|
| Time | Conditions | Pupil Diameter | Visual Acuity | Pupil Diameter | Visual Acuity | Visual Acuity |
| −5 min. | photopic | 4.73 | 20/63 | 3.87 | 20/100 | 20/50 |
| | mesopic | 6.31 | 20/80 | 6.26 | 20/125 | 20/63 |
| 0 min. | | Administer 1% w/w Phentolamine Mesylate Ophthalmic Solution | | | | |
| 15 min. | photopic | 3.99 | 20/80 | 4.26 | 20/100 | 20/40 |
| | mesopic | 6.1 | 20/80 | 6.41 | 20/125 | 20/63 |
| 30 min. | photopic | 4.07 | 20/80 | 4.6 | 20/100 | 20/40 |
| | mesopic | 6.46 | 20/80 | 6.21 | 20/100 | 20/63 |
| 40 min. | | Administer 1% Pilocarpine HCl Ophthalmic Solution | | | | |
| 45 min. | photopic | 4.57 | 20/63 | 4.17 | 20/63 | |
| | mesopic | 6.36 | | 5.47 | | |
| 60 min. | photopic | 3.81 | 20/63 | 3.6 | 20/63 | 20/32 |
| | mesopic | 6.13 | 20/80 | 5.72 | 20/80 | 20/63 |
| 75 min. | photopic | 3.45 | 20/50 | 3.05 | 20/50 | 20/32 |
| | mesopic | 5.79 | 20/50 | 5.22 | 20/80 | 20/50 |
| 90 min. | photopic | 3.31 | 20/40 | 2.73 | 20/40 | 20/32 |
| | mesopic | 4.82 | | 6.35 | | |
| 14 hours | photopic | 3.16 | | 2.84 | | |
| | mesopic | 5.78 | | 5.58 | | |

Example 9—Treatment of Presbyopia by Phentolamine Mesylate in a Human Subject Ability of phentolamine mesylate to treat a human subject suffering from presbyopia may be evaluated according to a clinical study in which an aqueous ophthalmic solution containing phentolamine mesylate is administered to the eye of a patient, and then the patient is evaluated for improvement in visual performance, including near-visual visual performance. Experimental procedures and results are described below.

Part I—Experimental Procedures

Human subjects are screened for potential enrollment and, if qualified, enrolled in the study. Exemplary inclusion criteria and exclusion criteria for the study are set forth below. If a subject does not meet the inclusion/exclusion criteria but the investigator believes the subject should be in the study, a deviation may be allowed following a discussion between the Principal Investigator and Sponsor of the study.

Inclusion Criteria

Be ≥40 and ≤65 years of age.

Have distance-corrected near visual acuity (DCNVA) of 20/50 or worse in both eyes.

Have best corrected distance visual acuity (BCDVA) of 20/20 or better in both eyes, and currently depend on reading glasses or bifocals in which the near addition is >+1.00 diopters.

Be otherwise healthy and well-controlled subjects.

Be able and willing to give signed informed consent and follow study instructions.

Be able to self-administer study medication or to have study medication administered by a caregiver throughout the study period.

Exclusion Criteria

Ophthalmic:

Clinically significant ocular disease as deemed by the Investigator (e.g., untreated cataract, treated glaucoma, corneal edema, uveitis, severe keratoconjunctivitis sicca) that might interfere with the study.

Known hypersensitivity to any α-adrenoceptor antagonists or cholinergic parasympathomimetic agents.

Unwilling or unable to discontinue use of contact lenses during treatment period.

Ocular trauma, ocular surgery (e.g. IOLs) or laser procedure (e.g. LASIK, PRK) within 5 weeks prior to screening.

Recent or current evidence of ocular infection or inflammation in either eye. Current evidence of clinically significant blepharitis, conjunctivitis, or a history of herpes simplex or herpes zoster keratitis at Screening in either eye.

Ocular medication in either eye of any kind within 30 days of Screening, with the exception of a) ocular hypotensive medications (which must be washed out according to the provided schedule), b) lid scrubs (which can be used prior to Screening but cannot be used after Screening) or c) lubricating drops for dry eye (artificial tears), which can be used throughout the study.

Systemic:

Known hypersensitivity or contraindication to α- and/or β-adrenoceptor antagonists (e.g., chronic obstructive pulmonary disease or bronchial asthma; abnormally low blood pressure (BP) or heart rate (HR); second- or third-degree heart blockage or Congestive Heart Failure (CHF); severe diabetes).

Known hypersensitivity or contraindication to cholinergic parasympathomimetic agents.

Clinically significant systemic disease (e.g., uncontrolled diabetes, myasthenia gravis, cancer, hepatic, renal, endocrine or cardiovascular disorders) that might interfere with the study.

Initiation of treatment with, or any changes to the current dosage, drug or regimen of any topical or systemic adrenergic or cholinergic drugs up to 7 days prior to screening, or during the study.

Participation in any investigational study within 30 days prior to screening.

Women of childbearing potential who are pregnant, nursing, planning a pregnancy, or not using a medically acceptable form of birth control. Acceptable methods include the use of at least one of the following: intrauterine device (IUD), hormonal (oral, injection, patch, implant, ring), barrier with spermicide (condom, diaphragm), or abstinence. An adult woman is considered to be of childbearing potential unless she is 1 year postmenopausal or 3 months post-surgical sterilization. All females of childbearing potential must have a negative urine pregnancy test result at Visit 1/Screening and Visit 2 examinations and must intend not to become pregnant during the study.

Resting HR outside the normal range (50-110 beats per minute) at the Screening Visit. HR may be repeated only once if outside the normal range following at least a 5-minute rest period in the sitting position.

Hypertension with resting diastolic BP>105 mmHg or systolic BP>160 mmHg at the Screening Visit. BP may be repeated only once if outside the specified range following at least a 5-minute rest period in the sitting position.

Human subjects enrolled in the study shall randomized into two (or more) Treatment Groups with a 1:1 randomization. The Treatment Groups will receive doses of either:

Placebo Ophthalmic Solution,

1% w/w Phentolamine Mesylate Ophthalmic Solution, 1.5% w/w Phentolamine Mesylate Ophthalmic Solution, 2% w/w Phentolamine Mesylate Ophthalmic Solution, 1% w/w Phentolamine Mesylate Ophthalmic Solution and 1% Pilocarpine HCl Ophthalmic Solution, 1% w/w Phentolamine Mesylate Ophthalmic Solution and 0.2% to 0.25% Pilocarpine HCl Ophthalmic Solution, or 1% w/w Phentolamine Mesylate Ophthalmic Solution and 0.4% to 0.5% Pilocarpine HCl Ophthalmic Solution.

Preferably, the dose is a single drop of ophthalmic solution administered to the subject's eye. Treatment Groups receiving pilocarpine-containing treatments may receive them as aqueous solutions with or without the addition of a vegetable or mineral oil (e.g. castor oil). Description of certain study medications is provided in the following table.

| Study Medication | Composition of Study Medication |
| --- | --- |
| Placebo Ophthalmic Solution | 4% w/w mannitol<br>3 mM buffer comprising sodium acetate and acetic acid<br>water<br>pH in the range 4.8 to 5.0 |
| 1% w/w Phentolamine Mesylate Ophthalmic Solution | 1% w/w phentol amine mesylate<br>4% w/w mannitol<br>3 mM buffer comprising sodium acetate and acetic acid<br>water<br>pH in the range 4.8 to 5.0 |
| 1.5% w/w Phentolamine Mesylate Ophthalmic Solution | 1.5% w/w phentol amine mesylate<br>4% w/w mannitol<br>3 mM buffer comprising sodium acetate and acetic acid<br>water<br>pH in the range 4.8 to 5.0 |
| 2% w/w Phentolamine Mesylate Ophthalmic Solution | 2% w/w phentol amine mesylate<br>4% w/w mannitol<br>3 mM buffer comprising sodium acetate and acetic acid<br>water<br>pH in the range 4.8 to 5.0 |

Doses of study medication are given once daily for the first week and twice daily for the second week. Visual performance will be evaluated, which may include analysis of near-vision visual acuity, Distance Corrected Near Vision Acuity (DCNVA), Uncorrected Near Visual Acuity (UNVA), Uncorrected Intermediate Distance Visual Acuity (UIDVA), Best Corrected Distance Visual Acuity (BCDVA), other types of visual acuity measurements, and/or Vision questionnaire.

Measures of performance include change in baseline visual acuity for the study eye, the non-study eye, both eyes, and/or binocular. Example efficacy endpoints include: proportion of subjects gaining 3 lines or more in mesopic, high contrast, binocular DCNVA; proportion of subjects with a greater than or equal to 2-line improvement from Baseline in UNVA; visual function questionnaire responses between treatment groups at the pre-treatment time point at baseline and various study days; and other vision-performance and safety metrics.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating presbyopia in a patient according to a monotherapy treatment regimen, comprising administering to an eye of a patient in need thereof a dosage of a single therapeutic agent, wherein the single therapeutic agent is phentolamine mesylate, the dosage is administered as an eye drop, the dosage of the single therapeutic agent is one eye drop of a 1% (w/w) phentolamine mesylate solution, and the method results in an improvement in near-vision visual acuity characterized by at least a two-line improvement in the patient's vision measured using a vision chart.

2. The method of claim 1, wherein the method provides a therapeutic effect against presbyopia for a duration of at least 6 hours.

3. The method of claim 1, wherein the method provides a therapeutic effect against presbyopia for a duration of at least 12 hours.

4. The method of claim 1, wherein the method provides a therapeutic effect against presbyopia for a duration of at least 18 hours.

5. The method of claim 1, wherein the method results in an improvement in near-vision visual acuity characterized by at least a three-line improvement in the patient's vision measured using a vision chart.

6. The method of claim 2, wherein the method results in an improvement in near-vision visual acuity characterized by at least a three-line improvement in the patient's vision measured using a vision chart.

7. The method of claim 1, wherein the patient experiences an increase in eye redness of no more than one grade measured using the CCLRU Redness Grading Scale compared to the patient's level of eye redness without receiving said dosage of single therapeutic agent.

8. The method of claim 2, wherein the patient experiences an increase in eye redness of no more than one grade measured using the CCLRU Redness Grading Scale compared to the patient's level of eye redness without receiving said dosage of single therapeutic agent.

9. The method of claim 1, wherein as a result of the administering, the patient experiences the effect of having a pupil diameter of less than 3.0 mm in the eye that received said dosage when measured under photopic conditions.

10. The method of claim 2, wherein as a result of the administering, the patient experiences the effect of having a pupil diameter of less than 3.0 mm in the eye that received said dosage when measured under photopic conditions.

11. The method of claim 1, wherein a therapeutic benefit occurs within 1 hour after administering the single therapeutic agent.

12. The method of claim 2, wherein a therapeutic benefit occurs within 1 hour after administering the single therapeutic agent.

13. The method of claim 3, wherein a therapeutic benefit occurs within 1 hour after administering the single therapeutic agent.

14. The method of claim 4, wherein a therapeutic benefit occurs within 1 hour after administering the single therapeutic agent.

* * * * *